United States Patent [19]

Heavner et al.

[11] Patent Number: 5,753,617
[45] Date of Patent: May 19, 1998

[54] PEPTIDE INHIBITORS OF CELLULAR ADHESION

[75] Inventors: George A. Heavner, Malvern; Marian Kruszynski, King of Prussia, both of Pa.; Margaret L. Falcone, College Park, Md.

[73] Assignee: Centocor, Inc., Malvern, Pa.

[21] Appl. No.: 397,101

[22] PCT Filed: Sep. 8, 1993

[86] PCT No.: PCT/US93/08504

§ 371 Date: Mar. 7, 1995

§ 102(e) Date: Mar. 7, 1995

[87] PCT Pub. No.: WO94/05310

PCT Pub. Date: Mar. 17, 1994

Related U.S. Application Data

[63] Continuation-in-part of Ser. No. 941,653, Sep. 8, 1992, abandoned.

[51] Int. Cl.$^6$ .................. A61K 38/00; A61K 38/12; A61K 38/04; C07K 7/00
[52] U.S. Cl. .................. 514/9; 514/15; 530/317; 530/328
[58] Field of Search .................. 530/317, 328; 514/9, 15

[56] References Cited

U.S. PATENT DOCUMENTS

| | | | |
|---|---|---|---|
| 3,625,214 | 12/1971 | Higuchi | 128/260 |
| 4,789,734 | 12/1988 | Pierschbacher | 530/395 |
| 4,906,474 | 3/1990 | Langer et al. | 424/428 |
| 4,925,673 | 5/1990 | Steiner et al. | 424/455 |

FOREIGN PATENT DOCUMENTS

| | | |
|---|---|---|
| WO 91/07993 | 6/1991 | WIPO. |
| WO 91/19501 | 12/1991 | WIPO. |
| WO 91/19502 | 12/1991 | WIPO. |
| WO 92/01718 | 2/1992 | WIPO. |
| WO 92/02527 | 2/1992 | WIPO. |

OTHER PUBLICATIONS

Abbott, S.E. et a.., "Isolation and culture of synovial microvascular endothelial cells", *Arthritis and Rheumatism* 1992, 35(4), 401–406.

Ager, A. and Humphries, M.J., "Use of snythetic peptides to probe lymphocyte—high endothelial cell interactions. Lymphocytes recognize a ligand on the endothelial surface which contains the CS1 adhesion motif", *International Immunology* 1990, 2(10), 921–928.

Albelda, S.A. and Buck, C.A., "Integrins and other cell adhesion molecules", *FASEB* 1990, 4, 2868–2880.

Albelda, S.A., "Endothelial and epithelial cell adhesion molecules", *Am. J. Respir. Cell Mol. Biol.* 1991, 4, 195–203.

Aruffo, A. et al., "CD62/P–selectin recognition of myeloid and tumor cell sulfatides", *Cell* 1991, 67, 35–44.

Aruffo, A. et al., "Granule membrane protein 140 (GMP140) binds to carcinomas and carcinoma–derived cell lines", *PNAS USA* 1992, 89, 2292–2296.

Ball, G.E. et al., "Synthesis and structural analysis using 2–D NMR of sialyl Lewis X (SLe$^x$) and Lewis Le$^x$) oligosaccharides: ligands related to E–selectin [ELAM–1] binding", *American Chemical Society* 1992, 114, 5449–5451.

Bennett, J.S., "The molecular biology of platelet membrane proteins", *Seminars in Hematology* 1990, 27(2), 186–204.

Berg, M. and James, S.P., "human neutrophils release the leu–8 lymph node homing receptor during cell activation", *Blood* 1990, 76(11), 2381–2388.

Berg, E.L. et al., "A carbohydrate domain common to both Sialyl Le$^a$ and Sialyl Le$^x$ is recognized by the endothelial cell leukocyte adhesion molecule ELAM–1", *J. of Biological Research Communications* 1992, 266(23), 14869–14872.

Berg, E.L. et al., "Comparison of L–selectin and E–selectin ligand specificities: the L–selectin can bind the E–selectin ligands SIALYL Le$^x$ and SIALYL Le$^a$", *Biochemical and Biophysical Research Communicatons* 1992, 184(2), 1048–1055.

Bevilacqua, M. et al., "Endothelial leukocyte adhesion molecule 1: An inducible receptor for neutrophils related to complement regulatory proteins and lectins", *Science* 1989, 243, 1160–1165.

Bevilacqua, M. et al., "Selectins: a family of adhesion receptors", *Cell* 1991, 67, 233.

Bevilacqua, M. et al., "Identification of an inducible endothelial–leukocyte adhesion molecule", *Proc. Natl. Acad. Sci. USA* 1987, 84: 9238–9242.

Bodanszky, M. et al., "Peptide Synthesis", 2nd edition, John Wiley & Sons, 1976.

Brady, L.M. et al., "Long–term CD4$^+$ memory T cells from the spleen lack mel–14, the lynmph node homing receptor", *J. of Immunology* 1992, 148(2), 324–331.

Brandley, B.K. et al., "Carbohydrate ligands of the LEC cell adhesion molecules", *Cell* 1990, 63, 861–863.

Brown, E. et al., "Intefrin–associated protein: a 50–kD plasma membrane antigen physically and functionally associated with integrins", *J. of Cell Biology* 1990, 111(6), 2785–2794.

Bührer, C. et al., "Lymphocyte activation and regulation of three adhesion molecules with supposed function in homing: LECAM–1 (MEL–14 Antigen), LPAM–½ ($\alpha^4$–integrin) and CD44 (Pgp–1)", *Scandinavian J. of Immunology* 1992, 35, 107–120.

(List continued on next page.)

Primary Examiner—Cecilia J. Tsang
Assistant Examiner—Jennifer Harle
Attorney, Agent, or Firm—Woodcock Washburn Kurtz Mackiewicz & Norris LLP

[57] ABSTRACT

Novel cyclic peptides of the selectin 54–63 sequence exhibit unexpected and desired properties. Specific points of cyclization or conformational restriction in conjunction with specific substitutions have been identified that not only unexpectedly enhance the biological activity of these compounds, but also significantly increase their resistance to enzymatic degradation. Formulae of the active compounds and representative examples of preferred peptides are presented herein.

3 Claims, No Drawings

OTHER PUBLICATIONS

Camerini, D. et al., "Leu-8/TQ1 is the human equivalent of the Mel-14 lymph node homing receptor", *Nature* 1989, 342, 78–82.

Carmody, M.W. et al., "Production of monoclonal antibodies secific for platelet activation antigens and their use in evaluating platelet function", *Hybridoma* 1990, 9(6), 631–641.

Celi, a. et al., "PADGEM: an adhesion receptor for leukocytes on stimulated platelets and endothelial cells", *Procedures of the Society of Experimental and Biological Medicine* 1991, 198(2), 703–709.

Corral, L. et al., "Requirement for Sialic acid on neutrophils in a GMP-140 (PADGEM) mediated adhesive interaction with activated platelets", *Biochemical and Biophysical Research Communications* 1990, 172(3), 1349–1356.

Damle, N.K. et al., "GMP-140 (P-selectin/CD62) binds to chronically stimulated but not resting CD4+ T lymphocytes and regulates their production of proinflammatory cytokines", *European J. of Immunology* 1992, 22, 1789–1793.

de Bruijne-Admiraal, L.G. et al., "P-selectin mediates $Ca^{2+}$- dependent adhesion of activated platelets to many different types of leukocytes: detection by flow cytometry", *Blood* 1992, 80(1), 134–142.

Dejana, E. et al., "Endothelial leukocyte adhesion molecule-1-dependent adhesion of colon carcinoma cells to vascular endothelium is inhibited by an antibody to Lewis fucosylated type 1 carbohydrate chain", *Laboratory Investigation* 1992, 66(3), 324–330.

Disdier, M. et al., "Cytoplasmic domain of p-selectin (CD62) contains the signal for sorting into the regulated secretory pathway", *Molecular Biology of the Cell* 1992, 3, 309–121

Dunlop, L.C. et al., "Characterization of GMP-140(P-selectin) as a circulating plasma protein", *J. Exp. Med.* 1992, 175, 1147–1150.

Edgington, S.M., "How sweet it is: Selectin–mediating drugs", *Bio/Technology* 1992, 10, 383–389.

Erban, J.K. and Wagner, D.D., "A 130–kDa protein on endothelial cells binds to amino acids 15–42 of the Bβ chain of fibrinogen", *J. of Biological Chemistry* 1992, 267(4), 2451–2458.

Feizi, T., "Carbohydrate differentiationn antigens: probable ligands for cell adhesion molecules", 1991, *Elsevier Science Publishers Ltd. (UK)*, 84–86.

Fisher, M/A. and Malik, A.B., "Interactions between neutrophils and endothelial cells mediate lung vascular injury", *Applied Cardiopulmonary Pathophysiology* 1991, 4, 175–189.

Foxall, C. et al., "The three members of the selectin receptor family recognize a common carbohydrate epitope, the sialyl Lewis$^x$ oligosaccharide", *J. of Cell Biology* 1992, 117(4), 895–902.

Furie, B. et al., "PADGEM, a leukocyte receptor on activated platelets", *Current Studies in Hematology Blood Transf.* 1991, 58, 32–36.

Furie, M.B. et al., "E-selectin (endothelial–leukocyte adhesion molecule-1) is not required for the migration of neutrophils across IL-1 stimulated endothelium in vitro", *J. of immunology* 1992, 148(8), 2395–2404.

Gamble, J.R. et al., "prevention of activated neutrophil adhesion to endothelium by soluble adhesion protein GMP-140", *Science* 1990, 249, 414–416.

Geng, J. et al., "Rapid neutrophil adhesion to activated endothelium mediated by GMP-140", *Nature* 1990, 343, 757–760.

Geng, J. et al., "Neutrophil recognition requires a $Ca^{2+}$ – induced conformational change in the lectin domain of GMP-140", *J. of Biological Chemistry* 1991, 266(33), 22313–22319.

Gregoriadis, G. "Liposomes", Chap. 14 in Drug Carriers in Biology and Medicine, pp. 287–341, Academic Press, 1979.

Groves, R.W. et al., "Endothelial leucocyte adhesion molecule-1 (ELAM-1) expression in cutaneous inflammation", *British J. of Dermatology* 1991, 124, 117–123.

Hakkert, B.C. et al., "Neutrophil and monocyte adherence to and migration across monolayers of cytokine–activated endothelial cells: the contribution of CD18, ELAM-1, and VLA-4", *Blood* 1991, 78(10), 2721–2726.

Hamann, A. et al., "Homing reexamined: mouse LECAM-1 (MEL–14 antigen) is involved in lymphocyte migration into gut–associated lymphoid tissue", *Eur. J. Immunol.* 1991, 21, 2925–2929.

Hamburger, S.A. and McEver, R.P., "GMP-140 mediates adhesion of stimulated platelets to neutrophils", *Blood* 1990, 75(3), 550–554.

Handa, K. et al., "Selectin GMP-140 (CD62; PADGEM) binds to sialosyl–Le$^a$ and sialosyl–Le$^x$, and sulfated glycans modulate this binding", *Biochemical and Biophysical Research Communications* 1991, 181(3), 1223–1230.

Handa, K. et al., "Downregulation of GMP-140 (CD62 or PADGEM) expressin on plateltes by N, N–dimethyl and N,N,N–trimethyl derivatives of sphingosine", *Biochemistry* 1991, 30, 11682–11686.

Harrison, F.L., "Soluble vertebrate lectins: ubiquitous but inscrutable proteins", *J. of Cell Science* 1991, 100, 9–14.

Hattori, R. et al., "Stimulated secretion of endothelial von Willebrand factor is accompanied by rapid redistribution to the cell surface of the intracellular granule membrane protein GMP-140", *J. of Biol. Chem.* 1989, 264, 7768–7771.

Huang, K. et al., "A lymphocyte homing receptor (1-selectin) mediates the in vitro attachment of lymphocytes fo myelinated tracts of the central nervous system", *J. of Clinical Investigation* 1991, 88, 1778–1783.

Israels, S.J. et al., "Platelet dense granule membranes contain both granulophysin and P-selectin (GMP-140)", *Blood* 1992, 80(1), 143–152.

Issekutz, A.C. et al., "Role of neutrophils in the deposition of platelets during acute inflammation", *Lab. Invest.* 1983, 49(6), 716–724.

James, S.P. et al., "Multiple roles of Leu-8/MEL-14 in leukocyte adhesion and function", *Immunology Research* 1991, 19, 282–292.

Johnston, G.I. et al., "Structure of the human gene encoding granule membrane protein–140, a member of the selectin family of adhesion receptors for leukocytes", *J. of Biological Chemistry* 1990, 265(34), 21381–21385.

Johnston, G.I. et al., "Cloning of GMP-140, a granule membrane protein of platelets and endothelium: sequence similarity to proteins involved in cell adhesion and inflammation", *Cell* 1989, 56, 1033–1044.

Jutila, M.A. et al., Leukocyte traffic to sites of inflammation, *APMIS* 1992, 100, 191–201.

Jutila, M.A. et al., "function and regulation of the neutrophil MEL–14 antigen in vivo: comparison with LFA-1 and MAC-1", *J. of Immunology* 1989, 143(10), 3318–3324.

Kansas, G.S., "Structure and function of L–selectin", *APMIS*, 1992, 100, 287–293.

Karlsson, K.A., "Glycobiology: a growing field for drug design", *TIPS*, 1991, 12, 265–272.

Kitagawa, H. et al., "Characterization of mucin–type oligosaccharides with the sialyl–Le$^a$ structure from human colorectal adenocarcinoma", *Biochemical and Biophysical Research communications* 1991, 178(3), 1429–1436.

Knapp, W. et al., "Antibody–defined cell surface molecules of the immune system", *Current Opinion in Immunology* 1990, 2, 884–891.

Koedam, J.A. et al., "P–selectin, a granule membrane protein of platelets and endothelial cells, follows the regulated secretory pathway in AtT–20 cells", *J. of Cell Biology* 1992, 116(3), 617–625.

Kojima, N. et al., "Inhibition of selectin–dependent tumor cell adhesion to endothelial cells and platelets by blocking o–glycosylation of these cells", *Biochemicals and Biophysical Research Communications* 1992, 182(3), 1288–1295.

Kuijpers, T.W. et al., Role of endothelial leukocyte adhesion molecule–1 and platelet–activationg factor in neutrophil adherence to IL–1 prestimulated endothelial cells, *J. of Immunology* 1991, 147(4), 1369–1376.

Larkin, M. et al., "Spectrum of sialylated and nonsialylated fuco–olifosaccharides bound by the endothelial–leukocyte adhesion molecule E–selectin", *J. of Biological Chemistry* 1992, 267(19), 13661–13668.

Larsen, E. et al., "PADGEM protein: a receptor that mediates the interaction of activated platelets with neutrophils and monocytes", *Cell* 1989, 59, 305–312.

Larsen, E. et al., "PADGEM–dependent adhesion of platelets to monocytes and neutrophils is mediated by a lineage–specific carbohydrate, LNF III (CD15)", *Cell* 1990, 63, 467–474.

Lasky, L.A. et al., "An endothelial ligand for L–selectin is a novel mucin–like molecule", *Cell* 1992, 69, 927–938.

Lasky, L.A. et al., "Cloning of a lymphocyte homing receptor reveals a lectin domain", *Cell* 1989, 56, 1045–1055.

Lawrence, M.B. et al., "Leukocytes roll on a selectin at physiologic flow rates: distinction from and prerequisite for adhesion through integrins", *Cell* 1991, 65, 859–873.

Leeuwenberg, J.F.M. et al., "The ligand recognized by ELAM–1 on HL60 cells is not carried by N–linked oligosaccharides", *Eur. J. Immunol.* 1991, 21, 3057–3059.

Leeuwenberg, J.F.M. et al., "Adhesion of polymorphonuclear cells to human endothelial cells. adhesion–molecule–dependent, and Fc receptor–mediated adhesion–molecule–independent mechanisma", *Clin. exp. Immunol.* 1990, 81, 496–500.

Leeuwenberg, J.F.M. et al., "Role of ELAM–1 in adhesion of monocytes to activated human endothelial cells", *Scandinavian J. of Immunology* 1992, 35, 335–341.

Ley, K. et al., "Shear dependent inhibition of granulocyte adhesion to cultured endothelium by dextran sulfate", *Blood* 1989, 73(5), 1324–1330.

Lin, Y. et al., "Conformational studies os sialyl Lewis X in aqueous solution", *J. of American Chemical Society* 1992, 114, 5452–5454.

Lobb, R.R. et al., "Expression and functional characterization of soluble form of endothelial–leukocyte adhesion molecule 1", *J. of Immunology* 1991, 147(1), 124–129.

Lorant, D.E. et al., "Coexpression of GMP–140 and PAF by endothelium stimulated by histamine or thrombin: a juxtacrine system for adhesion and activation of neutrophils", *J. of Cell Biology* 1991, 115(1), 223–234.

Lowe, J.B. et al., "ELAM–1–dependent cell adhesion to vascular endothelium determined by a transfected human fucosyltransferase cDNA", *Cell* 1990, 63, 475–484.

Lowe, J.B. et al., "A transfected human fucosyltransferase cDNA determines biosynthesis of oligosaccharide ligand(s) for endothelial–leukocyte adhesion molecule I", *Biochemical Society Transactions* 1991, 19(3), 649–653.

Majuri, M.L. et al., "Recombinant E–selectin–protein mediates tumor cell adhesion via sialyl–Lea and sialyl–Lex", *Biochemical and Biophysical Research Communications* 1992, 182(3), 1376–1382.

May, G.L. et al., "GMP–140 (P–selectin inhibits human neutrophil activation by lipopolysaccharide spectroscopy", *Biochemical and Biophysical Research Communications* 1992, 183(3), 1062–1069.

McEver, R.P., "Leukocyte interactions mediated by selectins", *Thrombosis and Haemostasis* 1991, 66(1), 80–87.

McEver, R.P., "GMP–140, a receptor that mediates interactions of leukocytes with activates platelets and endothelium", *TCM* 1991, 1(4), 152–156.

McEver, R.P. et al., "GMP–140, a platelet α–granule membrane protein, is also synthesized by vascular endothelial cells and is localized in weibel–palade bodies", *J. Clin. Invest.* 1989, 84, 92–99.

McEver, R.P., "Selectins: Novel receptors that mediate leukocyte adhesion during inflammation", *Thrombosis and Haemostasis* 1990, 65(3), 223–228.

McEver, R.P., "GMP–140: a receptor for neutrophils and monocytes on activated platelets and endothelium", *J. of Cellular Biochemistry* 1991, 45, 156–161.

McEver, R.P. et al., "The platelet α–granule membrane protein GMP–140 is also synthesized by human vascular endothelial cells and is present in blood vessels of diverse tissues", *Blood* 1987, 70(5) Suppl.1, 355a, Abstract No. 1274.

McEver, R.P. and Martin, M.N. "A monoclonal antibody to a membrane glycoprotein binds only to activated platelets", *J. of Biol. Chem.* 1984, 259(15), 9799–9804.

Merrifield, R.B., "Solid Phase Peptide Synthesis. I. The Synthesis of a Tetrapeptide", *J. Am. Chem. Soc.* 1963, 85, 2149–2154.

Metzelaar, M.J. et al., "Biochemical and immunohistochemical characteristics of CD62 and CD63 monoclonal antibodies", *Virchows Archives B Cell Pathology* 1991, 61, 269–277.

Montefort, S. and Holgate, S.T., "Adhesion molecules and their role in inflammation", *Respiratory Medicine* 1991, 85, 91–99.

Moore, K.L. et al., "GMP–140 binds to a glycoprotein receptor on human neutrophils: evidence for a lectin–like interaction", *J. of Cell Biol.* 1991, 112, 491–499.

Müller–Eberhard, H.J., "Molecular organization and function of the complement system", *Ann. Rev. Biochem.* 1988, 57, 321–347.

Mulligan, M.S. et al., "Role of endothelial–leukocyte adhesionn molecule 1 (ELAM–1) in neutrophil–mediated lung injury in rats", *J. Clin. Invest.* 1991, 88, 1396–1406.

Norton, J. et al., "Expression of adhesion molecules in human intestinal graft–versus–host disease", *Clin. Exp. Immunol.* 1992, 87, 231–236.

Ord, D.C. et al., "Structure of the gene encoding the human leukocyte adhesion molecule–1 (TQ1, Leu–8) of lymphocytes and neutrophils", *J. of Biological Chemistry* 1990, 265(14), 7760–7767.

Osborn, L., "Leukocyte adhesion to endothelium in inflammation", *Cell* 1990, 62, 3–6.

Parish, C.R. et al., "Carbohydrate recognition molecules on lymphocytes", *Biochem. Soc. Trans.* 1992, 20(2), 295–297.

Parmentier, S. et al., Inhibition of platelet functions by a monoclonal antibody (LYP20) directed against a granule membrane glycoprotein (GMP–140/PADGEM), *Blood* 1991, 77(8), 1734–1739.

Parmentier, S. et al., "A new family of cell–cell adhesion molecules: ELAM–1, GP90 $^{MEL-14}$ and GMP–140", *Fundamental and Clinical Aspects* 1991, 206, 63–73.

Parmentier, S. et al., "New families of adhesion molecules play a vital role in platelet functions", *Immunology Today* 1990, 11(7).

Patarroyo, M., "Short analytical review: Leukocyte adhesion in host defense and tissue injury", *Clinical Immunology and Immunopathology* 1991, 60, 333–348.

Picker, L.J. et al., "The neutrophil selectin LECAM–1 presents carbohydrate ligands to the vascular selectins ELAM–1 and GMP–140", *Cell* 1991, 66, 921–933.

Pigott, R. et al., "Structural and functional studies of the endothelial activation antigen endothelial leucocyte adhesion molecule–1 using a panel of monoclonal antibodies", *J. of Immunology* 1991, 147(1), 130–135.

Pober, J.S. and Cotran, R.S., "What can be learned from the expression of endothelial adhesion molecules in tissues", *Laboratory Investigation* 1991, 64(3), 301–305.

Pober, J.S. and Cotran, R.S. "The role of endothelial cells in inflammation", *Transplantation* 1990, 50(4), 537–544.

Postigo, A.A. et al., "Increased binding of synovial t lumphocytes from rheumatoid arthritis to endothelial–leukocyte adhesion molecule–1 (ELAM–1) and vascular cell adhesion molecule–1 (VCAM–1)", *J. of Clinical Investigation* 1992, 89, 1445–1452.

Rinder, H.M. et al., "Dynamics of leukocyte–platelet adhesion in whole blood", *Blood* 1991, 78(7), 1730–1737.

Rinder, H.M. et al., "Activated and unactivated platelet adhesion to monocytes and neutrophils", *Blood* 1991, 78(7), 1760–1769.

Romson, J.L. et al., "Reduction of the extent of ischemic myocardial injury by neutrophil depletion in the dog", *Circulation* 1983, 67, 1016–1023.

Ryan, U.S. and Worthington, R.E., "Cell–cell contact mechanisms", *Current Opinion in Immunology* 1992, 4, 33–37.

Shimizu, Y. et al., "Four molecular pathways of T cell adhesion to endothelial cells: roles of LFA–1, VCAM–1, and ELAM–1 and changes in pathway hierarchy under different activation conditions", *J. of Cell Biology* 1991, 113(5), 1203–1212.

Shimizu, Y. et al., "Activation–independent binding of human memory T cells to adhesion molecule ELAM–1", *Nature* 1991, 349, 799–802.

Shipp, M. A. et al., "CD10 (CALLA) neutral endopeptidase 24. 11 modulates inflammatory peptide–induced changes in neutrophil morphology, migration, and adhesion proteins and is itself regulated by newtrophil activation", *Blood* 1991, 78(7), 1834–1841.

Siegelman, M.H. et al., "The mouse lymph node homing receptor is identical with the lymphocyte cell surface marker Ly–22: role of the EGF domain in endothelial binding", *Cell* 1990, 61, 611–622.

Skinner, M.P. et al., "GMP–140 binding to neutrophils is inhibited by sulfated glycans", *J. of Biological Chemistry* 1991, 266(9), 5371–5374.

Smith, C.W., "Molecular determinants of neutrophil adhesion", *Am. J. Respir. Cell Mol. Biol.* 1990, 2, 487–489.

Smith, C.W., "PMN adhesion and extravasation as a paradigm for tumor cell dissemination", *Cancer and Metastasis Reviews* 1991, 10, 61–78.

Spertini, O. et al., "Monocyte attachment to activated human vascular endothelium in vitro is mediated by leukocyte adhesion molecule–1 (L–selectin) under nonstatic conditions", *J. Exp. Med.* 1992, 175, 1789–1792.

Spertini, O. et al., "Leukocyte adhesion molecule–1 (LAM–1, l–selectin) interacts with an inducible endothelial cell ligand to support leukocyte adhesion", *J. of Immunology* 1991, 147(8), 2565–2573.

Springer, T.A. and Lasky, L.A., "Sticky sugars for selectins", *Nature* 1991, 349, 196–197.

Springer, T.A., "Adhesion receptors of the immune system", *Nature* 1990, 346, 425–434.

Stoolman, L.M., "Selectins (LEC–CAMs): Lectin–like receptors involved in lymphocyte recirculation and leukocyte recuitment", in *Cell surface Carbohydrates and Cell Development*, Fukuda, M. Ph.D., Ed., CRC Press, 71–98.

Swiedler, S.J., "Invited commentary to the glyco–forum", *Glycobiology* 1991, 1(3), 237–241.

Takada, A. et al., "Adhesion of human cancer cells to vascular endothelium mediated by a carbohydrate antigen, sialkyl Lewis A", *Biochemical and Biophysical Research Communications* 1991, 179(2), 713–719.

Tedder, T.F. et al., "Isolation and chromosomal localization of cDNAs encoding a novel human lymphocyte cell surface molecule, LAM–1", *J. Exp. Med.* 1989, 170, 123–133.

Todoroki, N. et al., "Enhancement by IL–1$\beta$ and IFN–$\tau$ of platelet activation: adhesion to leukocytes via GMP–140/PADGEM protein (CD62)", *Biochem. and Biophys. Res. Commun.* 1991, 179(2), 756–761.

Toothill, V.J. et al., "Characterization of the enhanced adhesion of neutrophil leukocytes to thrombin–stimulated endothelial cells", *J. of Immunology* 1990, 145, 283–291.

True, D.D. et al., "Requirement for sialyl acid on the endothelial ligand of a lymphocyte homing receptor", *J. of Cell Biology* 1990, 111(6 pt.1), 2757–2764.

Tyrrell, D. et al., "Structural requirements for the carbohydrate ligan of E–selectin", *Proc. Natl. Acad. Sci. USA* 1991, 88, 10372–10376.

Vadas, M.A. and Gamble, J.R., "Regulation of the adhesion of neutrophils to endothelium", *Biochemical Pharmacology* 1990, 40(8), 1683–1687.

Volpes, R. et al., "Vascular adhesion molecules in acute and chronic liver inflammation", *Hepatology* 1992, 15(2), 269–275.

Walcheck, B. et al., "Characterization of the bovine peropheral lymph node homing recceptor: a lectin cell adhesion molecule (LECAM)", *Eur. J. Immunol.* 1992, 22, 469–476.

Watson, M.L. et al., "Genomic organization of the selectin family of leukocyte adhesion molecules on human and mouse chromosome 1", *J. Exp. Med.* 1990, 172, 263–272.

Watson, S. R. et al., "Neutrophil influx into an inflammatory site inhibited by a soluble homing receptor–IgG chimaera", *Nature* 1991, 349, 164–166.

Watson, S. R. et al., "The complement binding–like domains of the murine homing receptor facilitate lectin activity", *J. of Cell Biology* 1991, 115(1), 235–243.

Wautier, J. et al., "Symposium: Leukocyte adhesion—rheological biophysiccal and pharmacological approaches", *Biorheology* 1990, 27, 425–432.

Winocour, P.D. et al., "A member of the selectin family (GMP–140/PADGEM) is expressed on thrombin–stimulated rat platelets in vitro", *Comp. Biochem. Physiol.* 1992, 102A(2), 265–271.

Wong, C.S. et al., "Adhesion protein GMP140 inhibits superoxide anion release by human neutrophils", *Proc. Natl. Acad. Sci. USA* 1991, 88, 2397–2401.

Yednock, T.A. and Rosen, S.D., "Lymphocyte homing", *Advances in Immunology* 1989, 44, 313–378.

Yong, K. and Khwaja, A., "Leuocyte cellular adhesion molecules", *Blood Reviews* 1990, 4, 21–225.

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 10 amino acids
        ( B ) TYPE: amino acid
        ( C ) STRANDEDNESS:
        ( D ) TOPOLOGY: unknown ( i i ) MOLECULE TYPE: peptide ( i x ) FEATURE:
        ( A ) OTHER INFORMATION: Cyclic structure involving cyclization between Lys(6) and Glu(10); Amide terminated.

( x i ) SEQUENCE DESCRIPTION: SEQ ID NO:1:

Arg Lys Ile Gly Gly Lys Trp Thr Trp Glu
1               5                   10

( 2 ) INFORMATION FOR SEQ ID NO:2:

( i ) SEQUENCE CHARACTERISTICS:
        ( A ) LENGTH: 10 amino acids
        ( B ) TYPE: amino acid
        ( C ) STRANDEDNESS:
        ( D ) TOPOLOGY: unknown ( i i ) MOLECULE TYPE: peptide ( i x ) FEATURE:
        ( A ) OTHER INFORMATION: Cyclic structure involving cyclization between Glu(6) and Lys(10); Amide terminated.

( x i ) SEQUENCE DESCRIPTION: SEQ ID NO:2:

Arg Lys Ile Gly Gly Glu Trp Thr Trp Lys
1               5                   10

( 2 ) INFORMATION FOR SEQ ID NO:3:

( i ) SEQUENCE CHARACTERISTICS:
        ( A ) LENGTH: 10 amino acids
        ( B ) TYPE: amino acid
        ( C ) STRANDEDNESS:
        ( D ) TOPOLOGY: unknown ( i i ) MOLECULE TYPE: peptide ( i x ) FEATURE:
        ( A ) OTHER INFORMATION: Cyclic structure involving cyclization between Asp(3) and Xaa(6), wherein Xaa is diaminopropionyl; Amide terminated.

( x i ) SEQUENCE DESCRIPTION: SEQ ID NO:3:

Arg Lys Asp Gly Gly Xaa Trp Thr Trp Val
1               5                   10

( 2 ) INFORMATION FOR SEQ ID NO:4:

( i ) SEQUENCE CHARACTERISTICS:
        ( A ) LENGTH: 10 amino acids
        ( B ) TYPE: amino acid
        ( C ) STRANDEDNESS:
        ( D ) TOPOLOGY: unknown ( i i ) MOLECULE TYPE: peptide ( i x ) FEATURE:
    ( A ) OTHER INFORMATION: Cyclic structure involving
        cyclization between Xaa(3) and Asp(6), wherein
        Xaa is diaminopropionyl; Amide terminated.

( x i ) SEQUENCE DESCRIPTION: SEQ ID NO:4:

```
Arg  Lys  Xaa  Gly  Gly  Asp  Trp  Thr  Trp  Val
 1              5                          10
```

( 2 ) INFORMATION FOR SEQ ID NO:5:

( i ) SEQUENCE CHARACTERISTICS:
        ( A ) LENGTH: 10 amino acids
        ( B ) TYPE: amino acid
        ( C ) STRANDEDNESS:
        ( D ) TOPOLOGY: unknown ( i i ) MOLECULE TYPE: peptide ( i x ) FEATURE:
        ( A ) OTHER INFORMATION: Cyclic structure involving
            cyclization between Glu(1) and Lys(6); Amide
            terminated.

( x i ) SEQUENCE DESCRIPTION: SEQ ID NO:5:

```
Glu  Lys  Ile  Gly  Gly  Lys  Trp  Thr  Trp  Val
 1              5                          10
```

( 2 ) INFORMATION FOR SEQ ID NO:6:

( i ) SEQUENCE CHARACTERISTICS:
        ( A ) LENGTH: 10 amino acids
        ( B ) TYPE: amino acid
        ( C ) STRANDEDNESS:
        ( D ) TOPOLOGY: unknown ( i i ) MOLECULE TYPE: peptide ( i x ) FEATURE:
        ( A ) OTHER INFORMATION: Cyclic structure involving
            cyclization between Lys(1) and Glu(6); Amide
            terminated.

( x i ) SEQUENCE DESCRIPTION: SEQ ID NO:6:

```
Lys  Lys  Ile  Gly  Gly  Glu  Trp  Thr  Trp  Val
 1              5                          10
```

( 2 ) INFORMATION FOR SEQ ID NO:7:

( i ) SEQUENCE CHARACTERISTICS:
        ( A ) LENGTH: 10 amino acids
        ( B ) TYPE: amino acid
        ( C ) STRANDEDNESS:
        ( D ) TOPOLOGY: unknown ( i i ) MOLECULE TYPE: peptide ( i x ) FEATURE:
        ( A ) OTHER INFORMATION: Cyclic structure involving
            cyclization between Cys(1) and Cys(10); Amide
            terminated.

( x i ) SEQUENCE DESCRIPTION: SEQ ID NO:7:

```
Cys  Lys  Ile  Gly  Gly  Ile  Trp  Thr  Trp  Cys
 1              5                          10
```

( 2 ) INFORMATION FOR SEQ ID NO:8:

( i ) SEQUENCE CHARACTERISTICS:
        ( A ) LENGTH: 10 amino acids
        ( B ) TYPE: amino acid ( C ) STRANDEDNESS:
( D ) TOPOLOGY: unknown ( i i ) MOLECULE TYPE: peptide ( i x ) FEATURE:
( A ) OTHER INFORMATION: Cyclic structure involving cyclization between Cys(2) and Cys(6); Amide terminated.

( x i ) SEQUENCE DESCRIPTION: SEQ ID NO:8:

Arg Cys Ile Gly Gly Cys Trp Thr Trp Val
 1               5                   10

( 2 ) INFORMATION FOR SEQ ID NO:9:

( i ) SEQUENCE CHARACTERISTICS:
( A ) LENGTH: 9 amino acids
( B ) TYPE: amino acid
( C ) STRANDEDNESS:
( D ) TOPOLOGY: unknown ( i i ) MOLECULE TYPE: peptide ( i x ) FEATURE:
( A ) OTHER INFORMATION: Cyclic structure involving cyclization between Cys(1) and Cys(5); Amide terminated.

( x i ) SEQUENCE DESCRIPTION: SEQ ID NO:9:

Cys Arg Gly Gly Cys Trp Thr Trp Val
 1               5

( 2 ) INFORMATION FOR SEQ ID NO:10:

( i ) SEQUENCE CHARACTERISTICS:
( A ) LENGTH: 9 amino acids
( B ) TYPE: amino acid
( C ) STRANDEDNESS:
( D ) TOPOLOGY: unknown ( i i ) MOLECULE TYPE: peptide ( i x ) FEATURE:
( A ) OTHER INFORMATION: Cyclic structure involving cyclization between Cys(3) and Cys(6); Amide terminated.

( x i ) SEQUENCE DESCRIPTION: SEQ ID NO:10:

Arg Lys Cys Gly Gly Cys Trp Thr Trp
 1               5

( 2 ) INFORMATION FOR SEQ ID NO:11:

( i ) SEQUENCE CHARACTERISTICS:
( A ) LENGTH: 10 amino acids
( B ) TYPE: amino acid
( C ) STRANDEDNESS:
( D ) TOPOLOGY: unknown ( i i ) MOLECULE TYPE: peptide ( i x ) FEATURE:
( A ) OTHER INFORMATION: Cyclic structure involving cyclization between Cys(3) and Cys(6); Amide terminated.

( x i ) SEQUENCE DESCRIPTION: SEQ ID NO:11:

Arg Lys Cys Gly Gly Cys Trp Thr Trp Val
          1               5                   10

( 2 ) INFORMATION FOR SEQ ID NO:12:

( i ) SEQUENCE CHARACTERISTICS:

(A) LENGTH: 10 amino acids
(B) TYPE: amino acid
(C) STRANDEDNESS:
(D) TOPOLOGY: unknown (ii) MOLECULE TYPE: peptide (ix) FEATURE:
(A) OTHER INFORMATION: Cyclic structure involving cyclization between Cys(3) and Xaa(6), wherein Xaa is D-penicillamine; Amide terminated.

(xi) SEQUENCE DESCRIPTION: SEQ ID NO:12:

Arg Lys Cys Gly Gly Xaa Trp Thr Trp Val
 1           5                      10

(2) INFORMATION FOR SEQ ID NO:13:

(i) SEQUENCE CHARACTERISTICS:
(A) LENGTH: 10 amino acids
(B) TYPE: amino acid
(C) STRANDEDNESS:
(D) TOPOLOGY: unknown (ii) MOLECULE TYPE: peptide (ix) FEATURE:
(A) OTHER INFORMATION: Cyclic structure involving cyclization between Xaa(3) and Cys(6), wherein Xaa is D-penicillamine; Amide terminated.

(xi) SEQUENCE DESCRIPTION: SEQ ID NO:13:

Arg Lys Xaa Gly Gly Cys Trp Thr Trp Val
 1           5                      10

(2) INFORMATION FOR SEQ ID NO:14:

(i) SEQUENCE CHARACTERISTICS:
(A) LENGTH: 10 amino acids
(B) TYPE: amino acid
(C) STRANDEDNESS:
(D) TOPOLOGY: unknown (ii) MOLECULE TYPE: peptide (ix) FEATURE:
(A) OTHER INFORMATION: Cyclic structure involving cyclization between Xaa(3) and Xaa(6), wherein Xaa is D-penicillamine; Amide terminated.

(xi) SEQUENCE DESCRIPTION: SEQ ID NO:14:

Arg Lys Xaa Gly Gly Xaa Trp Thr Trp Val
 1           5                      10

(2) INFORMATION FOR SEQ ID NO:15:

(i) SEQUENCE CHARACTERISTICS:
(A) LENGTH: 9 amino acids
(B) TYPE: amino acid
(C) STRANDEDNESS:
(D) TOPOLOGY: unknown (ii) MOLECULE TYPE: peptide (ix) FEATURE:
(A) OTHER INFORMATION: Cyclic structure involving cyclization between Cys(2) and Cys(5); Amide terminated.

(xi) SEQUENCE DESCRIPTION: SEQ ID NO:15:

Lys Cys Gly Gly Cys Trp Thr Trp Val
 1           5                   9

( 2 ) INFORMATION FOR SEQ ID NO:16:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: unknown ( i i ) MOLECULE TYPE: peptide ( i x ) FEATURE:
        ( A ) OTHER INFORMATION: Cyclic structure involving
            cyclization between Cys(1) and Cys(4); Amide
            terminated.

( x i ) SEQUENCE DESCRIPTION: SEQ ID NO:16:

Cys Gly Gly Cys Trp Thr Trp Val
1               5

( 2 ) INFORMATION FOR SEQ ID NO:17:

( i ) SEQUENCE CHARACTERISTICS:
        ( A ) LENGTH: 10 amino acids
        ( B ) TYPE: amino acid
        ( C ) STRANDEDNESS:
        ( D ) TOPOLOGY: unknown ( i i ) MOLECULE TYPE: peptide ( i x ) FEATURE:
        ( A ) OTHER INFORMATION: Cyclic structure involving
            cyclization between Glu(4) and Lys(8); Amide
            terminated.

( x i ) SEQUENCE DESCRIPTION: SEQ ID NO:17:

Arg Lys Ile Glu Gly Ile Trp Lys Trp Val
1               5                   10

( 2 ) INFORMATION FOR SEQ ID NO:18:

( i ) SEQUENCE CHARACTERISTICS:
        ( A ) LENGTH: 10 amino acids
        ( B ) TYPE: amino acid
        ( C ) STRANDEDNESS:
        ( D ) TOPOLOGY: unknown ( i i ) MOLECULE TYPE: peptide ( i x ) FEATURE:
        ( A ) OTHER INFORMATION: Cyclic structure involving
            cyclization between Lys(4) and Glu(8); Amide
            terminated.

( x i ) SEQUENCE DESCRIPTION: SEQ ID NO:18:

Arg Lys Ile Lys Gly Ile Trp Glu Trp Val
1               5                   10

( 2 ) INFORMATION FOR SEQ ID NO:19:

( i ) SEQUENCE CHARACTERISTICS:
        ( A ) LENGTH: 10 amino acids
        ( B ) TYPE: amino acid
        ( C ) STRANDEDNESS:
        ( D ) TOPOLOGY: unknown ( i i ) MOLECULE TYPE: peptide ( i x ) FEATURE:
        ( A ) OTHER INFORMATION: Cyclic structure involving
            cyclization between Cys(6) and Cys(10); Amide
            terminated.

( x i ) SEQUENCE DESCRIPTION: SEQ ID NO:19:

```
Arg  Lys  Ile  Gly  Gly  Cys  Trp  Thr  Trp  Cys
 1             5                         10
```

PEPTIDE INHIBITORS OF CELLULAR ADHESION

This application is a continuation-in-part of U.S. Ser. No. 941,653, filed Sep. 8, 1992, now abandoned. This invention relates to peptides which inhibit binding of selecting, such as P-selectin, E-selectin and L-selectin, and ICAM-1.

BACKGROUND OF THE INVENTION

The adherence of platelets and leukocytes to vascular surfaces is a critical component of the inflammatory response and is part of a complex series of reactions involving the simultaneous and interrelated activation of the complement, coagulation, and immune systems.

The complement proteins collectively play a leading role in the immune system, both in the identification and in the removal of foreign substances and immune complexes, as reviewed by Muller-Eberhard, H. J., Ann. Rev. Biochem. 57: 321–347 (1988). Central to the complement system are the C3 and C4 proteins, which when activated covalently attach to nearby targets, marking them for clearance. In order to help control this process, a remarkable family of soluble and membrane-bound regulatory proteins has evolved, each of which interacts with activated C3 and/or C4 derivatives. The coagulation and inflammatory pathways are regulated in a coordinate fashion in response to tissue damage. For example, in addition to becoming adhesive for leukocytes, activated endothelial cells express tissue factor on the cell surface and decrease their surface expression of thrombomodulin, leading to a net facilitation of coagulation reactions on the cell surface. In some cases, a single receptor can be involved in both inflammatory and coagulation processes.

Leukocyte adherence to vascular endothelium is a key initial step in migration of leukocytes to tissues in response to microbial invasion. A class of inducible leukocyte receptors, the CD11–CD18 molecules (integrins), have a role in adherence to endothelium. These molecules are involved in mechanisms of leukocyte adherence involving inducible changes in the endothelium itself.

Activated platelets have also been shown to interact with both neutrophils and monocytes in vitro. The interaction of platelets with monocytes may be mediated in part by the binding of thrombospondin to platelets and monocytes, although other mechanisms have not been excluded. The mechanisms for the binding of neutrophils to activated platelets are not well understood, except that it is known that divalent cations are required. In response to vascular injury, platelets are known to adhere to subendothelial surfaces, become activated, and support coagulation. Platelets and other cells may also play an important role in the recruitment of leukocytes into the wound in order to contain microbial invasion.

Endothelium exposed to "rapid" activators such as thrombin and histamine becomes adhesive for neutrophils within two to ten minutes, while endothelium exposed to cytokines such as tumor necrosis factor and interleukin-1 becomes adhesive after one to six hours. The rapid endothelial-dependent leukocyte adhesion has been associated with expression of the lipid mediator platelet activating factor (PAF) on the cell surface, and presumably, the appearance of other endothelial surface receptors. The slower cytokine-inducible endothelial adhesion for leukocytes is mediated, at least in part, by E-selectin and ICAM-1 that are synthesized by endothelial cells after exposure to cytokines and then transported to the cell surface, where they bind neutrophils.

The isolation, characterization and cloning of E-selectin or ELAM-1 is reviewed by Bevilacqua, et al., in Science 243, 1160–1165 (1989). L-selectin, a peripheral lymph node homing receptor, also called "the murine Mel 14 antigen", "Leu 8", the "Leu 8 antigen" and "LAM-1", is another structure on neutrophils, monocytes, and lymphocytes that binds lymphocytes to high endothelial venules in peripheral lymph nodes. The characterization and cloning of the protein is reviewed by Lasky, et al., Cell 56, 1045–1055 (1989) (mouse) and Tedder, et al., J. Exp. Med. 170, 123–133 (1989).

P-selectin, also known as GMP-140 (granule membrane protein 140), or PADGEM, is a cysteine-rich and heavily glycosylated integral membrane glycoprotein with an apparent molecular weight of 140,000 as assessed by sodium dodecyl sulfate polyacrylamide gel electrophoresis (SDS-PAGE). P-selectin was first purified from human platelets by McEver and Martin, J. Biol. Chem. 259: 9799–9804 (1984). The protein is present in alpha granules of resting platelets but is rapidly redistributed to the plasma membrane following platelet activation, as reported by Stenberg, et al., (1985). The presence of P-selectin in endothelial cells and its biosynthesis by these cells was reported by McEver, et al., Blood 70(5) Suppl. 1:355a, Abstract No. 1274 (1987). In endothelial cells, P-selectin is found in storage granules known as the Weibel-Palade bodies. (McEver, et al. J. Clin. Invest. 84: 92–99 (1989) and Hattori, et al., J. Biol. Chem. 264. 7768–7771 (1989)). P-selectin (called GMP-140 or PADGEM) has also been reported to mediate the interaction of activated platelets with neutrophils and monocytes by Larsen, et al., in Cell 59, 305–312 (October 1989) and Hamburger and McEver, Blood 75: 550–554 (1990).

The cDNA-derived amino acid sequence, reported by Johnston, et al., in Cell 56, 1033–1044 (Mar. 24, 1989), and in U.S. Ser. No. 07/320,408 filed Mar. 8, 1989, indicates that it contains a number of modular domains that are likely to fold independently. Beginning at the N-terminus, these include a "lectin" domain, an "EGF" domain, nine tandem consensus repeats similar to those in complement binding proteins, a transmembrane domain (except in a soluble form that appears to result from differential splicing), and a cytoplasmic tail.

When platelets or endothelial cells are activated by mediators such as thrombin, the membranes of the storage granules fuse with the plasma membrane, the soluble contents of the granules are released to the external environment, and membrane bound P-selectin is presented within seconds on the cell surface. The rapid redistribution of P-selectin to the surface of platelets and endothelial cells as a result of activation suggested that this glycoprotein could play an important role at sites of inflammation or vascular disruption.

This important role has been confirmed by the observation that P-selectin is a receptor for neutrophils (Geng et al., Nature 343:757–760 (1990); Hamburger and McEver, Blood 75:550–554 (1990)), monocytes (Larsen, et al. Cell 59:305–312 (1989)); Moore, et al., J. Cell Biol. 112:491–499 (1991)), and perhaps a subset of lymphocytes (Moore, et al. J. Cell Biol. 112:491–499 (1991)). Thus, GMP-140 can serve as a receptor for leukocytes following its rapid mobilization to the surfaces of platelets and endothelial cells stimulated with agonists such as thrombin. This role in leukocyte recruitment may be important in hemostatic and inflammatory processes in both physiologic and pathologic states.

Peptides derived from P-selectin are described in U.S. Ser. No. 07/554,199 entitled "Functionally Active Selectin- Derived Peptides" filed Jul. 17, 1990 by Rodger P. McEver that are useful in diagnostics and in modulating the hemostatic and inflammatory responses in a patient wherein a therapeutically effective amount of a peptide capable of blocking leukocyte recognition of P-selectin is administered to the patient. U.S. Ser. No. 07/554,199 filed Jul. 17, 1990 also discloses that peptide sequences within the lectin domain of P-selectin, having homology with the lectin domains of other proteins, especially E-selectin and the L-selectin, selectively inhibit neutrophil adhesion to purified P-selectin, and can therefore be used in diagnostic assays of patients and diseases characterized by altered binding by these molecules, in screening assays for compounds altering this binding, and in clinical applications to inhibit or modulate interactions of leukocytes with platelets or endothelial cells involving coagulation and/or inflammatory processes.

In Ser. No. 07/757,131, "Peptide Inhibitors of Inflammation Mediated By Selectins", George A. Heavner, et al., peptides corresponding to the 56–60 sequence of the selectins (P-selectin, E-selectin and L-selectin) were disclosed as compounds that will inhibit selectin dependent cell adhesion. Analogs of these sequences having similar activity were also disclosed.

E-selectin, L-selectin, and P-selectin have been termed "selectins", based on their related structure and function. E-selectin is not present in unstimulated endothelium. However, when endothelium is exposed to cytokines such as tumor necrosis factor of interleukin-1, the gene for E-selectin is transcribed, producing RNA which in turn is translated into protein. The result is that E-selectin is expressed on the surface of endothelial cells one to four hours after exposure to cytokines, as reported by Bevilacqua et al., *Proc. Natl. Acad. Sci. USA* 84: 9238–9242 (1987) (in contrast to P-selectin, which is stored in granules and presented on the cell surface within seconds after activation). E-selectin has been shown to mediate the adherence of neutrophils to cytokine-treated endothelium and thus appears to be important in allowing leukocytes to migrate across cytokine-stimulated endothelium into tissues. The cDNA-derived primary structure of E-selectin indicates that it contains a "lectin" domain, an EGF domain, and six instead of the nine in P-selectin) repeats similar to those of complement-regulatory proteins, a transmembrane domain, and a short cytoplasmic tail. There is extensive sequence homology between P-selectin and E-selectin throughout both proteins, but the similarity is particularly striking in the lectin and EGF domains. ICAM-1 expression on the surface of endothelial cells begins several hours following stimulation and reaches maximal levels at from between five and 24 hours.

Homing receptors are lymphocyte surface structures that allow lymphocytes to bind to specialized endothelial cells in lymphatic tissues, termed high endothelial cells or high endothelial venules (reviewed by Yednock and Rose, *Advances in Immunology*, vol. 44, F. I. Dixon, ed., 313–378 (Academic Press, New York 1989). This binding allows lymphocytes to migrate across the endothelium into the lymphatic tissues where they are exposed to processed antigens. The lymphocytes then re-enter the blood through the lymphatic system. L-selectin, a lymphocyte homing receptor, contains a lectin domain, an EGF domain, two complement-binding repeats, a transmembrane domain, and a short cytoplasmic tail. L-selectin also shares extensive sequence homology with P-selectin, particularly in the lectin and EGF domains.

Based on a comparison of the lectin domains between P-selectin, E-selectin, and L-selectin, it may be possible to select those peptides inhibiting binding of neutrophils to P-selectin which will inhibit binding of E-selectin, L-selectin, and other homologous selecting, to components of the inflammatory process, or, conversely, which will inhibit only P-selectin binding.

The recruitment and movement of leukocytes is regulated by several molecules. The selectins are involved in early stages of recruitment. The integrins and Ig superfamily molecules, for example ICAM-1, are also involved in this process. It has been demonstrated by M. L. Dustin et al., in *J. Immunol.* 137, 245–254 (1986) that ICAM-1, a member of the Ig superfamily that recognizes members of the integrin family on leukocytes, can be induced on the surface of endothelial cells by stimulation with IL-1.

The in vivo significance of platelet-leukocyte interactions has not been studied carefully. However, in response to vascular injury, platelets are known to adhere to subendothelial surfaces, become activated, and support coagulation. Platelets and other cells may also play an important role in the recruitment of leukocytes into the wound in order to contain microbial invasion. Conversely, leukocytes may recruit platelets into tissues at sites of inflammation, as reported by Issekutz, et al., *Lab. Invest.* 49:716 (1983).

The coagulation and inflammatory pathways are regulated in a coordinate fashion in response to tissue damage. For example, in addition to becoming adhesive for leukocytes, activated endothelial cells express tissue factor on the cell surface and decrease their surface expression of thrombomodulin, leading to a net facilitation of coagulation reactions on the cell surface. In some cases, a single receptor can be involved in both inflammatory and coagulation processes.

Proteins involved in the hemostatic and inflammatory pathways are of interest for diagnostic purposes and treatment of human disorders. However, there are many problems using proteins therapeutically. Proteins are usually expensive to produce in quantities sufficient for administration to a patient. Moreover, there can be a reaction against the protein after it has been administered more than once to the patient. It is therefore desirable to develop peptides having the same, or better, activity as the protein, which are inexpensive to synthesize, reproducible and relatively innocuous.

It is preferable to develop peptides which can be prepared synthetically, having activity at least equal to, or greater than, the peptides derived from the protein itself.

It is therefore an object of the present invention to provide peptides interacting with cells recognized by selectins, including P-selectin, E-selectin, L-selectin, and ICAM-1.

It is another object of the present invention to provide methods for using these peptides to inhibit leukocyte adhesion to endothelium or to platelets.

It is a further object of the present invention to provide methods for using these peptides to modulate the immune response and the hemostatic pathway.

It is yet another object of the present invention to provide peptides for use in diagnostic assays relating to P-selectin, E-selectin, L-selectin and ICAM-1.

SUMMARY OF THE INVNETION

It has now been found that cyclic peptides of the selectin 54–63 sequence exhibit unexpected and desired properties. Specific points of cyclization or conformational restriction in conjunction with specific substitutions have been identified that not only unexpectedly enhance the biological activity of these compounds, but also significantly increase their resistance to enzymatic degradation. The unique nature of these structures and enhancement of activity and stability is shown by the fact that not all cyclic structures that can be generated involving the 54–63 selectin sequence are active. To illustrate this point, cyclic structures involving cyclization between amino acids at position 59 and 63 lead to total loss of biological activity. Two examples illustrative of this inactive series are Arg-Lys-Ile-Gly-Gly-cyclo(Lys-Trp-Thr-Trp-Glu)-NH$_2$ (SEQ ID NO:1) and Arg-Lys-Ile-Gly-Gly-cyclo(Glu-Trp-Thr-Trp-Lys)-NH$_2$ (SEQ ID NO:2).

To further demonstrate the uniqueness of the active cyclic peptides, the 56–59 cyclic structure Arg-Lys-cyclo(Asp-Gly-Gly-Dap)-Trp-Thr-Trp-Val-NH$_2$ (SEQ ID NO:3) where Dap is L-diaminopropionic acid and the cyclization is an amide bond and Asp$^{56}$ and Dap$^{59}$ is totally inactive in inhibiting neutrophil adhesion to P-selectin; however, the closely related compound Arg-Lys-cyclo(Dap-Gly-Gly-Asp)-Trp-Thr-Trp-Val-NH$_2$ (SEQ ID NO:4), which is equivalent to the reversal of the amide bond with no change in ring size or relative amide bond position to the rest of the molecule, is active at 13 mM in inhibiting neutrophil adhesion to P-selectin. These latter two compounds clearly demonstrate the act of forming a cyclic compound of 54–63 selectin analogs does not automatically convey retention or enhancement of activity, that ring size itself is not the sole determination of activity nor are the amino acids involved in the cyclization the sole determinant for retention of activity. The data from these two closely related compounds clearly demonstrates the uniqueness of the active compounds presented herein.

This invention relates to novel peptides selected from formulas I–XI:

Formula I

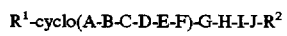

R$^1$-cyclo(A-B-C-D-E-F)-G-H-I-J-R$^2$ wherein:

A is D- or L-lysine, D- or L-glutamic acid, D- or L-aspartic acid, D- or L-ornithine, D- or L-diaminopropionic acid, D- or L-cystine, D- or L-homocystine or D- or L-penicillamine, B is D- or L-lysine, C is D- or L-isoleucine, D- or L-asparagine, D- or L-arginine or D- or L-valine, D is glycine, D- or L-asparagine, D- or L-phenylalanine, D- or L-proline or D- or L-alanine, E is glycine, D- or L-lysine, D- or L-asparagine, D- or L-phenylalanine, D- or L-tyrosine or D- or L-proline, or D and E taken together are an omega amino carboxylic acid of the formula NH$_2$—(CH2)$_n$—COOH where n=3 to 10, F is D- or L-lysine, D- or L-glutamic acid, D- or L-aspartic acid, D- or L-ornithine, D- or L-diaminopropionic acid, D- or L-cystine, D- or L-homocystine or D- or L-penicillamine, chosen such that if A is a thio-containing amino acid then F is a thio containing amino acid and the link between A and F is a disulfide or thioether bond, if A is a dicarboxylic amino acid then F is a diamino acid and the link between A and F is an amide bond and if A is a diamino acid then F is a dicarboxylic acid and the link between A and F is an amide bond, G is D- or L-tryptophan or D- or L-phenylalanine, H is D- or L-threonine, D-threonyl-D-glutaminyl, D-threonyl-glutaminyl, threonyl-D-glutaminyl or threonyl-glutaminyl, I is D- or L-tryptophan, or D- or L-threonyl, J is D- or L-valine, D- or L-alanine, D- or L-leucine, D- or L-isoleucine or null (signifying no amino acid as this position), R$^1$ is acyl, aroyl, alkyloxycarbonyl, aryloxycarbonyl, H (signifying a free N-terminal amino group) or desamino (signifying that the N-terminal amino group was replaced by a hydrogen and the α-carbon of A is no longer an asymmetric center) and R$^2$ is OH (signifying a C-terminal carboxylic acid), OR$^3$ where R$^3$ is lower alkyl or aryl, or NR$^4$R$^5$ where R$^4$ and R$^5$ are independently selected from H, lower alkyl, cycloalkyl or aryl or taken together constitute a methylene chain.

Formula II

R$^1$-cyclo(K-L-M-N-P-Q-R-S-T-U)-R$^2$ wherein:

K is D- or L-lysine, D- or L-glutamic acid, D- or L-aspartic acid, D- or L-ornithine, D- or L-diaminopropionic acid, D- or L-cystine, D- or L-homocystine or D- or L-penicillamine, L is D- or L-lysine, M is D- or L-isoleucine, D- or L-asparagine, D- or L-arginine or D- or L-valine, N is glycine, D- or L-asparagine, D- or L-phenylalanine, D- or L-proline or D- or L-alanine, P is glycine, D- or L-lysine, D- or L-asparagine, D- or L-phenylalanine, D- or L-tyrosine or D- or L-proline, or N and P taken together are an omega amino carboxylic acid of the formula NH$_2$—(CH2)$_n$—COOH where n=3 to 10, Q is D- or L- isoleucine, D- or L-threonine or D- or L-valine, R is D- or L-tryptophan or D- or L-phenylalanine, S is D- or L-threonine, D-threonyl-D-glutaminyl, D-threonyl-glutaminyl, threonyl-D-glutaminyl or threonyl-glutaminyl, T is D- or L-tryptophan, or D- or L-threonyl, U is D- or L-lysine, D- or L-glutamic acid, D- or L-aspartic acid, D- or L-ornithine, D- or L-diaminopropionic acid, D- or L-cystine, D- or L-homocystine or D- or L-penicillamine, chosen such that if K is a thio-containing amino acid then U a this containing amino acid and the link between K and U is a disulfide or thioether bond, if K is a dicarboxylic amino acid then U is a diamino acid and the link between K and U is an amide bond and if K is a diamino acid then U is a dicarboxylic acid and the link between K and U is an amide bond, R$^1$ is acyl, aroyl, alkyloxycarbonyl, aryloxycarbonyl, H (signifying a free N-terminal amino group) or desamino (signifying that the N-terminal amino group was replaced by a hydrogen and the α-carbon of K is no longer an asymmetric center) and R$^2$ is OH (signifying a C-terminal carboxylic acid), OR$^3$ where R$^3$ is lower alkyl or aryl, or NR$^4$R$^5$ where R$^4$ and R$^5$ are independently selected from H, lower alkyl, cycloalkyl or aryl or taken together constitute a methylene chain.

Formula III

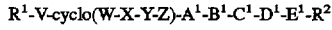

R$^1$-V-cyclo(W-X-Y-Z)-A$^1$-B$^1$-C$^1$-D$^1$-E$^1$-R$^2$ wherein:
V is D- or L-arginine or null (signifying no amino acid at this position),
W is D- or L-lysine, D- or L-glutamic acid, D- or L-aspartic acid, D- or L-ornithine, D- or L-diaminopropionic acid, D- or L-cystine, D- or L-homocystine or D- or L-penicillamine,
X is D- or L-isoleucine, D- or L-asparagine, D- or L-arginine or D- or L-valine,
Y is glycine, D- or L-asparagine, D- or L-phenylalanine, D- or L-proline or D- or L-alanine,
Z is D- or L-lysine, D- or L-glutamic acid, D- or L-aspartic acid, D- or L-ornithine, D- or L-diaminopropionic acid, D- or L-cystine, D- or L-homocystine or D- or L-penicillamine, chosen such that if W is a thio-containing amino acid then Z is a thio containing amino acid and the link between W and Z is a disulfide or thioether bond, if W is a dicarboxylic amino acid then Z is a diamino acid and the link between W and Z is an amide bond and if W is a diamino acid then Z is a dicarboxylic acid and the link between W and Z is an amide bond,
$A^1$ is D- or L-isoleucine, D- or L-threonine or D- or L-valine,
$B^1$ is D- or L-tryptophan or D- or L-phenylalanine,
$C^1$ is D- or L-threonine, D-threonyl-D-glutaminyl, D-threonyl-glutaminyl, threonyl-D-glutaminyl or threonyl-glutaminyl,
$D^1$ is D- or L-tryptophan, or D- or L-threonyl,
$E^1$ is D- or L-valine, D- or L-alanine, D- or L-leucine, D- or L-isoleucine or null (signifying no amino acid at this position),
$R^1$ is acyl, aroyl, alkyloxycarbonyl, aryloxycarbonyl, H (signifying a free N-terminal amino group) or desamino (signifying that the N-terminal amino group was replaced by a hydrogen and the α-carbon of V is no longer an asymmetric center) and
$R^2$ is OH (signifying a C-terminal carboxylic acid), $OR^3$ where $R^3$ is lower alkyl or aryl, or $NR^4R^5$ where $R^4$ and $R^5$ are independently selected from H, lower alkyl, cycloalkyl or aryl or taken together constitute a methylene chain.

Formula IV

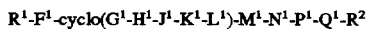

wherein:
$F^1$ is D- or L-arginine, D- or L-lysine or null (signifying no amino acid at this position),
$G^1$ is D- or L-lysine, D- or L-glutamic acid, D- or L-aspartic acid, D- or L-ornithine, D- or L-diaminopropionic acid, D- or L-cystine, D- or L-homocystine or D- or L-penicllamine,
$H^1$ is D- or L-isoleucine, D- or L-asparagine, D- or L-arginine or D- or L-valine,
$J^1$ is glycine, D- or L-asparagine, D- or L-phenylalanine, D- or L-proline or D- or L-alanine,
$K^1$ is glycine, D- or L-lysine, D- or L-asparagine, D- or L-phenylalanine, D- or L-tyrosine or D- or L-proline, or
$J^1$ and $K^1$ taken together are an omega amino carboxylic acid of the formula $NH_2$—$(CH_2)_n$—COOH where n=3 to 10,
$L^1$ is D- or L-lysine, D- or L-glutamic acid, D- or L-aspartic acid, D- or L-ornithine, D- or L-diaminopropionic acid, D- or L-cystine, D- or L-homocystine or D- or L-penicillamine, chosen such that if $G^1$ is a thio-containing amino acid then $L^1$ is a thio containing amino acid and the link between $G^1$ and $L^1$ is a disulfide or thioether bond, if $G^1$ is a dicarboxylic amino acid then $L^1$ is a diamino acid and the link between $G^1$ and $L^1$ is an amide bond and if $G^1$ is a diamino acid then $L^1$ is a dicarboxylic acid and the link between $G^1$ and $L^1$ is an amide bond,
$M^1$ is D- or L-tryptophan or D- or L-phenylalanine,
$N^1$ is D- or L-threonine, D-threonyl-D-glutaminyl, D-threonyl-glutaminyl, threonyl-D-glutaminyl or threonyl-glutaminyl,
$P^1$ is D- or L-tryptophan, or D- or L-threonyl,
$Q^1$ is D- or L-valine, D- or L-alanine, D- or L-leucine, D- or L-isoleucine or null (signifying no amino acid as this position),
$R^1$ is acyl, aroyl, alkyloxycarbonyl, aryloxycarbonyl, H (signifying a free N-terminal amino group) or desamino (signifying that the N-terminal amino group was replaced by a hydrogen and the α-carbon of $F^1$ is no longer an asymmetric center) and
$R^2$ is OH (signifying a C-terminal carboxylic acid), $OR^3$ where $R^3$ is lower alkyl or aryl, or $NR^4R^5$ where $R^4$ and $R^5$ are independently selected from H, lower alkyl, cycloalkyl or aryl or taken together constitute a methylene chain.

Formula V

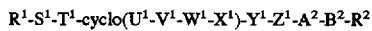

wherein:
$S^1$ is D- or L-arginine, D- or L-aspartic acid or null (signifying no amino acid at this position),
$T^1$ is D- or L- arginine, D- or L-lysine, D- or L-alanine, D- or L-glutamine, D- or L-glutamic acid or null (signifying no amino acid at this position),
$U^1$ is D- or L-lysine, D- or L-glutamic acid, D- or L-aspartic acid, D- or L-ornithine, D- or L-diaminopropionic acid, D- or L-cystine, D- or L-homocystine or D- or L-penicillamine,
$V^1$ is glycine, D- or L-asparagine, D- or L-phenylalanine, D- or L-proline, D- or L-alanine, D- or L-arginine, D- or L- β-alanine, D- or L-histidine, D- or L-isoleucine, D- or L-glycine, D- or L-lysine, D- or L-cysteine, D- or L-glutamine, or D- or L-leucine;
$W^1$ is glycine, D- or L-lysine, D- or L-asparagine, D- or L-phenylalanine, D- or L-tyrosine, D- or L-proline, D- or L-3,4-dehydro proline, D- or L- alanine, D- or L-arginine, D- or L-aspartic acid, D- or L-isoleucine, D- or L-leucine, D- or L-thio-proline, D- or L- tetrahydroisoquinolinecarboxylic acid, D- or L-tryptophan, D- or L-glutamine, D- or L-glutamic acid, D- or L-N-methyl-phenylalanine, D- or L- naphthyl-alanine, D- or L-valine, or D- or L-p-Cl-phenylalanine, or
$V^1$ and $W^1$ taken together are an omega amino carboxylic acid of the formula $NH_2$—$(CH_2)_n$—COOH where n=3 to 10,
$X^1$ is D- or L-lysine, D- or L-glutamic acid, D- or L-aspartic acid, D- or L-ornithine, D- or L-diaminopropionic acid, D- or L-cystine, D- or L-homocystine or D- or L-penicillamine, chosen such that if $U^1$ is a thio-containing amino acid then $X^1$ is a thio containing amino acid and the link between $U^1$ and $X^1$ is a disulfide bond, if $U^1$ is a dicarboxylic amino acid then $X^1$ is a diamino acid and the link between $U^1$ and $X^1$ is an amide bond and if $U^1$ is a diamino acid then $X^1$ is a dicarboxylic acid and the link between $U^1$ and $X^1$ is an amide bond, $Y^1$ is D- or L-tryptophan, D- or L-phenylalanine, D- or L-glytamine, D- or L-histidine, D- or L-acetyl-lysine, D- or L-napthyl-analine, D- or L-lysine, D- or L-tyrosine, D- or L-valine or D- or L-proline, $Z^1$ is D- or L-threonine, D- or L-valine, D-threonyl-D-glutaminyl, D-threonyl-glutaminyl, threonyl-D-glutaminyl or threonyl-glutaminyl, $A^2$ is D- or L-tryptophan, D- or L-threonyl, D- or L-histidine, D- or L-lysine, D- or L-tyrosine, D- or L-proline, D- or L-naphthyl-alanine, D- or L-phenylalanine, D- or L-arginine, or D- or L-glutamine, $B^2$ is D- or L-valine, D- or L-alanine, D- or L-leucine, D- or L-isoleucine, D- or L-tryptophan, D- or L-glutamine or null (signifying no amino acid at this position), $R^1$ is acyl, aroyl, alkyloxycarbonyl, aryloxycarbonyl, H (signifying a free N-terminal amino group) or desamino (signifying that the N-terminal amino group was replaced by a hydrogen and the $\alpha$-carbon of $S^1$ is no longer an asymmetric center) and $R^1$ is OH (signifying a C-terminal carboxylic acid), $OR^3$ where $R^3$ is lower alkyl or aryl, or $NR^4 R^5$ where $R^4$ and $R^5$ are independently selected from H, lower alkyl, cycloalkyl or aryl or taken together constitute a methylene chain.

Formula VI

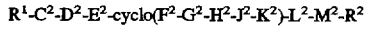

wherein:

$C^2$ is D- or L-arginine or null (signifying no amino acid at this position), $D^2$ is D- or L-arginine, D- or L-lysine or null (signifying no amino acid at this position), $E^2$ is D- or L-isoleucine, D- or L-asparagine, D- or L-arginine or D- or L-valine, $F^2$ is D- or L-lysine, D- or L-glutamic acid, D- or L-aspartic acid, D- or L-ornithine, D- or L-diaminopropionic acid, D- or L-cystine, D- or L-homocystine or D- or L-penicillamine, $G^2$ is glycine, D- or L-lysine, D- or L-asparagine, D- or L-phenylalanine, D- or L-tyrosine or D- or L-proline, $H^2$ is D- or L-isoleucine, D- or L-threonine or D- or L-valine, $J^2$ is D- or L-tryptophan or D- or L-phenylalanine, $K^2$ is D- or L-lysine, D- or L-glutamic acid, D- or L-aspartic acid, D- or L-ornithine, D- or L-diaminopropionic acid, D- or L-cystine, D- or L-homocystine or D- or L-penicillamine, chosen such that if $F^2$ is a thio-containing amino acid then $K^2$ is a thio containing amino acid and the link between $F^2$ and $K^2$ is a disulfide or thioether bond, if $F^2$ is a dicarboxylic amino acid then $K^2$ is a diamino acid and the link between $F^2$ and $K^2$ is an amide bond and if $F^2$ is a diamino acid then $K^2$ is a dicarboxylic acid and the link between $F^2$ and $K^2$ is an amide bond, $L^2$ is D- or L-tryptophan, or D- or L-threonyl, $M^2$ is D- or L-valine, D- or L-alanine, D- or L-leucine, D- or L-isoleucine or null (signifying no amino acid at this position), $R^1$ is acyl, aroyl, alkyloxycarbonyl, aryloxycarbonyl, H (signifying a free N-terminal amino group) or desamino (signifying that the N-terminal amino group was replaced by a hydrogen and the $\alpha$-carbon of $C^2$ is no longer an asymmetric center) and $R^2$ is OH (signifying a C-terminal carboxylic acid), $OR^3$ where $R^3$ is lower alkyl or aryl, or $NR^4 R^5$ where $R^4$ and $R^5$ are independently selected from H, lower alkyl, cycloalkyl or aryl or taken together constitute a methylene chain.

Formula VII

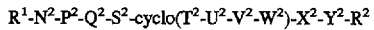

wherein:

$N^2$ is D- or L-arginine or null (signifying no amino acid at this position), $P^2$ is D- or L-arginine, D- or L-lysine or null (signifying no amino acid at this position), $Q^2$ is D- or L-isoleucine, D- or L-asparagine, D- or L-arginine or D- or L-valine, $S^2$ is glycine, D- or L-asparagine, D- or L-phenylalanine, D- or L-proline or D- or L-alanine, $T^2$ is D- or L-lysine, D- or L-glutamic acid, D- or L-aspartic acid, D- or L-ornithine, D- or L-diaminopropionic acid, D- or L-cystine, D- or L-homocystine or D- or L-penicillamine, $U^2$ is D- or L-isoleucine, D- or L-threonine or D- or L-valine, $V^2$ is D- or L-tryptophan or D- or L-phenylalanine, $W^2$ is D- or L-lysine, D- or L-glutamic acid, D- or L-aspartic acid, D- or L-ornithine, D- or L-diaminopropionic acid, D- or L-cystine, D- or L-homocystine or D- or L-penicillamine, chosen such that if $T^2$ is a thio-containing amino acid then $W^2$ is a thio containing amino acid and the link between $T^2$ and $W^2$ is a disulfide or thioether bond, if $T^2$ is a dicarboxylic amino acid then $W^2$ is a diamino acid and the link between $T^2$ and $W^2$ is an amide bond and if $T^2$ is a diamino acid then $W^2$ is a dicarboxylic acid and the link between $T^2$ and $W^2$ is an amide bond, $X^2$ is D- or L-tryptophan, or D- or L-threonyl, $Y^2$ is D- or L-valine, D- or L-alanine, D- or L-leucine, D- or L-isoleucine or null (signifying no amino acid at this position), $R^1$ is acyl, aroyl, alkyloxycarbonyl, aryloxycarbonyl, H (signifying a free N-terminal amino group) or desamino (signifying that the N-terminal amino group was replaced by a hydrogen and the $\alpha$-carbon of $N^2$ is no longer an asymmetric center and $R^2$ is OH (signifying a C-terminal carboxylic acid), $OR^3$ where $R^3$ is lower alkyl or aryl, or $NR^4R^5$ where $R^4$ and $R^5$ are independently selected from H, lower alkyl, cycloalkyl or aryl or taken together constitute a methylene chain.

Formula VIII

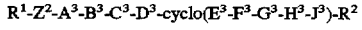

wherein at:

$Z^2$ is D- or L-arginine or null (signifying no amino acid at this position), $A^3$ is D- or L-arginine, D- or L-lysine or null (signifying no amino acid at this position), $B^3$ is D- or L-isoleucine, D- or L-asparagine, D- or L-arginine or D- or L-valine, $C^3$ is D- or L-isoleucine, D- or L-asparagine, D- or L-arginine or D- or L-valine, $D^3$ is glycine, D- or L-lysine, D- or L-asparagine, D- or L-phenylalanine, D- or L-tyrosine or D- or L-proline, or $C^3$ and $D^3$ taken together are an omega amino carboxylic acid of the formula $NH_2$—$(CH2)_n$—COOH where n=3 to 10, $E^3$ is D- or L-lysine, D- or L-glutamic acid, D- or L-aspartic acid, D- or L-ornithine, D- or L-diaminopropionic acid, D- or L-cystine, D- or L-homocystine or D- or L-penicillamine, $F^3$ is D- or L-tryptophan or D- or L-phenylalanine, $G^3$ is D- or L-threonine, D-threonyl-D-glutaminyl, D-threonyl-glutaminyl, threonyl-D-glutaminyl or threonyl-glutaminyl, $H^3$ is D- or L-tryptophan, or D- or L-threonyl, $J^3$ is D- or L-lysine, D- or L-glutamic acid, D- or L-aspartic acid, D- or L-ornithine, D- or L-diaminopropionic acid, D- or L-cystine, D- or L-homocystine or D- or L-penicillamine, chosen such that if $E^3$ is a thio-containing amino acid then $J^3$ is a thio containing amino acid and the link between $E^3$ and $J^3$ is a disulfide or thioether bond, if $E^3$ is a dicarboxylic amino acid then $J^3$ is a diamino acid and the link between $E^3$ and $J^3$ is an amide bond and if $E^3$ is a diamino acid then $J^3$ is a dicarboxylic acid and the link between $E^3$ and $J^3$ is an amide bond, $R^1$ is acyl, aroyl, alkyloxycarbonyl, aryloxycarbonyl, H (signifying a free N-terminal amino group) or desamino (signifying that the N-terminal amino group was replaced by a hydrogen and the α-carbon of $Z^2$ is no longer an asymmetric center) and $R^2$ is OH (signifying a C-terminal carboxylic acid), $OR^3$ where $R^3$ is lower alkyl or aryl, or $NR^4 R^5$ where $R^4$ and $R^5$ are independently selected from H, lower alkyl, cycloalkyl or aryl or taken together constitute a methylene chain.

Formulas IX and X

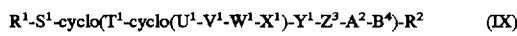
$$R^1\text{-}S^1\text{-cyclo}(T^1\text{-cyclo}(U^1\text{-}V^1\text{-}W^1\text{-}X^1)\text{-}Y^1\text{-}Z^3\text{-}A^2\text{-}B^4)\text{-}R^2 \quad (IX)$$

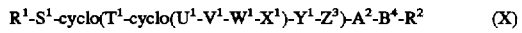
$$R^1\text{-}S^1\text{-cyclo}(T^1\text{-cyclo}(U^1\text{-}V^1\text{-}W^1\text{-}X^1)\text{-}Y^1\text{-}Z^3)\text{-}A^2\text{-}B^4\text{-}R^2 \quad (X)$$

where $R^1, S^1, T^1, U^1, V^1, W^1, X^1, Y^1, A^2$, and $R^2$ are as defined above for Formula V, and where $Z^3$ is D- or L-threonine, D- or L-valine, D-threonyl-D-glutaminyl, D-threonyl-glutaminyl, threonyl-D-glutaminyl or threonyl-glutaminyl, or D- or L-glutamic acid; and $B^4$ is D- or L-valine, D- or L-alanine, D- or L-leucine, D- or L-isoleucine, D- or L-tryptophan, D- or L-glutamine, D- and L-glutamic acid, or null (signifying no amino acid at this position).

Formula XI

$$R^1\text{-cyclo}(A^5\text{-}B^5\text{-}C^5\text{-}D^5)\text{-}E^5\text{-}F^5\text{-}G^5\text{-}H^5\text{-}I^5 J^5\text{-}R^2 \quad (XI)$$

where $R^1$ and $R^2$ are as defined above, $A^5$ is D- or L-cysteine, $B^5$ is D- or L-lysine, $C^5$ is D- or L-isoleucine, $D^5$ is D- or L-cysteine, $E^5$ is D- or L-glycine, $F^5$ is D- or L-isoleucine, $G^5$ is D- or L-tryptophan, $H^5$ is D- or L-threonine, $I^5$ is D- or L-tryptophan, and $J^5$ is D- or L-valine.

Peptides of Formula I–XI have as their core region portions of the 54–63 amino acid sequences of the selectins, with residue 1 defined as the N-terminus of the mature proteins after the cleavage of the signal peptides.

We have made the observation that peptides derived from the selectins can also inhibit ICAM-1 dependent adhesion. Compounds with this ability to broadly inhibit molecules involved in leukocyte binding may offer advantages by modulating multiple adhesion pathways.

Tests indicate that the peptides of Formulas I–XI inhibit the binding of neutrophils to P-selectin in concentrations of peptide ranging from about 0.3 to about 1000 μM and to stimulated HUVEC cells at concentrations of peptide ranging from about 30 to about 1000 μM. Tests also indicate that alterations within the core sequence, including the addition or deletion of amino acids, do not result in loss of biological activity. Table I gives the $IC_{50}$ values in mM for peptides of Formulas I–XI in inhibiting the binding of human neutrophils to P-selectin.

This invention relates not only to the novel peptides of Formulas I–XI, but also to pharmaceutical compositions comprising them, to diagnostic and therapeutic methods utilizing them, and to methods of preparing them.

BRIEF DESCRIPTION OF THE DRAWINGS

FIG. I shows a peptide of Formula V to inhibit the adhesion of human neutrophils to purified human P-selectin. FIG. I also shows peptides of the native sequence of P-selectin 23–30-amide, 54–63-amide and 70–79-amide to inhibit the adhesion of human neutrophils to purified human P-selectin, but requiring a higher dose than the peptide of Formula V.

FIG. II shows peptides of Formula V to inhibit the adhesion of human neutrophils to HUVEC cells stimulated for 19 hr by IL-1, adhesion known to be ICAM-1 dependent. Antibody controls in FIG. II confirm that the adhesion is ICAM-1 dependent and not E-selectin dependent.

FIG. III shows the inhibition of neutrophil influx in response to rk-cyclo(cGFc)-wtwv-$NH_2$ in a rat model of thioglycolate-induced peritonitis. Controls are peritoneal thioglycolate without peptide and peritoneal saline without peptide.

FIG. IV shows the chemical structure of one of the cyclic peptides of this invention, cyclo(Glu-Lys-Ile-Gly-Gly-Lys)-Trp-Thr-Trp-Val-$NH_2$ (Peptide (1) (SEQ ID NO:5)).

DETAILED DESCRIPTION OF THE INVENTION

Preferred peptides of this invention are those of Formulas I–XI wherein, $R^1$ is H and $R^2$ is $NH_2$.

Representative examples of specifically preferred peptides include the following "Preferred peptides" numbered (1)–(33):

Formula I:

(1) (SEQ ID NO:5) cyclo(Glu—Lys—Ile—Gly—Gly—Lys)—Trp—Thr—Trp—Val—NH₂
(2) (SEQ ID NO:6) cyclo(Lys—Lys—Ile—Gly—Gly—Glu)—Trp—Thr—Trp—Val—NH₂

Formula II:

(3) (SEQ ID NO:7) cyclo(Cys—Lys—Ile—Gly—Gly—Ile—Trp—Thr—Trp—Cys)—NH₂

Formula III:

(4) D-Arg—cyclo(D-Cys-D-Ile—Gly—D-Cys)—D-Ile—D-Trp—D-Thr—D-Trp—D-Val—NH₂

Formula IV:

(5) (SEQ ID NO:8) Arg—cyclo(Cys—Ile—Gly—Gly—Cys)—Trp—Thr—Trp—Val—NH₂
(6) (SEQ ID NO:9) Cyclo(Cys—Arg—Gly—Gly—Cys)—Trp—Thr—Trp—Val—NH₂

Formula V:

(7) (SEQ ID NO:10) Arg—Lys-cyclo(Cys—Gly—Gly—Cys)—Trp—Thr—Trp—NH₂
(8) D-Arg—D-Lys-cyclo(D-Cys—Gly—Gly—D-Cys)—D-Trp—D-Thr—D-Trp—NH₂
(9) (SEQ ID NO:11) Arg—Lys-cyclo(Cys—Gly—Gly—Cys)—Trp—Thr—Trp—Val—NH₂
(10) (SEQ ID NO:12) Arg—Lys-cyclo(Cys—Gly—Gly—Pen)—Trp—Thr—Trp—Val—NH₂
(11) D-Arg—D-Lys-cyclo(D-Cys—D-Ala—Phe—D-Cys)—D-Trp—D-Thr—D-Trp—D-Val—NH₂
(12) D-Arg—D-Lys-cyclo(D-Cys—D-Phe—Gly—D-Cys)—D-Trp—D-Thr—D-Trp—D-Val—NH₂
(13) D-Arg—D-Lys-cyclo(D-Cys—Gly—D-Phe—D-Cys)—D-Trp—D-Thr—D-Trp—D-Val—NH₂
(14) D-Arg—D-Lys-cyclo(D-Cys—Gly—Gly—D-Cys)—D-Phe—D-Thr—D-Trp—D-Val—NH₂
(15) D-Arg—D-Lys-cyclo(D-Cys—D-Pro—Gly—D-Cys)—D-Trp—D-Thr—D-Trp—D-Val—NH₂
(16) D-Arg—D-Lys-cyclo(D-Cys—Gly—D-Pro—D-Cys)—D-Trp—D-Thr—D-Trp—D-Val—NH₂
(17) D-Arg—D-Lys-cyclo(D-Cys—Gly—Gly—D-Cys)—D-Trp—D-Thr—D-Gln—D-Trp—D-Val—NH₂
(18) D-Arg—D-Lys-cyclo(D-Cys—Phe—Gly—D-Cys)—D-Trp—D-Thr—D-Trp—D-Val—NH₂
(19) D-Arg—D-Lys-cyclo(D-Cys—Gly—Phe—D-Cys)—D-Trp—D-Thr—D-Trp—D-Val—NH₂
(20) D-Arg—D-Lys-cyclo(D-Cys—Gly—Pro—D-Cys)—D-Trp—D-Thr—D-Trp—D-Val—NH₂
(21) D-Arg—D-Lys-cyclo(D-Cys—Ava—D-Cys)—D-Trp—D-Thr—D-Trp—D-Val—NH₂
(22) (SEQ ID NO:4) Arg—Lys-cyclo(Dap—Gly—Gly—Asp)—Trp—Thr—Trp—Val—NH₂
(23) (SEQ ID NO:13) Arg—Lys-cyclo(Pen—Gly—Gly—Cys)—Trp—Thr—Trp—Val—NH₂
(24) (SEQ ID NO:14) Arg—Lys-cyclo(Pen—Gly—Gly—Pen)—Trp—Thr—Trp—Val—NH₂
(25) D-Arg—D-Lys-cyclo(D-Cys—Gly—Gly—D-Cys)—D-Trp—D-Thr—D-Trp—D-Val—NH₂
(26) D-Lys-cyclo(D-Cys—Gly—Gly—D-Cys)-D-Trp—D-Thr—D-Trp—D-Val—NH₂
(27) (SEQ ID NO:15) Lys-cyclo(Cys—Gly—Gly—Cys)—Trp—Thr—Trp—Val—NH₂
(28) Cyclo(D-Cys—Gly—Gly—D-Cys)—D-Trp—D-Thr—D-Trp—D-Val—NH₂
(29) (SEQ ID NO:16) Cyclo(Cys—Gly—Gly—Cys)—Trp—Thr—Trp—Val—NH₂
(34) D-Arg—Lys-cyclo(D-Cys—Gly—Phe—D-Cys)—D-Trp—D-Thr—D-Trp—D-Val—NH₂
(35) D-Arg—D-Lys-cyclo(Cys—Gly—Phe—D-Cys)—D-Trp—D-Thr—D-Trp—D-Val—NH₂
(36) D-Arg—D-Lys-cyclo(D-Cys—Gly—(3,4-dehydro-D-Pro)—D-Cys)—D-Trp—D-Thr—D-Trp—D-Val—NH₂
(37) D-Arg—D-Lys-cyclo(D-Cys—Ala—Phe—D-Cys)—D-Trp—D-Thr—D-Trp—D-Val—NH₂
(38) D-Arg—D-Lys-cyclo(D-Cys—Gly—Ala—D-Cys)—D-Trp—D-Thr—D-Trp—D-Val—NH₂
(39) D-Arg—D-Lys-cyclo(D-Cys—Arg—Phe—D-Cys)—D-Trp—D-Thr—D-Trp—D-Val—NH₂
(40) D-Arg—D-Lys-cyclo(D-Cys—Gly—Arg—D-Cys)—D-Trp—D-Thr—D-Trp—D-Val—NH₂
(41) D-Arg—D-Lys-cyclo(D-Cys—Gly—Asn—D-Cys)—D-Trp—D-Thr—D-Trp—D-Val—NH₂
(42) D-Arg—D-Lys-cyclo(D-Cys—Gly—Asp—D-Cys)—D-Trp—D-Thr—D-Trp—D-Val—NH₂
(43) D-Arg—D-Cys-cyclo(D-Cys-Beta-Ala—Phe—D-Cys)—D-Trp—D-Thr—D-Trp—D-Val—NH₂
(44) D-Arg—D-Lys-Cyclo(D-Cys—D-Ala—Phe—D-Cys)—D-Trp—D-Thr—D-Trp—D-Val—NH₂
(45) D-Arg—D-Lys-cyclo(D-Cys—D-Arg—Phe—D-Cys)—D-Trp—D-Thr—D-Trp—D-Val—NH₂
(46) D-Arg—D-Lys-cyclo(D-Cys—Gly—Phe—D-Cys)—D-Gln—D-Thr—D-Trp—D-Val—NH₂
(47) D-Arg—D-Lys-cyclo(D-Cys—D-His—Phe—D-Cys)—D-Trp—D-Thr—D-Trp—D-Val—NH₂
(48) D-Arg—D-Lys-cyclo(D-Cys—Gly—Phe—D-Cys)—D-His—D-Thr—D-Trp—D-Val—NH₂
(49) D-Arg—D-Lys-cyclo(D-Cys—Ile—Ile—D-Cys)—D-Trp—D-Thr—D-Trp—D-Val—NH₂
(50) D-Arg—D-Lys-cyclo-desthio(D-Cys—Gly—Phe—D-Cys)—(D-Acetyl-Lys)—D-Thr—D-Trp—D-Val—NH₂
(51) D-Arg—D-Lys-cyclo(D-Cys—Gly—Phe—D-Cys)—D-Nal—D-Thr—D-Trp—D-Val—NH₂
(52) D-Arg—D-Lys-cyclo(D-Cys—Gly—D-Ile—D-Cys)—D-Trp—D-Thr—D-Trp—D-Val—NH₂
(53) D-Arg—D-Lys-cyclo(D-Cys—Gly—D-Leu—D-Cys)—D-Trp—D-Thr—D-Trp—D-Val—NH₂
(54) D-Arg—D-Lys-cyclo(D-Cys—D-Lys—Phe—D-Cys)—D-Trp—D-Thr—D-Trp—D-Val—NH₂
(55) D-Arg—D-Lys-cyclo(D-Cys—Gly—D-Lys—D-Cys)—D-Trp—D-Thr—D-Trp—D-Val—NH₂
(56) D-Arg—D-Lys-cyclo(D-Cys—Gly—Phe—D-Lys)—D-Trp—D-Thr—D-Trp—D-Val—NH₂
(57) D-Arg—D-Lys-cyclo(D-Cys—D-Pro—Phe—D-Cys)—D-Trp—D-Thr—D-Trp—D-Val—NH₂
(58) D-Arg—D-Lys-cyclo(D-Cys—Gly—D-Tpro—D-Cys)—D-Trp—D-Thr—D-Trp—D-Val—NH₂
(59) D-Arg—D-Lys-cyclo(D-Cys—Gly—D-Tic—D-Cys)—D-Trp—D-Thr—D-Trp—D-Val—NH₂
(60) D-Arg—D-Lys-cyclo(D-Cys—Gly—Trp-D-Cys)—D-Trp—D-Thr—D-Trp—D-Val—NH₂
(61) D-Arg—D-Lys-cyclo(D-Cys—Gly—Phe—D-Cys)—D-Trp—D-Thr—D-His—D-Val—NH₂
(62) D-Arg—D-Lys—cyclo(D-Cys—Gly—Phe—D-Cys)—D-Trp—D-Thr—D-Lys—D-Val—NH₂
(63) D-Arg—D-Lys-cyclo(D-Cys—Gly—Phe—D-Cys)—D-Trp—D-Thr—D-Tyr—D-Val—NH₂
(64) D-Arg—D-Lys—cyclo(D-Cys—Gly—Phe—D-Cys)—D-Tyr—D-Thr—D-Trp—D-Val—NH₂
(65) D-Arg—D-Lys-cyclo(D-Cys—Gly—Gln—D-Cys)—D-Trp—D-Thr—D-Trp—D-Val—NH₂
(66) D-Arg—D-Lys—D-cyclo(D-Cys—Gly—Glu—D-Cys)—D-Trp—D-Thr—D-Trp—D-Val—NH₂
(67) D-Arg—D-Lys-cyclo(D-Cys—Ile—D-Ile—D-Cys)—D-Trp—D-Thr—D-Trp—D-Val—NH₂
(68) D-Arg—D-Lys-cyclo(D-Cys—Gly—Ile—D-Cys)—D-Trp—D-Thr—D-Trp—D-Val—NH₂
(69) D-Arg—D-Lys-cyclo(D-Cys—Gly—Leu—D-Cys)—D-Trp—D-Thr—D-Trp—D-Val—NH₂
(70) D-Arg—D-Lys-cyclo(D-Cys—Lys—Phe—D-Cys)—D-Trp—D-Thr—D-Trp—D-Val—NH₂
(71) D-Arg—D-Lys-cyclo(D-Cys—Gly—Lys—D-Cys)—D-Trp—D-Thr—D-Trp—D-Val—NH₂
(72) D-Arg—D-Lys-cyclo(D-Cys—Gly—[N—Methyl-Phe]—D-Cys)—D-Trp—D-Thr—D-Trp—D-Val—NH₂
(73) D-Arg—D-Lys-cyclo(D-Cys—Gly—Nal—D-Cys)—D-Trp—D-Thr—D-Trp—D-Val—NH₂
(74) D-Arg—D-Lys-cyclo-(D-Cys—Phe—Gly—D-Cys)—D-Trp—D-Thr—D-Trp—D-Val—NH₂
(75) D-Arg—D-Lys—cyclo(D-Cys—Gly—Phe—D-Cys)—Val—D-Trp—D-Thr—D-Trp—NH₂
(76) D-Arg—D-Lys-cyclo(D-Cys—Gly—Phe—D-

| | |
|---|---|
| (77) | Cys)—D-Pro—D-Thr—D-Trp—D-Val—NH$_2$ |
| | D-Arg—D-Lys-cyclo(D-Cys—Gly—Phe—D-Cys)—D-Trp—D-Thr—D-Pro—D-Val—NH$_2$ |
| (78) | D-Arg—D-Lys-cyclo-desthio(D-Cys—Gly—Phe—D-Cys)—D-Trp—D-Thr—D-Nal—D-Val—NH$_2$ |
| (79) | D-Arg—D-Lys-cyclo(D-Cys—Gly—Phe—D-Cys)—D-Trp—D-Thr—D-Phe—D-Val—NH$_2$ |
| (80) | D-Arg—D-Lys-cyclo(D-Cys—Gly—Phe—D-Cys)—D-Trp—D-Thr—Pro—D-Val—NH$_2$ |
| (81) | D-Arg—D-Lys-cyclo-desthio(D-Cys—Gly—Phe—D-Cys)—D-Trp—D-Thr—D-Trp—D-Val—NH$_2$ |
| (82) | D-Arg—D-Lys—Cyclo(D-Cys—Gly—Phe—D-Cys)—Pro—D-Thr—D-Trp—D-Val—NH$_2$ |
| (83) | D-Arg—D-Lys—cyclo(D-Cys—Pro—Gly—D-Cys)—D-Trp—D-Thr—D-Trp—D-Val—NH$_2$ |
| (84) | D-Arg—D-Lys—cyclo(D-Cys—Pro—Phe—D-Cys)—D-Trp—D-Thr—D-Trp—D-Val—NH$_2$ |
| (85) | D-Arg—D-Lys—cyclo(D-Cys—Gly—Pro—D-Cys)—D-Trp—D-Thr—D-Trp—D-Val—NH$_2$ |
| (86) | D-Arg—D-Lys—cyclo(D-Cys—Gly—Tic—D-Cys)—D-Trp—D-Thr—D-Trp—D-Val—NH$_2$ |
| (87) | D-Arg—D-Lys—cyclo(D-Cys—Gly—Tyr—D-Cys)—D-Trp—D-Thr—D-Trp—D-Val—NH$_2$ |
| (88) | D-Arg—D-Lys-cyclo-desthio(D-Cys—Gly—Tyr—D-Cys)—D-Trp—D-Thr—D-Trp—D-Val—NH$_2$ |
| (89) | D-Arg—D-Lys—cyclo(D-Cys—Gly—Val—D-Cys)—D-Trp—D-Thr—D-Trp—D-Val—NH$_2$ |
| (90) | D-Arg—D-Lys—cyclo(D-Cys—Gly—Phe—D-Cys)—D-Trp—D-Thr—D-Arg—D-Val—NH$_2$ |
| (91) | D-Arg—D-Lys—cyclo(D-Cys—Gly—Phe—Cys)—D-Trp—D-Thr—D-Trp—D-Val—NH$_2$ |
| (92) | D-Arg—D-Lys—cyclo(D-Cys—D-Ile—Ile—D-Cys)—D-Trp—D-Thr—D-Trp—D-Val—NH$_2$ |
| (93) | D-Arg—D-Lys—cyclo(D-Cys—D-Ile—Phe—D-Cys)—D-Trp—D-Thr—D-Trp—D-Val—NH$_2$ |
| (94) | D-Arg—D-Lys—cyclo(D-Cys—His—Phe—D-Cys)—D-Trp—D-Thr—D-Trp—D-Val—NH$_2$ |
| (95) | D-Arg—D-Lys-cyclo(D-Cys—Ile—Pro—D-Cys)—D-Trp—D-Thr—D-Trp—D-Val—NH$_2$ |
| (96) | D-Arg—D-Lys-cyclo(D-Cys—Gly—Phe—D-Cys)—D-Trp—D-Thr—Trp—D-Val—NH$_2$ |
| (97) | D-Arg—D-Lys-cyclo(D-Cys—Gly—Phe—D-Cys)—D-Trp—D-Thr—D-Trp—Val—NH$_2$ |
| (98) | D-Arg—D-Lys-cyclo(D-Cys—Gly—Phe—D-Cys)—D-Trp—Thr—D-Trp—D-Val—NH$_2$ |
| (99) | D-Arg—D-Lys-cyclo(D-Cys—Gly—Phe—D-Cys)—Trp—D-Thr—D-Trp—D-Val—NH$_2$ |
| (100) | D-Arg—D-Lys-cyclo(D-Cys—Gly—Phe—D-Cys)—D-Tyr—D-Thr—D-Gln—D-Val—NH$_2$ |
| (101) | Arg—D-Lys-cyclo(D-Cys—Gly—Phe—D-Cys)—D-Trp—D-Thr—D-Trp—D-Val—NH$_2$ |
| (102) | D-Arg—D-Lys-cyclo(D-Cys—Gly—Phe—D-Cys)—D-Trp—D-Thr—D-Trp—Gln—NH—Bu |
| (103) | D-Arg—D-Lys-cyclo(D-Cys—Gly—Phe—D-Cys)—D-Trp—D-Val—D-Trp—D-Val |
| (104) | Ac—D-Lys-cyclo(D-Cys—Gly—Tyr—D-Cys)—D-Trp—D-Thr—D-Trp—D-Val—NH$_2$ |
| (110) | D-Arg—D-Ala—cyclo(D-Cys—Gly—Phe—D-Cys)—D-Trp—D-Thr—D-Trp—D-Val—NH$_2$ |
| (111) | D-Arg—D-Gln—cyclo(D-Cys—Gly—Phe—D-Cys)—D-Trp—D-Thr—D-Trp—D-Val—NH$_2$ |
| (112) | D-Arg—D-Glu—cyclo(D-Cys—Gly—Phe—D-Cys)—D-Trp—D-Thr—D-Trp—D-Val—NH$_2$ |
| (113) | D-Arg—D-Lys-cyclo(Cys—Gly—Gly—Cys)—D-Trp—D-Thr—D-Trp—D-Val—NH$_2$ |
| (114) | D-Arg—D-Lys-cyclo(D-Cys—D-Gln—Gln—D-Cys)—D-Trp—D-Thr—D-Trp—D-Val—NH$_2$ |
| (115) | D-Arg—D-Lys-cyclo(D-Cys—Gly—(p-Cl-Phe)—D-Cys)—D-Trp—D-Thr—D-Trp—D-Val—NH$_2$ |
| (116) | D-Arg—D-Lys-cyclo(D-Cys—Gly—D-Val—D-Cys)—D-Trp—D-Thr—D-Trp—D-Val—NH$_2$ |
| (117) | D-Asp—D-Lys-cyclo(D-Cys—Gly—Phe—D-Cys)—D-Trp—D-Thr—D-Trp—D-Val—NH$_2$ |

Formula VI:

| | |
|---|---|
| (30) (SEQ ID NO:17) | Arg—Lys—Ile—cyclo(Glu—Gly—Ile—Trp—Lys)—Trp—Val—NH$_2$ |
| (31) (SEQ ID NO:18) | Arg—Lys—Ile—cyclo(Lys—Gly—Ile—Trp—Glu)—Trp—Val—NH$_2$ |

Formula VII:

| | |
|---|---|
| (32) | D-Arg—D-Lys—D-Ile—Gly—cyclo(D-Cys—D-Ile—D-Trp—D-Cys)—D-Thr—D-Val—NH$_2$ |
| (107) | D-Arg—D-Lys—D-Ile—Gly—cyclo(D-Cys—D-Ile—D-Trp—D-Cys)—D-Trp—D-Val—NH$_2$ |
| (108) | D-Arg—D-Lys—D-Ile—Gly—cyclo-(D-Cys—D-Ile—D-Trp—D-Cys)—D-Thr—D-Val—NH$_2$ |

Formula VIII:

| | |
|---|---|
| (33) (SEQ ID NO:19) | Arg—Lys—Ile—Gly—Gly—cyclo(Cys—Trp—Thr—Trp—Cys)—NH$_2$ |

Formula IX:

| | |
|---|---|
| (105) | D-Arg—cyclo[D-Lys-cyclo(D-Cys—Gly—Phe—D-Cys)—D-Trp—D-Thr—D-Trp—D-Glu]—NH$_2$ |

Formula X:

| | |
|---|---|
| (106) | D-Arg-cyclo[D-Lys-cyclo(D-Cys—Gly—Phe—D-Cys)—D-Trp—D-Glu]—D-Trp—D-Val—NH$_2$ |

Formula XI:

| | |
|---|---|
| (109) | cyclo(D-Cys—D-Lys—D-Ile—D-Cys)—Gly—D-Ile—D-Trp—D-Thr—D-Trp—D-Val—NH$_2$ |

As used herein, the term "lower alkyl" includes branched, straight-chain, and cyclic saturated hydrocarbons having from one to six carbon atoms, such as methyl, ethyl, propyl, isopropyl, butyl, isobutyl, t-butyl, pentyl, isopentyl, neopentyl, cyclopentylmethyl and hexyl. The term "lower alkanoyl" means $$R^6-\overset{O}{\underset{\|}{C}}-$$

wherein $R^6$ is a lower alkyl group. The term aroyl means $$R^7-\overset{O}{\underset{\|}{C}}-$$

wherein $R^7$ is an aromatic or heteroaromatic structure having between one and three rings, which may or may not be ring fused structures, and are optionally substituted with halogens, carbons, or other heteroatoms such as nitrogen (N), sulfur (S), phosphorus (P), and boron (B). The term alkoxycarbonyl means $$R^8-O-\overset{O}{\underset{\|}{C}}-O-$$

wherein $R^8$ is a lower alkyl group. The term aryloxycarbonyl means $$R^9-O-\overset{O}{\underset{\|}{C}}-O-$$

wherein $R^9$ is an aryl and arylmethyl group.

The peptides of Formulas I through XI can be used in the form of the free peptide or a pharmaceutically acceptable salt. Amine salts can be prepared by treating the peptide with an acid according to known methods. Suitable acids include inorganic acids such as hydrochloric acid, hydrobromic acid, perchloric acid; nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, fumaric acid, anthranilic acid, cinnamic acid, naphthalenesulfonic acid, and sulfanilic acid.

Carboxylic acid groups in the peptide can be converted to a salt by treating the peptide with a base according to known methods. Suitable bases include inorganic bases such as sodium hydroxide, ammonium hydroxide, and potassium hydroxide, and organic bases such as mono-, di-, and tri-alkyl and aryl amines (e.g., triethylamine, diisopropylamine, methylamine, and dimethylamine and optionally substituted mono-, di, and tri-ethanolamines.

As referred to herein, the amino acid components of the peptides and certain materials used in their preparation are identified by abbreviations for convenience. These abbreviations are as follows:

| Amino Acid | Abbreviations | |
| --- | --- | --- |
| L-alanine | Ala | A |
| D-alanine | D-Ala | a |
| L-arginine | Arg | R |
| D-arginine | D-Arg | r |
| D-asparagine | D-Asn | N |
| L-asparagine | Asn | n |
| L-aspartic acid | Asp | D |
| D-aspartic acid | D-Asp | d |
| L-cysteine | Cys | C |
| D-cysteine | D-Cys | c |
| L-glutamic acid | Glu | E |
| D-glutamic acid | D-Glu | e |
| L-glutamine | Gln | K |
| D-glutamine | D-Gln | k |
| glycine | Gly | G |
| L-histidine | His | H |
| D-histidine | D-His | h |
| L-isolelucine | Ile | I |
| D-isolelucine | D-Ile | i |
| L-leucine | Leu | L |
| D-leucine | D-Leu | l |
| L-lysine | Lys | K |
| D-lysine | D-Lys | k |
| D-penicillamine | Pen | |
| L-phenylalanine | Phe | F |
| D-phenylalanine | D-Phe | f |
| L-proline | Pro | P |
| D-proline | D-Pro | p |
| L-pyroglutamic acid | pGlu | |
| D-pyroglutamic acid | D-pGlu | |
| L-serine | Ser | S |
| D-serine | D-Ser | s |
| L-threonine | Thr | T |
| D-threonine | D-Thr | t |
| L-tyrosine | Tyr | Y |
| D-tyrosine | D-Tyr | y |
| L-tryptophan | Trp | W |
| D-tryptophan | D-Trp | w |
| L-valine | Val | V |
| D-valine | D-Val | v |
| L-alloisolucine | Allo | |
| D-alloisolucine | D-Allo | |
| delta-aminovaleryl | Ava | |
| diaminopropionyl | Dap | |
| L-thio-proline | Tpro | |
| D-thio-poline | D-Tpro | |
| L-tetrahydroisoquinoline-carboxylic acid | Tic | |
| D-tetrahydroisoquinoline-carboxylic acid | D-Tic | |
| L-naphthyl-alanine | Nal | |
| D-naphthyl-alanine | D-Nal | |

-continued

| Reagents | Abbreviations |
| --- | --- |
| Trifluoroacetic acid | TFA |
| Methylene chloride | $CH_2Cl_2$ |
| N,N-Diisopropylethylamine | DIEA |
| N-Methylpyrrolidone | NMP |
| 1-Hydroxybenzotriazole | HOBT |
| Dimethylsulfoxide | DMSO |
| Acetic anhydride | $Ac_2O$ |

Methods of Preparation of Peptides

The peptides can generally be prepared following known techniques, as described, for example, in the cited publications, the teachings of which are specifically incorporated herein. In a preferred method, the peptides are prepared following the solid-phase synthetic technique initially described by Merrifield in *J. Amer. Chem. Soc.*, 85, 2149–2154 (1963). Other techniques may be found, for example, in M. Bodanszky, et al, *Peptide Synthesis*, second edition, (John Wiley & Sons, 1976), as well as in other reference works known to those skilled in the art.

In those instances where the cyclic nature of the peptide comprises an amide bond, the techniques for forming this amide bond involve selective removal of one carboxylic acid protecting group and one amino protecting group and the activation of the free carboxylic acid to render it susceptible to nucleophilic attack by the free amino group. This cyclization may be performed on the resin prior to cleavage where the peptide is produced by solid phase synthetic techniques or in solution after cleavage where the solid phase technique is used or in solution where solution phase technology has been used. In those instances where the cyclic nature of the peptide involves the formation of a disulfide bond, the general techniques for the formation of this bond are described by G. Barany and R. B. Merrifield in *The Peptides Analysis, Synthesis, Biology*, (Academic Press, Inc., 1979), as well as in other reference works known to those skilled in the art.

Appropriate protective groups usable in such syntheses and their abbreviations will be found in the above text, as well as in J. F. W. McOmie, *Protective Groups in Organic Chemistry*, (Plenum Press, New York, 1973). The common protective groups used herein are t-butyloxycarbonyl (Boc), fluorenylmethoxycarboyl (FMOC), benzyl (Bzl), tosyl (Tos), o-bromo-phenylmethoxycarbonyl (BrCBZ), phenylmethoxycarbonyl (CBZ), 2-chloro-phenylmethoxycarbonyl (2-Cl-CBZ), 4-methoxy-2,3,6-trimethylbenzenesulfonyl (Mtr), trityl (Trt), formyl (CHO), tertiary butyl (t-Bu), fluorenylmethyl (OFm), and methoxybenzyl (Mob).

General synthetic procedures for the synthesis of peptides of Formulas I–XI by solid phase methodology are as follows:

| General Synthetic Procedures For Solid Phase Peptide Synthesis Using $N^\alpha$-Boc Protection | | |
| --- | --- | --- |
| | REPETITIONS | TIME |
| 1. 25% TFA in $CH_2Cl_2$ | 1 | 3 min. |
| 2. 50% TFA in $CH_2Cl_2$ | 1 | 16 min. |
| 3. $CH_2Cl_2$ | 5 | 3 min. |
| 4. 5% DIEA in NMP | 2 | 4 min. |
| 5. NMP | 6 | 5 min. |
| 6. Coupling step | 1 | 57 min. |
|    a. Preformed BOC-Amino Acid-HOBT active ester in NMP | | 37 min. |
|    b. DMSO | | 16 min. |

General Synthetic Procedures For Solid Phase Peptide Synthesis Using N$^\alpha$-Boc Protection

|   | REPETITIONS | TIME |
|---|---|---|
| c. DIEA |   | 5 min. |
| 7. 10% Ac$_2$O, 5% DIEA in NMP | 1 | 9 min. |
| 8. CH$_2$Cl$_2$ | 5 | 3 min. |

The peptides can also be prepared using standard genetic engineering techniques known to those skilled in the art. For example, the peptide can be produced enzymatically by inserting nucleic acid encoding the linear precursor peptide into an expression vector, expressing the DNA, and translating the DNA into the peptide in the presence of the required amino acids. The linear peptide is then purified using chromatographic or electrophoretic techniques, or by means of a carrier protein which can be fused to, and subsequently cleaved from, the peptide by inserting into the expression vector in phase with the peptide encoding sequence a nucleic acid sequence encoding the carrier protein. The fusion protein-peptide may be isolated using chromatographic, electrophoretic or immunological techniques (such as binding to a resin via an antibody to the carrier protein). The peptide can be cleaved using chemical methodology or enzymatically, as by, for example, hydrolases. The linear peptide can then be chemically cyclized to yield the desired cyclic peptide.

Peptides of Formula I–XI can also be prepared using solution methods, by either stepwise or fragment condensations. An appropriately alpha amino-protected amino acid is coupled to an appropriately alpha carboxyl protected amino acid (such protection may not be required depending on the coupling method chosen) using diimides, symmetrical or unsymmetrical anhydrides, BOP, or other coupling reagents or techniques known to those skilled in the art. These techniques may be either or enzymatic. The alpha amino and/or alpha carboxyl protecting groups are removed and the next suitably protected amino acid or block of amino acids are coupled to extend the growing peptide. Various combinations of protecting groups and of chemical and/or enzymatic techniques and assembly strategies can be used in each synthesis.

Methods of Preparation of Pharmaceutical Compositions

Pharmaceutical compositions of this invention comprise a pharmaceutically acceptable carrier or diluent and an effective quantity of one or more of the peptides of Formulas I–XI or an acid or base salt thereof. The carrier or diluent may take a wide variety of forms depending on the form of preparation desired for administration, e.g., sublingual, rectal, nasal, oral, or parenteral.

In preparing the compositions in oral dosage form, any of the usual pharmaceutical media may be employed, for example, waters, oils, alcohols, flavoring agents, preservatives, and coloring agents, to make an oral liquid preparation (e.g., suspension, elixir, or solution) or with carriers such as starches, sugars, diluents, granulating agents, lubricants, binders, and disintegrating agents, to make an oral solid preparation (e.g., powder, capsule, or tablet).

Controlled release forms or enhancers to increase bioavailability may also be used. Because of their ease in administration, tablets and capsules represent the most advantageous oral dosage unit form, in which case solid pharmaceutical carriers are employed. If desired, tablets may be sugar coated or enteric coated by standard techniques.

For parenteral products, the carrier will usually be sterile water, although other ingredients to aid solubility or as preservatives may be included. Injectable suspensions may also be prepared, in which case appropriate licuid carriers and suspending agents can be employed.

The peptides can also be administered locally at a wound or inflammatory site by topical application of a solution or cream.

Alternatively, the peptide may be administered in liposomes or microspheres (or microparticles). Methods for preparing liposomes and microspheres for administration to a patient are known to those skilled in the art. U.S. Pat. No. 4,789,734 describes methods for encapsulating biological materials in liposomes. Essentially, the material is dissolved in an aqueous solution, the appropriate phospholipids and lipids added, along with surfactants if required, and the material dialyzed or sonicated, as necessary. A review of known methods is by G. Gregoriadis, Chapter 14, "Liposomes", *Drug Carriers in Biology and Medicine*, pp. 287–341 (Academic Press, 1979). Microspheres formed of polymers or proteins are well known to those skilled in the art, and can be tailored for passage through the gastrointestinal tract directly into the bloodstream.

Alternatively, the peptide can be incorporated and the microspheres, or composite of microspheres, implanted for slow release over a period of time, ranging from days to months. See, for example, U.S. Pat. Nos. 4,906,474, 4,925,673 and 3,625,214.

The peptides are generally active when administered parenterally in amounts above about 1 µg/kg body weight. The peptides are generally active when administered parenterally in amounts above about 1 µg/kg body weight. Effective doses by other routes of administration are generally those which result in similar blood level to i.v. doses above about 1 µg/Kg. For treatment to prevent organ injury in cases involving reperfusion, the peptides may be administered parenterally in amounts from about 0.01 to about 10 mg/kg body weight. Generally, the same range of dosage amounts may be used in treatment of other diseases or of conditions where inflammation is to be reduced. This dosage will be dependent, in part, on whether one or more peptides are administered. A synergistic effect may be seen with combinations of peptides from different, or overlapping, regions of the lectin domain, or in combination with peptides derived form the EGF domain of P-selectin. For treatment to prevent organ injury in cases involving reperfusion, the peptides may be administered parenterally in amounts from about 0.01 to about 10 mg/kg body weight. Generally, the same range of dosage amounts may be used in treatment of other diseases or of conditions where inflammation is to be reduced. This dosage will be dependent, in part, on whether one or more peptides are administered. A synergistic effect may be seen with combinations of peptides from different, or overlapping, regions of the lectin domains of the same or different selecting, or in combination with peptides derived from the EGF domain of the same or different selecting.

Methods for Demonstrating Binding and Inhibition of Binding

Peptides that are biologically active are those which inhibit binding of neutrophils, monocytes, subsets of lymphocytes or other cells to P-selectin, which inhibit leukocyte adhesion to endothelium that is mediated by E-selectin or L-selectin or that is mediated by ICAM-1.

Peptides can be screened for their ability to inhibit adhesion to cells, for example, neutrophil adhesion to purified P-selectin immobilized on plastic wells, using the assay described by Geng, et al., *Nature* 343, 757–760 (1990).

Human neutrophils are isolated from heparinized whole blood by density gradient centrifugation on Mono-Poly resolving media, Flow Laboratories. Neutrophil suspensions are greater than 98% pure and greater than 95% viable by trypan blue exclusion. For adhesion assays, neutrophils are suspended at a concentration of $2 \times 10^6$ cells/mL in Hanks' balanced salt solution containing 1.26 mM $Ca^{2+}$ and 0.81 mM $Mg^{2+}$ (HBSS, Gibco) with g mg/mL human serum albumin (HBSS/HSA). Adhesion assays are conducted in triplicate in 96-well microliter plates, Corning, incubated at 4° C. overnight with 50 microliters of various protein solutions.

P-selectin is isolated from human platelet lysates by immunoaffinity chromatography on antibody S12-Sepharose™ and ion-exchange chromatography on a Mono-Q™ column (FLPC, Pharmacia Fine Chemicals), as follows.

Outdated human platelet packs (100 units) obtained from a blood bank and stored at 4° C. are pooled, adjusted to 5 mM EDTA at pH 7.5, centrifuged at 4,000 rpm for 30 minutes in 1 liter bottles, then washed three times with 1 liter of 0.1M NaCl, 20 mM Tris pH 7.5 (TBS), 5 mM EDTA, 5 mM benzamidine.

The pellets are then resuspended in a minimum amount of wash buffer and made 1 mM in DIFP, then frozen in 50 mL screwtop tubes at −80° C. The frozen platelets are thawed and resuspended in 50 mL TBS, 5 mM benzamidine, 5 mM EDTA pH 7.5, 100M leupeptin. The suspension is frozen and thawed two times in a dry ice-acetone bath using a 600 mL lyophilizing flask, then homogenized in a glass/teflon mortar and pestle and made 1 mM in DIFP. The NaCl concentration is adjusted to 0.5M with a stock solution of 4M NaCl. After stirring the suspension at 4° C., it is centrifuged in polycarbonate tubes at 33,000 rpm for 60 minutes at 4° C. The supernatant (0.5M NaCl wash) is removed and saved; this supernatant contains the soluble form of P-selectin. Care is taken not to remove the top part of the pellet with the supernatant. The pellets are then homogenized in extraction buffer (TBS, 5 mM benzamidine, 5 mM EDTA, pH 7.5, 100 µM leupeptin, 2% Triton X-100). After centrifugation at 19,500 rpm for 25 minutes at 4° C., the supernatant is removed. The extraction procedure is repeated with the pellet and the supernatant is combined with the first supernatant. The combined extracts, which contain the membrane form of P-selectin, are adjusted to 0.5M NaCl.

The soluble fraction (0.5M NaCl wash) and the membrane extract (also adjusted to 0.5M NaCl) are absorbed with separate pools of the monoclonal antibody S12 (directed to P-selectin) previously couple mg/mL for 2 hours ad) at 5 mg/mL for 2 hours at 4° C. After letting the resins settle, the supernatants are removed. The S12 Affigel containing bound GMP-140 is then loaded into a column and washed overnight at 4° C. with 400 mL of 0.5M NaCl, 20 mM Tris pH 7.5, 0.01% Lubrol PX.

Bound P-selectin is eluted from the S12 Affigel with 100 mL of 80% ethylene glycol, 1 mM MES pH 6.0, 0.01% Lubrol PX. Peak fractions with absorbance at 280 nm are pooled. Eluates are dialyzed against TBS with 0.05% Lubrol, then applied to a Mono Q column (FPLC from Pharmacia). The concentrated protein is step eluted with 2M NaCl, 20 mM Tris pH 7.5 (plus 0.05% Lubrol PX for the membrane fraction). Peak fractions are dialyzed into TBS pH 7.5 (plus 0.05% Lubrol PX for the membrane fraction).

P-selectin is plated at 5 micrograms/mL and the control proteins: human serum albumin (Alb), platelet glycoprotein IIb/IIIa (IIb), von Willebrand factor (vWF), fibrinogen (FIB), thrombomodulin (TM), gelatin (GEL) or human serum (HS), are added at 50 micrograms/mL. All wells are blocked for 2 hours at 22° C. with 300 microliters HBSS containing 10 mg/mL HSA, then washed three times with HBSS containing 0.1% Tween-20 and once with HBSS. Cells ($2 \times 10^5$ per well) are added to the wells and incubated at 22° C. for 20 minutes. The wells are then filled with HBSS/HSA, sealed with acetate tape (Dynatech), and centrifuged inverted at 150 g for 5 minutes. After discarding nonadherent cells and supernates, the contents of each well are solubilized with 200 microliters 0.5% hexadecyltrimethylammonium bromide, Sigma, in 50 mM potassium phosphate, pH. 6.0, and assayed for myeloperoxidase activity, Ley, et al., *Blood* 73, 1324–1330 (1989). The number of cells bound is derived from a standard curve of myeloperoxidase activity versus numbers of cells. Under all assay conditions, the cells release less than 5% of total myeloperoxidase and lactate dehydrogenase. Inhibition is read as a lower percent adhesion, so that a value of 5% means that 95% of the specific adhesion was inhibited.

The ability to inhibit ICAM-1 dependent cell adhesion can be demonstrated by stimulation of HUVEC cells by TNF or IL-1 for periods of time from 15–20 hr. Stimulation for this period of time results cellular adhesion, for example neutrophils, that is ICAM-1 and not selectin dependent.

Clinical Applications

Since the selectins and ICAM-1 have several functions related to leukocyte adherence, inflammation, and coagulation, compounds which interfere with binding of P-selectin, E-selectin, L-selectin or ICAM-1 can be used to modulate these responses.

For example, the peptides can be used to competitively inhibit leukocyte adherence by competitively binding to P-selectin receptors on the surface of leukocytes. This kind of therapy would be particularly useful in acute situations where effective, but transient, inhibition of leukocyte-mediated inflammation is desirable. Chronic therapy by infusion of the peptides may also be feasible in some circumstances.

An inflammatory response may cause damage to the host if unchecked, because leukocytes release many toxic molecules that can damage normal tissues. These molecules include proteolytic enzymes and free radicals. Examples of pathological situations in which leukocytes can cause tissue damage include injury from ischemia and reperfusion, bacterial sepsis and disseminated intravascular coagulation, adult respiratory distress syndrome, tumor metastasis, rheumatoid arthritis and atherosclerosis.

Reperfusion injury is a major problem in clinical cardiology. Therapeutic agents that reduce leukocyte adherence in ischemic myocardium can significantly enhance the therapeutic efficacy of thrombolytic agents. Thrombolytic therapy with agents such as tissue plasminogen activator or streptokinase can relieve coronary artery obstruction in many patients with severe myocardial ischemia prior to irreversible myocardial cell death. However, many such patients still suffer myocardial neurosis despite restoration of blood flow. This "reperfusion injury" is known to be associated with adherence of leukocytes to vascular endothelium in the ischemic zone, presumably in part because of activation of platelets and endothelium by thrombin and cytokines that makes them adhesive for leukocytes (Romson et al., *Circulation* 67: 1016–1023 (1983)). These adherent leukocytes can migrate through the endothelium and destroy ischemic myocardium just as it is being rescued by restoration of blood flow.

There are a number of other common clinical disorders in which ischemia and reperfusion results in organ injury mediated by adherence of leukocytes to vascular surfaces, including strokes; mesenteric and peripheral vascular disease; organ transplantation; and circulatory shock (in this case many organs might be damaged following restoration of blood flow).

Bacterial sepsis and disseminated intravascular coagulation often exist concurrently in critically ill patients. They are associated with generation of thrombin, cytokines, and other inflammatory mediators, activation of platelets and endothelium, and adherence of leukocytes and aggregation of platelets throughout the vascular system.

Leukocyte-dependent organ damage is an important feature of these conditions.

Adult respiratory distress syndrome is a devastating pulmonary disorder occurring in patients with sepsis or following trauma, which is associated with widespread adherence and aggregation of leukocytes in the pulmonary circulation. This leads to extravasation of large amounts of plasma into the lungs and destruction of lung tissue, both mediated in large part by leukocyte products.

Two related pulmonary disorders that are often fatal are in immunosuppressed patients undergoing allogeneic bone marrow transplantation and in cancer patients suffering from complications that arise from generalized vascular leakage resulting from treatment with interleukin-2 treated LAK cells (lymphokine-activated lymphocytes). LAK cells are known to adhere to vascular walls and release products that are presumably toxic to endothelium. Although the mechanism by which LAK cells adhere to endothelium is now known, such cells could potentially release molecules that activate endothelium and then bind to endothelium by mechanisms similar to those operative in neutrophils.

Tumor cells from many malignancies (including carcinomas, lymphomas, and sarcomas) can metastasize to distant sites through the vasculature. The mechanisms for adhesion of tumor cells to endothelium and their subsequent migration are not well understood, but may be similar to those of leukocytes in at least some cases. The association of platelets with metastasizing tumor cells has been well described, suggesting a role for platelets in the spread of some cancers. Recently, it was reported that P-selectin binds to tumor cells in a variety of human carcinoma tissue sections (colon, lung, and breast), and that P-selectin binds to the cell surface of a number of cell lines derived from various carcinomas, but not from melanomas. Aruggo, A., et al., *Proc. Natl. Acad. Sci. USA*, 89, 2292–2296 (1992). Aruggo et al. also reference earlier work suggesting that E-selectin might be involved in tumor metastasis by mediating the adhesion of a colon carcinoma cell line (HT-20) to activated endothelial cells in vitro.

Platelet-leukocyte interactions are believed to be important in atherosclerosis. Platelets might have a role in recruitment of monocytes into atherosclerotic plaques; the accumulation of monocytes is known to be one of the earliest detectable events during atherogenesis. Rupture of a fully developed plaque may not only lead to platelet deposition and activation and the promotion of thrombus formation, but also the early recruitment of neutrophils to an area of ischemia.

Another area of potential application is in the treatment of rheumatoid arthritis.

The criteria for assessing response to therapeutic modalities employing these peptides, and, hence, effective dosages of the peptides of this invention for treatment, are dictated by the specific condition and will generally follow standard medical practices. For example, the criteria for the effective dosage to prevent extension of myocardial infarction would be determined by one skilled in the art by looking at marker enzymes of myocardial necrosis in the plasma, by monitoring the electrocardiogram, vital signs, and clinical response. For treatment of acute respiratory distress syndrome, one would examine improvements in arterial oxygen, resolution of pulmonary infiltrates, and clinical improvement as measured by lessened dyspnea and tachypnea. For treatment of patients in shock (low blood pressure), the effective dosage would be based on the clinical response and specific measurements of function of vital organs such as the liver and kidney following restoration of blood pressure. Neurologic function would be monitored in patients with stroke. Specific tests are used to monitor the functioning of transplanted organs; for example, serum creatinine, urine flow, and serum electrolytes in patients undergoing kidney transplantation.

Diagnostic Reagents

The peptides can also be used for the detection of human disorders in which the ligands for the selectins or ICAM-1 might be defective. Such disorders would most likely be seen in patients with increased susceptibility to infections in which leukocytes might not be able to bind to activated platelets or endothelium. Cells to be tested, usually leukocytes, are collected by standard medically approved techniques and screened. Detection systems include ELISA procedures, binding of radiolabeled antibody to immobilized activated cells, flow cytometry, or other methods known to those skilled in the art. Inhibition of binding in the presence and absence of the lectin domain peptides can be used to detect defects or alterations in selectin or ICAM-1 binding. For selecting, such disorders would most likely be seen in patients with increased susceptibility to infections in which leukocytes would have defective binding to platelets and endothelium because of deficient leukocyte ligands for P-selectin.

The peptide is labeled radioactively, with a fluorescent tag, enzymatically, or with electron dense material such as gold for electron microscopy. The cells to be examined, usually leukocytes, are incubated with the labeled peptides and binding assessed by methods described above with antibodies to P-selectin, or by other methods known to those skilled in the art. If ligands for selectins or ICAM-1 are also found in the plasma, they can also be measured with standard ELISA or radioimmunoassay procedures, using labeled P-selectin-derived peptide instead of antibody as the detecting reagent.

The peptides can also be useful in in vivo imaging of concentrations of cells bearing selectin or ICAM-1 ligands. Cells expressing selectin ligands whose abnormally high local concentrations or presence within the body such as cancer cells, is indicative of a disorder can be imaged using labeled peptides. These labels may be either intrinsic or extrinsic to the structure of the specific selectin peptide and may include, but not be limited to high energy emitters such as $^{111}$In or non-radioactive dense atoms to enhance x-ray contrast.

The following examples are presented to illustrate, not limit, the invention. In the examples and throughout the specification, parts are by weight unless otherwise indicated.

EXAMPLE I

Arginyl-lysyl-isoleucyl-glycyl-glycyl-cyclo (cysteinyl-tryptophyl-threonyl-tryptophyl-cystine)-amide (Preferred peptide (33)) (SEQ ID NO:19)

The peptide was prepared on an ABI Model 431A Peptide Synthesizer using Version 1.12 of the standard Boc software.

4-methyl benzhydrylamine resin (0.625 g, 0.5 mmol) was used in the synthesis. The final weight of the resin was 1.655 g.

The peptide was cleaved from the resin (1.539 g) using 15 mL of HF and 1.5 mL of anisole for 60 min at 0° C. The resin was washed with ether and the peptide extracted with a 1:1 solution of TFA/CH$_2$Cl$_2$ to give 1.111 g of crude peptide. The tryptophans were deformylated by dissolving the peptide into 250 mL of water with 5 mL of piperidine. The solution was stirred at 4° C. for one hour, monitored by HPLC and lyophilized when the reaction was complete. The crude peptide (1.692 g) was cyclized by dissolving it into 2 liters of aqueous DMSO (10%) and allowing it to stir overnight at room temperature. The reaction was monitored by HPLC and the solution was lyophilized when the reaction was complete.

The crude cyclic peptide was purified on a Vydac C-18 column (15μ, 5×25 cm) eluting with a 20–50% gradient of 80% acetonitrile in 0.1% TFA over 120 min at a flow rate of 15 mL per min. Fractions were collected, analyzed by HPLC and pure fractions pooled and lyophilized to give 89 mg. Amino acid analysis: Arg 1.0 (1), Cys 1.95 (2), Gly 2.05 (2), Ile 0.97 (1), Lys 1.0 (1), Thr 0.87 (1), Trp 0.60 (2). FAB/MS: MH$^+$ 1206.3

EXAMPLE II

Arginyl-Lysyl-cyclo(cysteinyl-glycyl-glycyl-D-penicillamyl)-tryptophyl-threonyl-tryptophyl-valine-amide (Preferred peptide (10)) (SEQ ID NO:12)

The peptide was prepared on an ABI Model 431A Peptide Synthesizer using Version 1.12 of the standard Boc software. 4-methyl benzhydrylamine resin (0.625 g, 0.5 mmol) was used in the synthesis. Boc-S(p-methoxybenzyl)-D-penicillamine (MW 369.2, 0.738 g, 2 mmol) was supplied by Bachem of California. The final weight of the resin was 1.811 g.

The peptide was cleaved from the resin (1.810 g) using 18 mL of HF and 1.8 mL of anisole for 60 min at 0° C. The resin was washed with ether and the peptide extracted with a 1:1 solution of TFA/CH$_2$CO$_2$ to give 1.110 g of crude peptide. The peptide was deformylated with a 2% piperidine (aqueous) solution for one hour at 4° C. and then lyophilized. The dry product was then cyclized by dissolving the peptide into 1600 mL of a 10% DMSO (aqueous) solution, with a pH of 6.0 and was stirred overnight. The solution was then lyophilized and directly purified.

The crude peptide was purified on a Vydac C-18 column (15μ, 5×25 cm) eluting with a 25–45% gradient of 80% acetonitrile in 0.1% TFA over 120 min at a flow rate of 15 mL per min. Fractions were collected, analyzed by HPLC and pure fractions pooled and lyophilized to give 190 mg. Amino acid analysis: Arg 0.98 (1), Cys 1.0 (0.92), Gly 2.03 (2), Lys 0.99 (1), Thr 0.81 (1), Trp 0.23 (2), Val 1.01 (1). FAB/MS: MH$^+$ 1220.5

EXAMPLE III

Arginyl-cyclo(cysteinyl-isoleucyl-glycyl-glycyl-cysteinyl)-tryptophyl-threonyl-tryptophyl-valine-amide (Preferred peptide (5)) (SEQ ID NO:8)

The peptide was prepared on an ABI Model 431A Peptide Synthesizer using Version 1.12 of the standard Boc software. 4-methyl benzhydrylamine resin (0.625 g, 0.5 mmol) was used in the synthesis. The final weight of the resin was 1.53 g.

The peptide was cleaved from the resin (1.5 g) using 15 mL of HF and 1.5 mL of anisole for 60 min at 0° C. The resin was washed with ether and the peptide extracted with TFA/CH$_2$Cl$_2$ (1:1, v/v) (3×15 mL) to give 885 mg of crude peptide. The linear, crude peptide (800 mg) was dissolved in 20% DMSO/water solution (1000 mL), stirred overnight at room temperature then lyophilized. The crude cyclic peptide (approx. 1.2 g) was dissolved in 200 mL of 70% acetic acid and then purified in two runs on a Vydac C-18 column (15μ, 10×30 cm) eluting with a a) 0–35%; b) 35–100% gradient of 80% acetonitrile in 0.1% TFA over a) 15 min; b) 45 min at a flow rate of 120 mL per min. Fractions were collected, analyzed by HPLC and pure fractions pooled and lyophilized to give 55 mg of white solid. Amino acid analysis: Arg 1.02 (1), Cys (O$_3$H) 1.70 (2), Gly 2.01 (2), Ile 0.96 (1), Thr 0.93 (1), Trp 0.73 (1), Val 1.01 (1). FAB/MS: MH$^+$ 1177.8

EXAMPLE IV

Cyclo-(cysteinyl-lysyl-isoleucyl-glycyl-glycyl-isoleucyl-tryptophyl-threonyl-tryptophyl-cystine)-amide (Preferred peptide (3)) (SEQ ID NO:7)

The peptide was prepared on an ABI Model 431A Peptide Synthesizer using Version 1.12 of the standard Boc software. 4-methyl benzhydrylamine resin (0.625 g, 0.5 mmol) was used in the synthesis. The final weight of the resin was 1.621 g. Half of this resin (750 mg) was deformylated before cleavage by stirring the resin in a 20% piperidine (in NMP) solution overnight. The resin was then cleaved as follows.

The peptide was cleaved from the resin (799 mg) using 10 mL of HF and 800 gL of anisole for 60 min at 0° C. The resin was washed with ether and the peptide extracted with a 1:1 solution of TFA/CH$_2$Cl$_2$ to give 461 mg of crude peptide. This peptide was deformylated with a 2% piperidine (aqueous) solution for one hour. The reaction was monitored by HPLC. When the other batch was cleaved, retention times were compared and the two batches combined.

The peptide was cyclized by dissolving 400 mg of peptide into 80 mL of 50% acetic acid. A solution of (1600 mL) of 10% DMSO (aqueous) was prepared to which the peptide solution was added. The pH was 5.5 and the solution stirred overnight. The reaction was monitored by HPLC and lyophilized when complete.

The crude peptide (approximately 600 mg) was purified on a Vydac C-18 column (15μ, 5×25 cm) eluting with a 30–50% gradient of 80% acetonitrile in 0.1% TFA over 120 min at a flow rate of 15 mL per min. Fractions were collected, analyzed by HPLC and pure fractions pooled and lyophilized to give 80 mg. Amino acid analysis: Cys 1.93 (2), Gly 2.07 (2), Ile 1.90 (2), Lys 1.02 (1), Thr 0.90 (1), Trp 0.32 (2). FAB/MS: MH$^+$ 1163.9

EXAMPLE V

Arginyl-lysyl-isoleucyl-cyclo(glutamyl-glycyl-isoleucyl-tryptophyl-lysyl)-tryptophyl-valine-amide (Preferred peptide (30)) (SEQ ID NO:17)

The peptide was prepared on an ABI Model 431A Peptide Synthesizer using Version 1.12 of the Standard Boc software. 4-methyl benzhydrylamine resin (0.625 g, 0.5 mmol) was used in the synthesis. Boc-Tryptophan (0.612 g, 2 mmol) supplied by Bachem Bioscience, Boc-Glu(OFm) (0.856 g, 2 mmol) and Boc-Lys(FMOC) (0.936 g, 2 mmol) supplied by Bachem of California, were used. The final weight of the resin was 1.823 g. The peptide was cyclized by deprotecting the glutamic acid and the lysine with a 20% piperidine (in NMP) solution for 20 min followed by treatment with BOP [Benzotriazole-1-yl-oxy-tris-(dimethylamino)-phosphonium-hexafluorophosphate] reagent (0.67 g, 1.5 mmol) and DIEA [N,N-Dissopropylethylanine] (0.6 mL, 3 mmol) for three hours. The final yield of the resin was 1.713 g.

The peptide was cleaved from the resin (1.625 g) using 16 mL of HF and 1.6 mL of anisole for 60 min at 0° C. The resin was washed with ether and the peptide extracted with a 1:1 solution of TFA/CH$_2$Cl$_2$ to give 829 mg of crude peptide.

The crude peptide (829 mg) was purified on a Vydac C-18 column (15μ, 5.0×25 cm) eluting with a 25–65% gradient of 80% acetonitrile in 0.1% TFA over 120 min at a flow rate of 15 mL per min. Fractions were collected, analyzed by HPLC and pure fractions pooled and lyophilized to give 201 mg. Amino acid analysis: Arg 1.0 (1), Glx 1.01 (1), Gly 1.01 (1), Ile 1.84 (2), Lys 1.98 (2), Trp 1.58 (2), Val 1.0 (1). MH$^+$ 1295.9

EXAMPLE VI

Arginyl-lysyl-cyclo(cysteinyl-glycyl-glycyl-cysteinyl)-tryptophyl-threonyl-tryptophyl-valine-amide (Preferred peptide (9)) (SEQ ID NO:11)

The peptide was prepared on an ABI Model 431A Peptide Synthesizer using Version 1.12 of the standard Boc software. 4-methyl benzhydrylamine resin (0.625 g, 0.5 mmol) was used in the synthesis. The final weight of the resin was 1.786 g.

The peptide was cleaved from the resin (1.745 g) using 18 mL of HF and 1.75 mL of anisole for 60 min at 0° C. The resin was washed with ether and the peptide extracted with a 1:1 solution of TFA/CH$_2$Cl$_2$ to give 1.144 g of crude peptide. The crude peptide (545 mg) was cyclized by dissolving the peptide into one liter of 10% DMSO (aqueous), pH 7.5 and stirred overnight. The liquid was lyophilized and directly purified.

The crude peptide was purified on a Vydac C-18 column (15μ, 5×25 cm) eluting with a 25–65% gradient of 80% acetonitrile in 0.1% TFA over 120 min at a flow rate of 15 mL per min. Fractions were collected, analyzed by HPLC and pure fractions pooled and lyophilized to give 24 mg. Amino acid analysis: Arg 0.83 (1), Cys 1.40 (2), Gly 1.97 (2), Lys 1.0 (1), Thr 0.85 (1), Trp 0.74 (2), Val 1.01 (1). FAB/MS: MH$^+$ 1192.1

EXAMPLE VII

D-Arginyl-D-lysyl-cyclo(D-cysteinyl-glycyl-glycyl-D-cysteinyl)-D-tryptophyl-D-threonyl-D-tryptophan-amide (Preferred peptide (8))

The peptide was prepared on an ABI Model 431A Peptide Synthesizer using Version 1.12 of the standard Boc software. 4-methyl benzhydrylamine resin (0.625 g, 0.5 mmol) was used in the synthesis. The final weight of the resin was 1.53 g.

The peptide was cleaved from the resin (1.5 g) using 15 mL of HF and 1.5 mL of anisole for 60 min at 0° C. The resin was washed with ether and the peptide extracted with TFA/CH$_2$Cl$_2$ (1:1, v/v) (3×15 mL) to give 0.7 g of crude peptide. The crude linear peptide (700 mg) was dissolved in 60 mL of 70% AcOH and then added dropwise to the mixture of water (1200 mL), NH$_4$OH (to keep pH approx. 7.5) and 0.01M K$_3$Fe(CN)$_6$ (approx. 3 mL). After each addition of the linear precursor to the reaction mixture (approx 1.5 mL) its pH was adjusted to 7.5 by addition of NH$_4$OH followed by addition of K$_3$Fe(CN)$_6$ solution. The total volume of the 0.01M K$_3$Fe(CN)$_6$ solution used for oxidation was 57 mL. An additional 2 mL of K$_3$Fe(CN)$_6$ solution was added and the mixture was stirred over 30 min (pH=7.5), then the pH was adjusted to 4–5 by addition of AcOH followed by stirring with 5 g of anion exchange resin AG 3-X4, 200–400 mesh, free base form (Bio-Rad) over 30 min. The resin was filtered off, washed with 5% acetic acid (3×100 mL) and combined fractions were lyophilized to give 2 g of white solid.

The crude peptide (approximately 2 g) was purified on a Vydac C-18 column (15μ, 10×30 cm) eluting with a 0–20% over 10 min and 20–55% gradient of 80% acetonitrile in 0.1% TFA over 50 min at a flow rate of 120 mL per min. Fractions were collected, analyzed by HPLC and pure fractions pooled and lyophilized to give 52 mg of white solid. Amino acid analysis: Arg 1.00 (1), Cys 1.67 (2), Gly 2.01 (2), Lys 1.00 (1), Thr 0.86 (1), Trp 0.69 (2). FAB/MS: MH$^+$ 1093.5

EXAMPLE VIII

Arginyl-lysyl-cyclo(cysteinyl-glycyl-glycyl-cysteinyl)-tryptophyl-threonyl-tryptophan-amide (Preferred peptide (7)) (SEQ ID NO:10)

The peptide was prepared on an ABI Model 431A Peptide Synthesizer using Version 1.12 of the standard Boc software. 4-methyl benzhydrylamine resin (0.625 g 0.5 mmol) was used in the synthesis. The final weight of the resin was 1.473 g.

The peptide was cleaved from the resin (1.389 g) using 14 mL of HF and 1.4 mL of anisole for 60 min at 0° C. The resin was washed with ether and the peptide extracted with a 1:1 solution of TFA/CH$_2$Cl$_2$ to give 1.733 g of crude peptide. The high weight is probably due to solvent.

The tryptophans were deformylated by dissolving the peptide into 250 mL of water with 5 mL of piperidine. The solution was stirred at 4° C. for one hour and monitored by HPLC until complete and the solution was lyophilized. The resultant oil was cyclized by dissolving it in 2 liters of aqueous DMSO (10%) and was stirred overnight at room temperature. The reaction was monitored by HPLC and the solution was lyophilized when the reaction was complete.

The crude peptide was purified on a Vydac C-18 column (15μ, 5×25 cm) eluting with a 20–55% gradient of 80% acetonitrile in 0.1% TFA over 120 min at a flow rate of 15 mL per min. Fractions were collected, analyzed by HPLC and pure fractions pooled and lyophilized to give 17 mg. Amino acid analysis: Arg 1.02 (1), Cys (1.55) (2), Gly 1.97 (2), Lys 1.0 (1), Thr 0.90 (1), Trp 0.12 (2). FAB/MS: MH$^+$ 1093

EXAMPLE IX

D-Arginyl-D-lysyl-cyclo(D-cysteinyl-D-alanyl-phenylalanyl-D-cysteinyl)-D-tryptophyl-D-threonyl-D-tryptophyl-D-valine-amide (Preferred peptide (11))

The peptide was prepared on an ABI Model 431A Peptide Synthesizer using Version 1.12 of the standard Boc software.

4-methyl benzhydrylamine resin (625 mg, 0.5 mmol) was used in the synthesis. All Boc-D-amino acids were obtained from Bachem Bioscience, Inc and 2 mmol of each was used in this synthesis. The final weight of the resin was 1.57 g.

The peptide was cleaved from the resin (1.57 g) using 16 mL of HF and 1.6 mL of anisole for 60 min at 0° C. The resin was washed with ether and the peptide extracted with 50% TFA/CH$_2$Cl$_2$ to give 601 mg of crude peptide. The crude peptide was cyclized using air and 2 cm of copper wire in dilute acetic acid (4 mg/mL) which was adjusted to pH 8.5 with concentrated ammonium hydroxide.

The crude peptide (436 mg) was purified on a Vydac C-18 column (15μ, 5×25 cm) eluting with a 25–655 gradient of 80% acetonitrile in 0.1% TFA over 120 min at a flow rate of 15 mL per min. Fractions were collected, analyzed by HPLC and pure fractions pooled and lyophilized to give 14.2 mg. Amino acid analysis: Ala 0.99 (1), Arg 1.01 (1), Lys 1.01 (1), Phe 0.97 (1), Thr 0.90 (1), Trp 1.54 (2), Val 1.03 (1).

EXAMPLE X

D-Arginyl-D-lysyl-cyclo(D-cysteinyl-D-phenylalanyl-glycyl-D-cysteinyl)-D-tryptophyl-D-threonyl-D-tryptophyl-D-valine-amide (Preferred peptide (12))

The peptide was prepared on an ABI Model 431A Peptide Synthesizer using Version 1.12 of the standard Boc software. 4-methyl benzhydrylamine resin (0.625 g, 0.5 mmol) was used in the synthesis. Boc-D-Cys(Mob) (0.682 g, 2 mmol), Boc-D-Arg(Tos) (0.856 g, 2 mmol), Boc-D-Lys(2-Cl-Z) (0.828 g, 0.5 mmol), Boc-D-Thr(Bzl) (0.618 g, 2 mmol), Boc-D-Trp (0.608 g, 2 mmol), Boc-D-Val (0.434 g, 2 mmol), and Boc-D-Phe (0.530 g, 2 mmol) were supplied by Bachem Bioscience. The final weight of the resin was 1.664 g.

The peptide was cleaved from the resin (1.603 g) using 16 mL of HF and 1.6 mL of anisole for 60 min at 0° C. The resin was washed with ether and the peptide extracted with a 1:1 solution of TFA/CH$_2$Cl$_2$ to give 917 mg of crude peptide. The peptide was cyclized by adding 551 mg of peptide (dissolved in 80 mL of 50% acetic acid) to 1600 mL of aqueous 10% DMSO at a pH of 5.5 and stirring the solution overnight. The reaction was monitored by HPLC and lyophilized.

The crude peptide was purified on a Vydac C-18 column (15μ, 5×25 cm) eluting with a 30–50% gradient of 80% acetonitrile in 0.1% TFA over 120 min at a flow rate of 15 mL per min. Fractions were collected, analyzed by HPLC and pure fractions pooled and lyophilized to give 103 mg. Amino acid analysis: Arg 1.01 (1), Cys 1.49 (2), Gly 1.0 (1), Lys 1.0 (1), Phe 1.0 (1), Thr 0.89 (1), Trp 0.48 (2), Val 0.99 (1) FAB/MS: MH$^+$ 1282.5

EXAMPLE XI

D-Arginyl-D-lysyl-cyclo(D-cysteinyl-glycyl-D-phenylalanyl-D-cysteinyl)-D-tryptophyl-D-threonyl-D-tryptophyl-D-valine-amide (Preferred peptide (13))

The peptide was prepared on an ABI Model 431A Peptide Synthesizer using Version 1.12 of the standard Boc software. 4-methyl benzhydrylamine resin (0.625 g, 0.5 mmol) was used in the synthesis. Boc-D-Cys(Mob) (0.682 g, 2 mmol), Boc-D-Arg(Tos) (0.856 g, 2 mmol), Boc-D-Lys(2-Cl-Z) (0.828 g, 0.5 mmol), Boc-D-Thr(Bzl) (0.618 g, 2 mmol), Boc-D-Trp (0.608 g, 2 mmol), Boc-D-Val (0.434 g, 2 mmol), and Boc-D-Phe (0.530 g, 2 mmol) were supplied by Bachem Bioscience. The final weight of the resin was 1.7651 g.

The peptide was cleaved from the resin (1.731 g) using 17 mL of HF and 1.7 mL of anisole for 60 min at 0° C. The resin was washed with ether and the peptide extracted with a 1:1 solution of TFA/CH$_2$Cl$_2$ to give 901 mg of crude peptide. The peptide was cyclized by adding 523 mg of peptide (dissolved in 80 mL of 50% acetic acid) to 1600 mL of aqueous 10% DMSO at a pH of 5.5 and stirring the solution overnight. The reaction was monitored by HPLC and lyophilized.

The crude peptide was purified on a Vydac C-18 column (15μ, 5×25 cm) eluting with a 30–50% gradient of 80% acetonitrile in 0.1% TFA over 120 min at a flow rate of 15 mL per min. Fractions were collected, analyzed by HPLC and pure fractions pooled and lyophilized to give 56 mg. Amino acid analysis: Arg 0.99 (1), Cys 1.42 (2), Gly 1.02 (1), Lys 1.01 (1), Phe 0.99 (1), Thr 0.87 (1), Trp 0.61 (2), Val 1.0 (1) FAB/MS: MH$^+$ 1282.6

EXAMPLE XII

D-Arginyl-D-lysyl-cyclo(D-cysteinyl-glycyl-glycyl-D-cysteinyl)-D-phenylalanyl-D-threonyl-D-tryptophyl-D-valine-amide (Preferred peptide (14))

The peptide was prepared on an ABI Model 431A Peptide Synthesizer using Version 1.12 of the standard Boc software. 4-methyl benzhydrylamine resin (0.625 g) was used in the synthesis. The final weight of the resin was 1.55.

The peptide was cleaved from the resin (1.5 g) using 20 mL of HF and 2 mL anisole for 60 min at 0° C. The resin was washed with ether and ether/CH$_2$Cl$_2$ 1:1 and the peptide extracted with 50% TFA/CH$_2$Cl$_2$ to give 0.74 g of crude peptide. The crude peptide was dissolved in 50 mL DMSO and added to 900 mL H$_2$O and 50 mL DMSO and stored at ambient temperature for 6 hrs. Evaporation under reduced pressure and lyophilization gave 0.62 g.

The crude peptide (0.6 g) was purified on a Vydac C-18 column (15μ, 5×25 cm) eluting with a 20–60% gradient of 80% acetonitrile in 0.1% TFA over 60 min at a flow rate of 100 mL per min. Fractions were collected, analyzed by HPLC and pure fractions pooled and lyophilized to give 31 mg. Amino acid analysis: Arg 0.91 (1), Lys 1.07 (1), Cys ND (2), Gly 1.97 (2), Phe 0.97 (1), Thr 0.99 (1). Trp ND (1), Val 1.02 (1). FAB/MS: MH$^+$ 1153.4 (1153.40)

EXAMPLE XIII

D-Arginyl-D-lysyl-cyclo(D-cysteinyl-glycyl-glycyl-D-cysteinyl)-D-tryptophyl-D-threonyl-D-glutaminyl-D-tryptophyl-D-valine-amide (Preferred peptide (17))

The peptide was prepared on an ABI Model 431A Peptide Synthesizer using Version 1.12 of the standard Boc software. 4-methyl benzhydrylamine resin (0.625 g, 0.5 mmol) was used in the synthesis. The final weight of the resin was 1.64 g.

The peptide was cleaved from the resin (1.64 g) using 16 mL of HF and 1.6 mL anisole for 60 min at 0° C. The resin was washed with ether and ether/CH$_2$Cl$_2$ 1:1 and the peptide extracted with 50% TFA/CH$_2$Cl$_2$ to give 0.72 of crude peptide.

The peptide was cyclized in 1440 mL of 5% DMSO over 48 hrs and lyophilized.

The crude peptide was purified on a Vydac C-18 column (15µ, 5×25 cm) eluting with a 20–60% gradient of 80% acetonitrile in 0.1% TFA over 120 min at a flow rate of 60 mL per min. Fractions were collected, analyzed by HPLC and pure fractions pooled and lyophilized to give 50 mg. Amino acid analysis: Arg 0.98 (1), Cys N.D. (2), Glx 0.98 (1), Gly 2.02 (2), Lys 1.01 (1), Thr 0.88 (1), Trp N.D. (2), Val 1.01 (1) FAB/MS: MH$^+$ 1320.4 (1320.57)

EXAMPLE XIV

D-Arginyl-D-lysyl-cyclo(D-cysteinyl-phenylalanyl-glycyl-D-cysteinyl)-D-tryptophyl-D-threonyl-D-tryptophyl-D-valine-amide (Preferred peptide (18))

The peptide was prepared on an ABI Model 431A Peptide Synthesizer using Version 1.12 of the standard Boc software. 4-methyl benzhydrylamine resin (0.625 g, 0.5 mmol) was used in the synthesis. Boc-D-Cys(Mob) (0.682 g, 2 mmol)., Boc-D-Arg(Tos) (0.856 g, 2 mmol), Boc-D-Thr(Bzl) (0.618 g, 2 mmol), Boc-D-Lys(2-Cl-Z) (0.828 g, 2 mmol), Boc-D-Trp (0.608 g, 2 mmol) and Boc-D-Val (0.434 g, 2 mmol) were supplied by Bachem Bioscience. The final weight of the resin was 1.675 g.

The peptide was cleaved from the resin (1.652 g) using 16 mL of HF and 1.6 mL of anisole for 60 min at 0° C. The resin was washed with ether and the peptide extracted with a 1:1 solution of TFA/CH$_2$Cl$_2$ to give 876 mg of crude peptide. The peptide was cyclized by dissolving 547 mg of peptide into 80 mL of 50% acetic acid. A solution (1600 mL) of 10% DMSO (aqueous) was prepared to which the peptide solution was added. The pH was 5.5 and the solution stirred overnight. The reaction was monitored by HPLC and lyophilized.

The crude peptide was purified on a Vydac C-18 column (15µ, 5×25 cm) eluting with a 30–50% gradient of 80% acetonitrile in 0.1% TFA over 120 min at a flow rate of 15 mL per min. Fractions were collected, analyzed by HPLC and pure fractions pooled and lyophilized to give 75 mg. Amino acid analysis: Arg 0.99 (1), Cys 1.52 (2), Gly 1.01 (1), Lys 1.0 (1), Phe 0.99 (1), Thr 0.90 (1), Trp 0.26 (2), Val 1.0 (1). FAB/MS: MH$^+$ 1282.4

EXAMPLE XV

D-Arginyl-D-lysyl-cyclo(D-cysteinyl-glycyl-phenylalanyl-D-cysteinyl-)-D-tryptophyl-D-threonyl-D-tryptophyl-D-valine-amide (Preferred peptide (19))

The peptide was prepared on an ABI Model 431A Peptide Synthesizer using Version 1.12 of the standard Boc software. 4-methyl benzhydrylamine resin (0.625 g, 0.5 mmol) was used in the synthesis. Boc-D-Cys(Mob) (0.682 g, 2 mmol), Boc-D-Arg(Tos) (0.856 g, 2 mmol), Boc-D-Thr(Bzl) (0.618 g, 2 mmol), Boc-D-Lys(2-Cl-Z) (0.828 g, 2 mmol), Boc-D-Trp (0.608 g, 2 mmol), Boc-D-Val (0.434 g, 2 mmol) were supplied by Bachem Bioscience. The final weight of the resin was 1.835 g.

The peptide was cleaved from the resin (1.788 g) using 18 mL of HF and 1.8 mL of anisole for 60 min at 0° C. The resin was washed with ether and the peptide extracted with a 1:1 solution of TFA/CH$_2$Cl$_2$ to give 948 mg of crude peptide.

The peptide was cyclized by dissolving 547 mg of peptide into 80 mL of 50% acetic acid. A solution (1600 mL) of 10% DMSO (aqueous) was prepared to which the peptide solution was added. The pH was 5.5 and the solution stirred overnight. The reaction was monitored by HPLC and lyophilized when complete.

The crude peptide (approximately 550 mg) was purified on a Vydac C-18 column (15µ, 5×25 cm) eluting with a 30–50% gradient of 809 acetonitrile in 0.1% TFA over 120 min at a flow rate of 15 mL per min. Fractions were collected, analyzed by HPLC and pure fractions pooled and lyophilized to give 59 mg. Amino acid analysis: Arg 1.0 (1), Cys 1.79 (2), Gly 1.03 (1), Lys 1.02 (1), Phe 1.01 (1), Thr 0.90 (1), Trp 0.36 (2), Val 0.94 (1). FAB/MS: MH$^+$ 1282.8

EXAMPLE XVI

D-Arginyl-D-lysyl-D-isoleucyl-glycyl-cyclo(D-cysteinyl-D-isoleucyl-D-tryptophyl-D-cysteinyl)-D-threonyl-D-valine-amide (Preferred peptide (32))

The peptide was prepared on an ABI Model 431A Peptide Synthesizer using Version 1.12 of the standard Boc software. 4-methyl benzhydrylamine resin (0.625 g, 0.5 mmol) was used in the synthesis. The final weight of the resin was 1.5 g.

The peptide was cleaved from the resin (1.5 g) using 15 mL of HF and 1.5 mL of anisole for 60 min at 0° C. The resin was washed with ether and the peptide extracted with TFA/CH$_2$Cl$_2$ (1:1, v/v) (3×15 mL) to give 650 mg of crude peptide. The crude linear peptide (630 mg) was dissolved in 40 mL of 70% HOAc and then added dropwise to the mixture of water (1200 mL), NH$_4$OH (to keep pH approx. 7.5) and 0.01M K$_3$Fe(CN) (approx. 3 mL). After each addition of the linear precursor to the reaction mixture (approx. 1.5 mL) its pH was adjusted to 7.5 by addition of NH$_4$OH followed by addition of K$_3$Fe(CN) solution. The total volume of the 0.01M K$_3$Fe(CN)$_6$ solution used for oxidation was 68 mL. An additional 2 mL of K$_3$Fe(CN)$_6$ solution was added and the mixture was stirred over 30 min (pH=7.5). Next, the pH was adjusted to 4–5 with the addition of acetic acid, followed by stirring with 5 g of anion exchange resin AG 3-X4, 200–400 mesh, free base form (Bio-Rad) over 30 min. The resin was filtered, washed with 5% acetic acid (3×100 mL), and the combined fractions were lyophilized to give 1.8 g of white solid.

The crude peptide (1.8 g) was purified on a Vydac C-18 column (15µ, 10×30 cm) eluting with a 0–20% over 10 min and a 20–55% gradient of 80% acetonitrile in 0.1% TFA over 50 min at a flow rate of 120 mL per min. Fractions were collected, analyzed by HPLC and pure fractions pooled and lyophilized to give 195 mg of white solid. Amino acid analysis: Arg 1.01 (1), Cys 1.28 (2), Gly 1.06 (1), Ile 2.78 (2), Lys 1.04 (1), Thr 0.80 (1), Trp N.D. (1), Val 0.99 (1). FAB/MS: MH$^+$ 1175.5

EXAMPLE XVII

D-Arginyl-D-lysyl-cyclo(D-cysteinyl-delta-aminovaleryl-D-cysteinyl)-D-tryptophyl-D-threonyl-D-tryptophyl-D-valine-amide (Preferred peptide (21))

The peptide was prepared on an ABI Model 431A Peptide Synthesizer using Version 1.12 of the standard Boc software.

4-methyl benzhydrylamine resin (0.625 g, 0.5 mmol) was used in the synthesis. Boc-D-Cys(Mob) (0.682 g, 2 mmol), Boc-D-Arg(Tos) (0.856 g, 2 mmol), Boc-D-Thr(Bzl) (0.618 g, 2 mmol), Boc-D-Lys(2-Cl-Z) (0.828 g, 2 mmol), Boc-D-Trp (0.608, 2 mmol), Boc-D-Val (0.434 g, 2 mmol) were supplied by Bachem Bioscience. Boc-delta- aminovaleric acid (0.434 g, 2 mmol) was supplied by Bachem of California. The final weight of the resin was 1.543 g.

The peptide was cleaved from the resin (1.468 g) using 15 mL of HF and 1.5 mL of anisole for 60 min at 0° C. The resin was washed with ether and the peptide extracted with a 1:1 solution of TFA/CH$_2$Cl$_2$ to give 796 mg of crude peptide. The peptide was cyclized by dissolving 477 mg of peptide into 80 mL of 50% acetic acid. A solution (1600 mL) of 10% DMSO (aqueous) was prepared to which the peptide solution was added. The pH was 5.5 and the solution stirred overnight. The reaction was monitored by HPLC and lyophilized when complete.

The crude peptide (approximately 475 mg) was purified on a Vydac C-18 column (15µ, 5×25 cm) eluting with a 25–45% gradient of 80% acetonitrile in 0.1% TFA over 120 min at a flow rate of 15 mL per min. Fractions were collected, analyzed by HPLC and pure fractions pooled and lyophilized to give 63 mg. Amino acid analysis: Arg 0.99 (1), Cys 1.42 (2), Lys 1.01 (1), Thr 0.88 (1), Trp 0.76 (2), Val 1.0 (1) FAB/MS: MH$^+$ 1177.8

EXAMPLE XVIII

Cyclo(glutamyl-lysyl-isoleucyl-glycyl-glycyl-lysyl)-tryptophyl-threonyl-tryptophyl-valine-amide (Preferred peptide (1)) (SEQ ID NO:5)

The peptide was prepared on an ABI Model 431A Peptide Synthesizer using Version 1.12 of the Standard Boc software. 4-methyl benzhydrylamine resin (0.625 g, 0.5 mmol) was used in the synthesis. Boc-Tryptophan (0.612 g, 2 mmol) supplied by Bachem Bioscience, Boc-Glu(OFm) (0.856 g, 2 mmol) and Boc-Lys(FMOC) (0.936 g, 2 mmol) supplied by Bachem Bioscience of California, were used. The final weight of the resin was 1.743 g. The peptide cyclized by deprotecting the glutamic acid and the lysine with a 20% piperidine (in NMP) solution for 20 min and cyclized with BOP [Benzotriazole-1-yl-oxy-tris-(dimethylamino)-phosphonium-hexaflorophosphate] reagent (0.67 g, 1.5 mmol) and DIEA [N,N Diisopropylethylamine] (0.6 mL, 3 mmol) for 3 hours. The final yield of the resin was 1.290 g.

The peptide was cleaved from the resin (1.128 g) using 11 mL of HF and 1.1 mL of anisole for 60 min at 0° C. The resin was washed with ether and the peptide extracted with a 1:1 solution of CH$_2$Cl$_2$ to give 321 mg of crude peptide.

The crude peptide (321 mg) was purified on a Vydac C-18 column (15µ, 5.0×25 cm) eluting with a 25–65% gradient of 80% acetonitrile in 0.1% TFA over 120 min at a flow rate of 15 mL per min. Fractions were collected, analyzed by HPLC and pure fractions pooled and lyophilized to give 46 mg. Amino acid analysis: Glx 1.0 (1), Gly 2.0 (2), Ile 0.92 (1), Lys 1.97 (2), Thr 0.86 (1), Trp 1.27 (2), Val 1.01 (1). FAB/MS: MH$^+$ 1184.7

EXAMPLE XIX

Arginyl-lysyl-cyclo(diaminopropionyl-glycyl-glycyl-aspartyl)-tryptophyl-threonyl-tryptophyl-valine-amide (Preferred peptide (22)) (SEQ ID NO:4)

The TFA x Gly-Gly-Asp (OFm)-Trp-Thr(Bzl)-Trp-Val-resin was prepared on an ABI Model 431A Peptide Synthesizer using Version 1.12 of the standard Boc software. 4-methyl benzhydrylamine resin (0.625, 0.5 mmol) was used in the synthesis. The final weight of the resin was 1.34 g.

N$^\alpha$-t-Boc-L-2,3-diaminopropionic acid and N$^\alpha$-Boc-N$^\beta$-Fmoc-L-2,3-diaminopropionic acid (N$^\alpha$-Boc-N$^\beta$-Fmoc-Dap) were synthesized as described in C. F. Stanfield et al., Organic Preparations and Procedures Int., 22 (5), 957–603 (1990). The TFA Gly-Gly-Asp(OFm)-Trp-Thr(Bzl)-Trp-Val-resin (1.3 g, approx. 0.5 mmol) was transferred into a manual shaker then neutralized with 10% DIEA/NMP (1×5 min and 1×10 min). N$^\alpha$-Boc-N$^\beta$-Fmoc-L-2,3-diaminopropionic acid (426.5 mg, 1 mmol) was coupled to the resin using BOP Reagent (442.3 mg, 1 mmol) in NMP, in the presence of DIEA (0.35 mL, 2 mmol). The ninhydrine test was negative after a 16 hour single coupling. The peptidyl resin was deprotected with TFA/CH$_2$Cl$_2$, (1:1 v/v) (1×5 min and 1×25 min) then neutralized and coupled with Boc-Lys(2-Cl-Z) (2 mmol) by DCC/HOBT method (negative ninhydrine test after single coupling over 16 hours). The peptidyl resin was deprotected with 50% TFA/CH$_2$Cl$_2$, neutralized and coupled with Boc-Arg(Tos) (2 mmol) by DCC/HOBt method. The protected peptidyl resin was treated with 20% piperidine/NMP solution (1×2 min and 1×20 min). Overnight coupling with BOP Reagent (0.67 g, 1.5 mmol) in NMP with DIEA (0.6 mL, 3 mmol) showed very little progress of the reaction (strong, positive ninhydrine test). The overnight couplings were repeated four times more using BOP Reagent (1.33 g, 3 mmol), HOBt (0.41 g, 3 mmol), DIEA (1.74 mL, 10 mmol) in NMP until negative ninhydrine test. The protected peptidyl resin was treated with TFA/CH$_2$Cl$_2$ (1:1, v/v) for 1×5 min and 1×25 min, washed with several solvents and dried.)

The peptide was cleaved from the resin (1.4 g) using 14 mL of HF and 1.4 mL of anisole for 60 min at 0° C. The resin was washed with ether and the peptide extracted with TFA/CH$_2$Cl$_2$ (1:1, v/v) (3×15 mL) to give 600 mg of crude peptide.

The crude peptide (590 mg) was purified on a Vydac C-18 column (15µ, ×10×30 cm) eluting with a 0–20% gradient over 10 min and 20–50% gradient of 80% acetonitrile in 0.1 TFA over 50 min at a flow rate of 120 mL per min. Fractions were collected, analyzed by HPLC and pure fractions pooled and lyophilized to give 50 mg of white solid. Amino acid analysis: Arg 1.02 (1), Asx 0.94 (1), Gly 2.03 (1), Lys 1.02 (1), Thr 0.82 (1), Trp 1.60 (2), Val 1.00 (1). MH$^+$ 1171.7

EXAMPLE XX

Cyclo(lysyl-lysyl-isoleucyl-glycyl-glycyl-glutamyl)-tryptophyl-threonyl-tryptophyl-valine-amide (Preferred peptide (2)) (SEQ ID NO:6)

The peptide was prepared on an ABI Model 431A Peptide Synthesizer using Version 1.12 of the Standard Boc software. 4-methyl benzhydrylamine resin (0.625 g, 0.5 mmol) was used in the synthesis. Boc-Tryptophan (0.612 g, 2 mmol) supplied by Bachem Bioscience, Boc-Glu(OFm) (0.856 g, 2 mmol) and Boc-Lys(FMOC) (0.936 g, 2 mmol) supplied by Bachem Bioscience of California, were used. The final weight of the resin was 1.783 g. The peptide cyclized by deprotecting the glutamic acid and the lysine with a 20% piperidine (in NMP) solution for 20 min and cyclized with BOP [Benzotriazole-1-yl-oxy-tris-(dimethylamino)-phosphonium-hexafluorophosphate] reagent (0.67 g, 1.5 mmol) and DIEA (N,N-Diisopropylethylamine] (0.6 mL, 3 mmol) for three hours. The final yield of the resin was 1.690 g.

The peptide was cleaved from the resin (1.690 g) using 17 mL of HF and 1.7 mL of anisole for 60 min at 0° C. The resin was washed with ether and the peptide extracted with a 1:1 solution of TFA/CH$_2$CO$_2$ to give 530 mg of crude peptide.

The crude peptide (530 mg) was purified on a Vydac C-18 column (15μ, 5.0×25 cm) eluting with a 30–70% gradient of 80% acetonitrile in 0.1% TFA over 120 min at a flow rate of 15 mL per min. Fractions were collected, analyzed by HPLC and pure fractions pooled and lyophilized to give 104 mg. Amino acid analysis: Glx 1.0 (1), Gly 2.03 (2), Ile 0.95 (1), Lys 1.99 (2), Thr 0.91 (1), Trp 1.34 (2), Val 1.04 (1)

EXAMPLE XXI

Arginyl-lysyl-isoleucyl-cyclo(lysyl-glycyl-isoleucyl-tryptophyl-glutamyl)-tryptophyl-valine-amide (Preferred peptide 31)) (SEQ ID NO:18)

The peptide was prepared on an ABI Model 431 a Peptide Synthesizer using Version 1.12 of the Standard Boc software. 4-methyl benzhydrylamine resin (0.625 g, 0.5 mmol) was used in the synthesis. Boc-Tryptophan (0.612 g, 2 mmol) supplied by Bachem Bioscience, Boc-Glu(OFm) (0.856 g, 2 mmol) and Boc-Lys(FMOC) (0.936 g, 2 mmol) supplied by Bachem Bioscience of California, were used. The final weight of the resin was 1.785 g. The peptide was cyclized by deprotecting the glutamic acid and the lysine with a 20% piperidine (in NMP) solution for 20 min and cyclized with BOP [Benzotriazole-1-yl-oxy-tris-(dimethylamino)-phosphonium-hexafluorophosphate] reagent (0.67 g, 1.5 mmol) and DIEA [N,N Diisopropylethylamine] (0.6 mL, 3 mmol) for three hours. The final yield of the resin was 1.384 g.

The peptide was cleaved from the resin (1.344 g) using 13 mL of HF and 1.3 mL of anisole for 60 min at 0° C. The resin was washed with ether and the peptide extracted with a 1:1 solution of TFA/CH$_2$Cl$_2$ to give 633 mg of crude peptide.

The crude peptide (633 mg) was purified on a Vydac C-18 column (15μ, 5×25 cm) eluting with a 25–65% gradient of 80% acetonitrile in 0.1% TFA over 120 min at a flow rate of 15 mL per min. Fractions were collected, analyzed by HPLC and pure fractions pooled and lyophilized to give 178 mg. Amino acid analysis: Arg 1.0 (1), Glx 0.98 (1), Gly 1.01 (1), Ile 1.86 (2), Lys 1.99 (2), Trp 0.99 (2), Val 1.01 (1). FAB/MS: MH$^+$ 1295.5

EXAMPLE XXII

Arginyl-lysyl-cyclo(D-penicillamyl-glycyl-glycyl-cysteinyl)-tryptophyl-threonyl-tryptophyl-valine-amide (Preferred peptide (23)) (SEQ ID NO:13)

The peptide was prepared on an ABI Model 431A Peptide Synthesizer using Version 1.12 of the standard Boc software. 4-methyl benzhydrylamine resin (0.625 g, 0.5 mmol) was used in the synthesis. Boc-S(p-methoxybenzyl)-D-penicillamine (0.738 g, 2 mmol) by Bachem of California. The final weight of the resin was 1.838 g.

The peptide was cleaved from the resin (1.751 g) using 17 mL of HF and 1.7 mL of anisole for 60 min at 0° C. The resin was washed with ether and the peptide extracted with a 1:1 solution of CH$_2$Cl$_2$ to give 933 mg of crude peptide. The peptide was deformylated with a 2% piperidine (aqueous) solution for one hour at 4° C. and then lyophilized. The dry product was then cyclized in 2 liters of 8% DMSO (aqueous) at pH 6.0 overnight. The liquid was lyophilized and then purified.

The crude peptide was purified on a Vydac C-18 column (15μ, 5×25 cm) eluting with a 30–50% gradient of 80% acetonitrile in 0.1% TFA over 120 min at a flow rate of 15 mL per min. Fractions were collected, analyzed by HPLC and pure fractions pooled and lyophilized to give 139 mg. Amino acid analysis: Arg 1.0 (1), Gly 2.06 (2), Glys 0.97 (1), Thr 0.85 (1), Trp 0.0 (2), Val 1.0 (1). FAB/MS: MH$^+$ 1220.5

EXAMPLE XXIII

Arginyl-lysyl-cyclo(D-penicillamyl-glycyl-glycyl-D-penicillamyl)-tryptophyl-threonyl-tryptophyl-valine-amide (Preferred peptide (24)) (SEQ ID NO:14)

The peptide was prepared on an ABI Model 431A Peptide Synthesizer using Version 1.12 of the standard Boc software. 4-methyl benzhydrylamine resin (0.625 g, 0.5 mmol) was used in the synthesis. Boc-S(p-methoxybenzyl)-D-penicillamine (0.738 g, 2 mmol) was supplied by Bachem of California. The final weight of the resin was 1.715 g.

The peptide was cleaved from the resin (1.715 g) using 17 mL of HF and 1.7 mL of anisole for 60 min at 0° C. The resin was washed with ether and the peptide extracted with a 1:1 solution of TFA/CH$_2$Cl$_2$ to give 1.148 g of crude peptide. The peptide was deformylated in a 2% piperidine (aqueous) solution for one hr at 4° C. The solution was lyophilized and the dry product was cyclized by dissolving the peptide in 1600 mL of a 10% DMSO (aqueous) solution, pH'ed to 6.0, and stirred overnight. The solution was lyophilized and then purified.

The crude peptide was purified on a Vydac C-18 column (15μ, 5×25 cm) eluting with a 30–60% gradient of 80% acetonitrile in 0.1% TFA over 120 min at a flow rate of 15 mL per min. Fractions were collected, analyzed by HPLC and pure fractions pooled and lyophilized to give 86 mg. Amino acid analysis: Arg 1.01 (1), Gly 2.06 (2), Lys 1.0 (1), Thr 0.84 (1), Trp 0.22 (2), Val 0.97 (1). FAB/MS: MH$^+$ 1248.6

EXAMPLE XXIV

D-arginyl-D-lysyl-cyclo(D-cysteinyl-glycyl-glycyl-D-cysteinyl)-D-tryptophyl-D-threonyl-D-tryptophyl-D-valine-amide (Preferred peptide (25))

The peptide was prepared on an ABI Model 431A Peptide Synthesizer using Version 1.12 of the standard Boc software. 4-methyl benzhydrylamine resin (0.625 g, 0.5 mmol) was used in the synthesis. Boc-D-Cys(Mob) (0.682 g, 2 mmol), Boc-D-Arg(Tos) (0.856 g, 2 mmol), Boc-D-Lys(2-Cl-Z) (0.828 g, 2 mmol), Boc-D-Thr(Bzl) (0.618 g, 2 mmol), Boc-D-Trp(CHO) (0.664 g, 2 mmol), and Boc-D-Val (0.434 g, 2 mmol) were supplied by Bachem Bioscience. The final weight of the resin was 1.682 g.

The peptide was cleaved from the resin (1.600 g) using 16 mL of HF and 1.6 mL of anisole and 1.6 mg of DTT for 60 min at 0° C. The resin was washed with ether and the peptide extracted with a 1:1 solution of TFA/CH$_2$Cl$_2$ to give 1.748 g of crude peptide. The peptide was deformylated by using an aqueous 2% piperidine solution and stirred for one and one-half hours at 4° C. After deformylation, 100 ml of DMSO and enough water added to bring the volume to 1 liter. The pH was adjusted with acetic acid to get a pH of 6.5 and the solution was stirred overnight to complete the cyclization.

The crude peptide was purified on a Vydac C-18 column (15μ, 5×25 cm) eluting with a 20–55% gradient of 80% acetonitrile in 0.1% TFA over 120 min at a flow rate of 15 mL per min. Fractions were collected, analyzed by HPLC and pure fractions pooled and lyophilized to give 40 mg. Amino acid analysis: Arg 1.0 (1), Cys 1.71 (2), Gly 2.01 (2), Lys 1.01 (1), Thr 0.89 (1), Trp 0.66 (2), Val 0.99 (1). FAB/MS: MH$^+$ 1192.7

EXAMPLE XXV

Cyclo(cysteinyl-arginyl-glycyl-glycyl-cysteinyl)-tryptophyl-threonyl-tryptophyl-valine-amide (Preferred peptide (6)) (SEQ ID NO:9)

The peptide was prepared on an ABI Model 431A Peptide Synthesizer using Version 1.12 of the standard Boc software. 4-methyl benzhydrylamine resin (0.625 g, 0.5 mmol) was used in the synthesis. The final weight of the resin was 1.45 g.

The peptide was cleaved from the resin (1.4 g) using 14 mL of HF, DTT (1.0 g) and 1.4 mL of anisole for 60 min at 0° C. The resin was washed with ether and the peptide extracted with TFA/CH$_2$Cl$_2$ (1:1, v/v) (3×15 mL) to give 830 mg of crude peptide. The crude peptide (410 mg) was dissolved in 20% DMSO/water solution (1.0 L), stirred overnight and lyophilized yielding 1.6 g of yellow oil.

The crude peptide (1.6 g) was purified in two runs on a Vydac C-18 column (15μ, 10×30 cm) eluting with a a) 0–25%; b) 25–55% gradient of 80% acetonitrile in 0.1% TFA over 60 min at a flow rate of 120 mL per min. Fractions were collected, analyzed by HPLC and pure fractions pooled and lyophilized to give 22 mg of white solid. Amino acid analysis: Arg 1.03 (1), Cys 1.84 (2), Gly 1.94 (2), Thr 0.94 (1), Trp 0.85 (2), Val 1.00 (1). FAB/MS: MH$^+$1064.4

EXAMPLE XXVI

Lysyl-cyclo(cysteinyl-glycyl-glycyl-cysteinyl)-tryptophyl-threonyl-tryptophyl-valine-amide (Preferred peptide (27)) (SEQ ID NO:15)

The peptide was prepared on an ABI Model 431A Peptide Synthesizer using Version 1.12 of the standard Boc software. 4-methyl benzhydrylamine resin (0.625 g, 0.5 mmol) was used in the synthesis. Boc-Tryptophan (0.608 g, 2 mmol) was supplied by Bachem Bioscience. The final weight of the resin was 1.580 g.

The peptide was cleaved from the resin (1.488 g) using 15 mL of HF and 1.5 mL of anisole for 60 min at 0° C. The resin was washed with ether and the peptide extracted with a 1:1 solution of TFA/CH$_2$Cl$_2$ to give 810 mg of crude peptide. The peptide was cyclized by using two methods. The first used 38 mL of 0.01M K$_3$Fe(CN)$_6$ and 59 mL of ammonium hydroxide in a total volume of 1 liter of deionized water. The peptide (350 mg) was dissolved in acetic acid and added dropwise. When the reaction was complete, the excess ferricyanide was adsorbed onto 8 g of Bio-Rad Analytical Grade Anion Exchange Resin and the resultant solution was filtered and lyophilized.

The second method dissolved 350 mg of peptide into 40 mL of 50% acetic acid. A solution (800 mL) of 10% DMSO (aqueous) was prepared to which the peptide solution was added. The pH was 5.5 and the solution stirred overnight. The reaction was monitored by HPLC and lyophilized when complete.

The crude peptide (700 mg) was purified on a Vydac C-18 column (15μ, 5×25 cm) eluting with a 25–45% gradient of 80% acetonitrile in 0.1% TFA over 120 min at a flow rate of 15 mL per min. Fractions were collected, analyzed by HPLC and pure fractions pooled and lyophilized to give 76 mg. Amino acid analysis: Cys 1.85 (2), Gly 2.16 (2), Lys 1.01 (1), Thr 0.85 (1), Trp 0.23 (2), Val 1.06 (1). FAB/MS: MH$^+$ 1036.4

EXAMPLE XXVII

D-Lysyl-cyclo(D-cysteinyl-glycyl-glycyl-D-cysteinyl)-D-tryptophyl-D-threonyl-D-tryptophyl-D-valine-amide (Preferred peptide (26))

The peptide was prepared on an ABI Model 431A Peptide Synthesizer using Version 1.12 of the standard Boc software. 4-methyl benzhydrylamine resin (0.625 g, 0.5 mmol) was used in the synthesis. The final weight of the resin was 1.45 g.

The peptide was cleaved from the resin (1.4 g) using 14 mL of HF and 1.4 mL of anisole for 60 min at 0° C. The resin was washed with ether and the peptide extracted with TFA/CH$_2$Cl$_2$ (1:1, v:v) (3×15 mL) to give 582 mg of crude peptide. The crude linear peptide (580 mg) was dissolved in 80 mL of 75% HOAc and then added dropwise to the mixture of water (1200 mL), NH$_4$OH (to keep pH approx. 7.5) and 0.01M K$_3$Fe(CN)$_6$ (approx. 3 mL). After each addition of the linear precursor to the reaction mixture (approx. 1.5 mL) its pH was adjusted to 7.5 by addition of NH$_4$OH followed by addition of K$_3$Fe(CN)$_6$ solution. The total volume of the 0.01M K$_3$Fe(CN)$_6$ solution used for oxidation was 66 mL. The 2 mL of K$_3$Fe(CN)$_6$ solution was added extra and the mixture was stirred over 30 min (pH= 7.5), then the pH was adjusted to 4–5 by addition of HOAc followed by stirring with 5 g of anion exchange resin AG 3-X4, 200–400 mesh, free base form (Bio-Rad) over 30 min. The resin was filtered off, washed with 5% acetic acid (3×100 mL) and combined fractions were lyophilized to give 2 g of white solid.

The crude peptide (2 g of white solid) was purified on a Vydac C-18 column (15μ, 10×30 cm) eluting with a a) 0–20%; b)20–55% gradient of 806 acetonitrile in 0.1% TFA over 60 min at a flow rate of 120 mL per min. Fractions were collected, analyzed by HPLC and pure fractions pooled and lyophilized to give 95 mg of white solid. Amino acid analysis: Cys (O$_3$H) 1.67 (2), Gly 2.05 (2), Lys 1.01 (1), Thr 0.87 (1), Trp 0.72 (2), Val 0.96 (1). FAB/MS: MH$^+$ 1036.6

EXAMPLE XXVIII

Cyclo(cysteinyl-glycyl-glycyl-cysteinyl)-tryptophyl-threonyl-tryptophyl-valine-amide (Preferred peptide (29)) (SEQ ID NO:16)

The peptide was prepared on an ABI Model 431A Peptide Synthesizer using Version 1.12 of the standard Boc software. 4-methyl benzhydrylamine resin (0.625 g, 0.5 mmol) was used in the synthesis. Boc-Trp (0.608 g, 2 mmol) was supplied by Bachem Bioscience. The final weight of the resin was 1.384 g.

The peptide was cleaved from the resin (1.384 g) using 14 mL of HF and 1.4 mL of anisole for 60 min at 0° C. The resin was washed with ether and the peptide extracted with a 1:1 solution of TFA/CH$_2$Cl$_2$ to give 535 mg of crude peptide.

The peptide was cyclized by adding 436 mg of peptide (dissolved in 80 mL of 50% acetic acid) to 1600 mL of aqueous DMSO (10%) at a pH of 5.5 and stirring overnight. The reaction was monitored by HPLC and lyophilized.

The crude peptide was purified on a Vydac C-18 column (15μ, 5×25 cm) eluting with a 30–50% gradient of 80% acetonitrile in 0.1% TFA over 120 min at a flow rate of 15 mL per min. Fractions were collected, analyzed by HPLC and pure fractions pooled and lyophilized to give 37 mg. Amino acid analysis: Cys 1.10 (2), Gly 2.10 (2), Thr 0.92 (1), Trp 0.31 (2), Val 0.95 (1). FAB/MS: MH$^+$ 908.2

EXAMPLE XXIX

Cyclo(D-cysteinyl-glycyl-glycyl-D-cysteinyl)-D-tryptophyl-D-threonyl-D-tryptophyl-D-valine-amide (Preferred peptide (28))

The peptide was prepared on an ABI Model 431A Peptide Synthesizer using Version 1.12 of the standard Boc software. 4-methyl benzhydrylamine resin (0.625 g, 0.5 mmol) was used in the synthesis. The final weight of the resin was 1.3 g.

The peptide was cleaved from the resin (1.3 g) using 13 mL of HF and 1.3 mL of anisole for 60 min at 0° C. The resin was washed with ether and the peptide extracted with TFA/CH$_2$Cl$_2$ (1:1, v/v) (3×15 mL) to give 0.59 g of crude peptide.

The crude linear peptide (590 mg) was dissolved in 50 mL of 70% HOAc and then added dropwise to the mixture of water (1200 mL), NH$_4$OH (to keep pH approx. 7.5) and 0.01M K$_3$Fe(CN)$_6$ solution. The total volume of the 0.01M K$_3$Fe(CN)$_6$ solution used for oxidation was 63 mL. The 2 mL of K$_3$Fe(CN)$_6$ solution was added extra and the mixture was stirred over 30 min (pH=7.5), then the pH was adjusted to 4–5 by addition of HOAc followed by stirring with 5 g of anion exchange resin AG 3-X4, 200–400 mesh, free base form (Bio-Rad) over 30 min. The resin was filtered off, washed with 5% acetic acid (3×100 mL and combined fractions were lyophilized to give 1.7 g of white solid.

The crude peptide (approximately 1.7 g) was purified on a Vydac C-18 column (15μ, 10×30 cm) eluting with 0–20% over 10 min and 20–55% gradient of 80% acetonitrile in 0.1% TFA over 50 min at a flow rate of 120 mL per min. Fractions were collected, analyzed by HPLC and pure fractions pooled and lyophilized to give 20 mg of white solid. Amino acid analysis: Cys 1.01 (2), Gly 1.96 (2), Thr 0.87 (1), Trp 0.51 (2), Val 1.02 (1). FAR/MS: MH$^+$ 908.3

EXAMPLE XXX

D-arginyl-D-lysyl-cyclo(D-cysteinyl-D-prolyl-glycyl-D-cysteinyl)-D-tryptophyl-D-threonyl-D-tryptophyl-D-valine-amide (Preferred peptide (15))

The peptide was prepared on an ABI Model 431A Peptide Synthesizer using Version 1.12 of the standard Boc software. 4-methyl benzhydrylamine resin (0.625 g, 0.5 mmol) was used in the synthesis. Boc-D-Cys(Mob) (0.682 g, 2 mmol), Boc-D-Arg(Tos) (0.856 g, 2 mmol) Boc-D-Thr(Bzl) (0.618 g, 2 mmol), Boc-D-Lys(2-Cl-Z) (0.828 g, 2 mmol), Boc-D-Trp (0.608 g, 2 mmol), Boc-D-Pro (0.430 g, 2 mmol), and Boc-D-Val (0.434 g, 2 mmol) were supplied by Bachem Bioscience. The final weight of the resin was 1.858 g.

The peptide was cleaved from the resin (1.858 g) using 18 mL of HF and 1.8 mL of anisole for 60 min at 0° C. The resin was washed with ether and the peptide extracted with a 1:1 solution of CH$_2$Cl$_2$ to give 795 mg of crude peptide. The crude linear peptide (493 mg) was dissolved in 50 mL of 40% HOAc and then added dropwise to the mixture of water (1400 mL), NH$_4$OH (to keep pH approx. 7.5) and 0.01M K$_3$Fe(CN)$_6$ (approx. 3 mL). After each addition of the linear precursor to the reaction mixture, the pH was adjusted to 7.5 by addition of NH$_4$OH followed by addition of K$_3$Fe(CN)$_6$ solution. The total volume of the 0.01M K$_3$Fe(CN)$_6$ solution used for oxidation was 50 mL. The mixture was stirred over 30 min (pH=7.5). The pH was lowered with the addition of HOAc followed by stirring with 20 g of anion exchange resin AG 3-X4, 200–400 mesh, free base form (Bio-Rad) over 30 min. The resin was filtered off and the liquid was lyophilized and the peptide was directly purified.

The crude peptide was purified on a Vydac C-18 column (15μ, 5×25 cm) eluting with a 25–45% gradient of 80% acetonitrile in 0.1% TFA over 120 min at a flow rate of 15 mL per min. Fractions were collected, analyzed by HPLC and pure fractions pooled and lyophilized to give 93 mg. Amino acid analysis: Arg 1.17 (1), Cys 1.75 (2), Gly 1.02 (1), Lys 0.99 (1), Pro 1.18 (1), Thr 0.87 (1), Trp 1.66 (2), Val 1.01 (1).

EXAMPLE XXXI

D-arginyl-D-lysyl-cyclo(D-cysteinyl-D-glycyl-D-prolyl-D-cysteinyl)-D-tryptophyl-D-threonyl-D-tryptophyl-D-valine-amide (Preferred peptide (16))

The peptide was prepared on an ABI Model 431A Peptide Synthesizer using Version 1.12 of the standard Boc software. 4-methyl benzhydrylamine resin (0.625 g, 0.5 mmol) was used in the synthesis. Boc-D-Cys(Mob) (0.682 g, 2 mmol), Boc-D-Arg(Tos) (0.856 g, 2 mmol), Boc-D-Thr(Bzl) (0.618 g, 2 mmol), Boc-D-Lys(2-Cl-Z) (0.828 g, 2 mmol), Boc-D-Trp (0.608 g, 2 mmol), Boc-D-Pro (0.430 g, 2 mmol), and Boc-D-Val (0.434 g, 2 mmol) were supplied by Bachem Bioscience. The final weight of the resin was 1.428 g.

The peptide was cleaved from the resin (1.428 g) using 14 mL of HF and 1.4 mL of anisole for 60 min at 0° C. The resin was washed with ether and the peptide extracted with a 1:1 solution of TFA/CH$_2$Cl$_2$ to give 886 mg of crude peptide. The crude linear peptide (482 mg) was dissolved in 50 mL of 40% HOAc and then added dropwise to the mixture of water (1400 mL), NH$_4$OH (to keep pH approx. 7.5) and 0.01M K$_3$Fe(CN)$_6$ (approx. 3 mL). After each addition of the linear precursor to the reaction mixture, the pH was adjusted to 7.5 by addition of NH$_4$OH followed by addition of K$_3$Fe(CN)$_6$ solution. The total volume of the 0.01M K$_3$Fe(CN)$_6$ solution used for oxidation was 35 mL. The mixture was stirred over 30 min (pH=7.5). The pH was lowered with the addition of HOAc followed by stirring with 12 g of anion exchange resin AG 3-X4, 200–400 mesh, free base form (Bio-Rad) over 30 min. The resin was filtered off and the peptide was directly purified.

The crude peptide was purified on a Vydac C-18 column (15μ, 10×30 cm) eluting with a 20–50% gradient of 80% acetonitrile in 0.1% TFA over 60 min at a flow rate of 120 mL per min. Fractions were collected, analyzed by HPLC and pure fractions pooled and lyophilized to give 33 mg. Amino acid analysis: Arg 0.98 (1), Cys 1.50 (2), Gly 1.02 (1), Lys 0.98 (1), Pro 1.31 (1), Thr 0.90 (1), Trp 1.66 (2), Val 1.02 (1).

EXAMPLE XXXII

D-arginyl-D-lysyl-cyclo(D-cysteinyl-glycyl-prolyl-D-cysteinyl)-D-tryptophyl-D-threonyl-D-tryptophyl-D-valine-amide (Preferred peptide (20))

The peptide was prepared on an ABI Model 431A Peptide Synthesizer using Version 1.12 of the standard Boc software.

4-methyl benzhydrylamine resin (0.625 g, 0.5 mmol) was used in the synthesis. Boc-D-Cys(Mob) (0.682 g, 2 mmol), Boc-D-Arg(Tos) (0.856 g, 2 mmol) Boc-D-Thr(Bzl) (0.618 g, 2 mmol), Boc-D-Lys(2-Cl-Z) (0.828 g, 2 mmol), Boc-D-Trp (0.608 g, 2 mmol), and Boc-D-Val (0.434 g, 2 mmol) were supplied by Bachem Bioscience. The final weight of the resin was 1.605 g.

The peptide was cleaved from the resin (1.605 g) using 16 mL of HF and 1.6 mL of anisole for 60 min at 0° C. The resin was washed with ether and the peptide extracted with a 1:1 solution of TFA/CH$_2$Cl$_2$ to give 671 mg of crude peptide. The crude linear peptide (488 mg) was dissolved in 50 mL of 40% HOAc and then added dropwise to the mixture of water (1400 mL), NH$_4$OH (to keep pH approx. 7.5) and 0.01M K$_3$Fe(CN)$_6$ (approx. 3 mL). After each addition of the linear precursor to the reaction mixture, the pH was adjusted to 7.5 by addition of NH$_4$OH followed by addition of K$_3$Fe(CN)$_6$ solution. The total volume of the 0.01M K$_3$Fe(CN)$_6$ solution used for oxidation was 50 mL. The mixture was stirred over 30 min (pH=7.5). The pH was lowered with the addition of HOAc followed by stirring with 12 g of anion exchange resin AG 3-X4, 200–400 mesh, free base form (Bio-Rad) over 30 min. The resin was filtered off, the liquid lyophilized, and the residue was directly purified.

The crude peptide was purified on a Vydac C-18 column (15μ, 5×25 cm) eluting with a 25–45% gradient of 80% acetonitrile in 0.1% TFA over 120 min at a flow rate of 15 mL per min. Fractions were collected, analyzed by HPLC and pure fractions pooled and lyophilized to give 70 mg. Amino acid analysis: Arg 0.99 (1), Cys 1.69 (2), Gly 1.02 (1), Lys 0.99 (1), Pro 1.20 (1), Thr 0.91 (1), Trp 1.71 (2), Val 1.01 (1).

EXAMPLE XXXIII

D-arginyl-cyclo(D-cysteinyl-D-isoleucyl-glycyl-D-cysteinyl)-D-isoleucyl-D-tryptophyl-D-threonyl-D-tryptophyl-D-valine-amide (Preferred peptide (4))

The peptide was prepared on an ABI Model 431A Peptide Synthesizer using Version 1.12 of the standard Boc software. 4-methyl benzhydrylamine resin (625 mg, 0.5 mmol) was used in the synthesis. The final weight of the resin was 1.7 g.

The peptide was cleaved from the resin (1.7 g) using 17 mL of HF and 1.7 mL of anisole for 60 min at 0° C. The resin was washed with ether and the peptide extracted with 30% acetic acid to give 522 mg of crude peptide. The crude peptide (200 mg) was cyclized by dissolving the peptide in 400 mL of aqueous DMSO at pH 7.5 and stirred overnight. The solution was lyophilized.

The crude peptide (100 mg) was purified on a Vydac C-18 column (15μ, 5×25 cm) eluting with a 37–53% gradient of 80% acetonitrile in 0.1% TFA over 120 min at a flow rate of 15 mL per min. Fractions were collected, analyzed by HPLC and pure fractions pooled and lyophilized to give 43 mg of pure peptide. Amino acid analysis: Arg 1.04 (1), Cys 1.46 (2), Gly 1.03 (1), Ile 1.78 (2), Thr 0.89 (1), Trp 1.99 (2), Val 1.04 (1). FAB/MS: MH$^+$ 1233.5

EXAMPLE XXXIV

D-Arg-Lys-cyclo(D-Cys-Gly-Phe-D-Cys)-D-Trp-D-Thr-D-Trp-D-Val-NH$_2$ (Preferred Peptide (34))

The peptide was prepared on an ABI Model 431A Peptide Synthesizer using Version 1.12 of the standard BOC software. 4-methyl benzhydrylamine resin (0.625 g, 0.5 mmol) was used in the synthesis. Boc-D-Cys(MOB)-OH (MW 341.43, 0.682 g, 2 mmol), BOC-D-Arg (Tos)-OH (MW 428.5, 0.856 g, 2 mmol), Boc-D-Thr-(Bzl)-OH (MW 309.37, 0.618 g, 2 mmol), Boc-D-Trp-OH (MW 304.37, 0.608 g, 2 mmol) and Boc-D-Val-OH (MW 217.27, 0.434 g, 2 mmol) were supplied by Bachem Bioscience. The final weight of the resin was 1.834 g.

The peptide was cleaved from the resin (1.728 g) using 17 mL of HF and 1.7 mL of anisole for 60 min at 0° C. The resin was washed with ether and the peptide extracted with a 1:1 solution of TFA:DCM to give 1.325 g of crude peptide. The crude linear peptide (870 mg) was dissolved in 200 mL of 40% AcOH and then added dropwise to the mixture of water (2800 mL), NH$_4$OH (to keep pH approx. 7.5) and 0.01M K$_3$Fe(CN)$_6$ (approx. 3 mL). After each addition of the linear precursor to the reaction mixture (approx. 1.5 mL), its pH was adjusted to 7.5 by addition of NH$_4$OH followed by addition of K$_3$Fe(CN)$_6$ solution. The total volume of the 0.01M K$_3$Fe(CN)$_6$ solution used for oxidation was 24 mL. The mixture was stirred for 30 min (pH=7.5), then the pH was lowered with the addition of AcOH, followed by stirring with 5 g of anion exchange AG 3-X4, 100–200 mesh, free base form (Bio-Rad) over 30 min. The resin was filtered and the solution lyophilized, then directly purified.

The crude peptide was purified on a Vydac C-18 column (15μ, 5×25 cm) eluting with a 35–60% gradient of 80% acetonitrile in 0.1% TFA over 120 min at a flow rate of 15 mL per min. Fractions were collected, analyzed by HPLC and pure fractions pooled and lyophilized to give 19 mg.

Amino acid analysis: Arg 0.98 (1), Cys 0.50 (2), Gly 1.19 (1), Lys 0.98 (1), Phe 0.85 (1), Thr 0.89 (1), Trp 2.22 (2), Val 1.01 (1).

EXAMPLE XXXV

D-Arg-D-Lys-cyclo(Cys-Gly-Phe-D-Cys)-D-Trp-D-Thr-D-Trp-D-Val-NH$_2$ (Preferred Peptide (35))

The peptide was prepared on an ABI Model 431A Peptide Synthesizer using Version 1.12 of the standard BOC software. 4-methyl benzhydrylamine resin (0.625 g, 0.5 mmol) was used in the synthesis. Boc-D-Cys(MOB)-OH (MW 341.43, 0.682 g, 2 mmol), BOC-D-Arg (Tos)-OH (MW 428.5, 0.856 g, 2 mmol), Boc-D-Thr-(Bzl)-OH (MW 309.37, 0.618 g, 2 mmol), Boc-D-Lys (2-Cl-Z)-OH (MW 414.89, 0.828 g 2 mmol), Boc-D-Trp-OH (MW 304.37, 0.608 g, 2 mmol) and Boc-D-Val-OH (MW 217.27, 0.434 g, 2 mmol) were supplied by Bachem Bioscience. The final weight of the resin was 1.710 g.

The peptide was cleaved from the resin (1.594 g) using 16 mL of HF and 1.6 mL of anisole for 60 min at 0° C. The resin was washed with ether and the peptide extracted with a 1:1 solution of TFA:DCM to give 704 mg of crude peptide. The crude linear peptide (457 mg) was dissolved in 200 mL of 40% AcOH and then added dropwise to the mixture of water (2800 mL), NH$_4$OH (to keep pH approx. 7.5) and 0.01M K$_3$Fe(CN)$_6$ (approx. 3 mL). After each addition of the linear precursor to the reaction mixture (approx. 1.5 mL), its pH was adjusted to 7.5 by addition of NH$_4$OH followed by addition of K$_3$Fe(CN)$_6$ solution. The total volume of the 0.01M K$_3$Fe(CN)$_6$ solution used for oxidation was 38 mL. The mixture was stirred for 30 min (pH=7.5), then the pH was lowered with the addition of AcOH, followed by stirring with 5 g of anion exchange AG 3-X4, 100–200 mesh, free base form (Bio-Rad) over 30 min. The resin was filtered and the solution lyophilized, then directly purified.

The crude peptide was purified on a Vydac C-18 column (15μ, 5×25 cm) eluting with a 30–50% gradient of 80% acetonitrile in 0.1 TFA over 120 min at a flow rate of 15 mL per min. Fractions were collected, analyzed by HPLC and pure fractions pooled and lyophilized to give 38 mg.

Amino acid analysis: Arg 0.95 (1), Cys 2.45 (2), Gly 1.17 (1), Lys 0.94 (1), Phe 0.98 (1), Thr 0.74 (1), Trp 2.73 (2), Val 0.97 (1).

EXAMPLE XXXVI

D-Arg-D-Lys-cyclo(D-Cys-Gly-(3,4-dehydro-D-Pro)-D-Cys)-D-Trp-D-Thr-D-Trp-D-Val-NH$_2$ (Preferred Peptide (36))

The peptide was prepared on an ABI Model 431A Peptide Synthesizer using Version 1.12 of the standard BOC software. 4-methyl benzhydrylamine resin (0.56 g, 0.5 mmol and Boc-3,4-dehydro-DL-proline (Centocor Notebook 2453-135) were used in the synthesis. The final weight of the resin was 1.38 g.

The peptide was cleaved from the resin (1.38 g) using 14 mL of HF and 1.4 mL of anisole for 60 min at 0° C. The resin was washed with ether and the peptide extracted with TFA/DCM (1:1, v/v) (3×15 mL) to give 760 mg of crude peptide. The crude linear peptide (760 mg) was dissolved in 45 mL of 60% AcOH and then added dropwise to the mixture of water (1200 mL), NH$_4$OH (to keep pH approx. 7.5) and 0.01M K$_3$Fe(CN)$_6$ (approx. 3 mL). After each addition of the linear precursor to the reaction mixture (approx. 1.5 mL) its pH was adjusted to 7.5 by addition of NH$_4$OH followed by addition of K$_3$Fe(CN)$_6$ solution. The total volume of the 0.01M K$_3$Fe(CN)$_6$ solution used for oxidation was 50 mL. The 2 mL of K$_3$Fe(CN)$_6$ solution was added extra and the mixture was stirred over 20 min (pH= 7.5), then the pH was adjusted to 4–5 by addition of AcCH followed by stirring with 5 g of anion exchange AG 3-X4, 200–400 mesh, free base form (Bio-Rad) over 30 min. The resin was filtered off, washed with 5% acetic acid (3×100 mL) and combined fractions (approx. 1800 mL) were loaded onto a Vydac C-18 column (15μ, 10×30 cm) eluting with a 30–70% gradient of 80% ethanol in 0.1% TFA over 120 min at a flow rate of 60 mL per min. Fractions were collected, analyzed by HPLC and the fractions containing both diastereoisomeric peptides pooled, evaporated to approx. 50 mL and lyophilized to give 67 mg of white solid. The diastereoisomers were separated in three runs on a Vydac C-18 column, 10μ, 2.2×25 cm, eluting with a 15–55% gradient of 80% ethanol in 0.1% TFA over 60 min at a flow rate of 10 mL per min. Fractions were collected, analyzed by HPLC and pure fractions pooled, evaporated to approx. 30 mL and lyophilized to give 23 mg of white solid. For identification of the separated diastereoisomers the CEN 686 (Centocor Notebook 2453-126) was used as the reference compound (rk-cyclo(cG-(3,4-dehydro-L-Pro)-c)wtwv-NH$_2$.

Amino acid analysis: Arg 0.99 (1), Cys 2.42 (2), Gly 1.08 (1), Lys 0.98 (1), Pro 0.28, Thr 0.66, (1), Trp 1.34 (2), Val 0.95 (1).

FAB/MS: MH$^+$ 1231.2

EXAMPLE XXXVII

D-Arg-D-Lys-cyclo(D-Cys-Ala-Phe-D-Cys)-D-Trp-D-Thr-D-Trp-D-Val-NH$_2$ (Preferred Peptide (37))

The peptide was prepared on an ABI Model 431A Peptide Synthesizer using Version 1.12 of the standard BOC software. 4-methyl benzhydrylamine resin (0.625 g, 0.5 mmol) was used in the synthesis. All the D-Boc-amino acids used were purchased from Bachem Bioscience, Inc. The final weight of the resin was 1.50 g.

The peptide was cleaved from the resin (1.50 g) using 15 mL of HF and 1.5 mL of anisole for 60 min at 0° C. The resin was washed with ether and the peptide extracted with 50% TFA in DCM to give 522 mg of crude peptide. The peptide (522 mg) was cyclized with air in the presence of Cu wire (5 cm) in 550 mL of ammonium acetate, pH 8.5 for 22 hours then lyophilized to give 411 mg.

The crude peptide (411 mg) was purified on a Vydac C-18 column (15μ, 5×25 cm) eluting with a 30–70% gradient of 80% acetonitrile in 0.1% TFA over 20 min at a flow rate of 15 mL per min. Fractions were collected, analyzed by HPLC and pure fractions pooled and lyophilized to give 6.8 mg.

Amino acid analysis: Ala 1.01 (1), Arg 1.25 (1), Cys N.D. (2), Lys 0.91 (1), Phe 0.91 (1), Thr 0.67 (1), Trp 0.31 (2), Val 0.92 (1).

EXAMPLE XXXVIII

D-Arg-D-Lys-cyclo(D-Cys-Gly-Ala-D-Cys)-D-Trp-D-Thr-D-Trp-D-Val-NH$_2$ (Preferred Peptide (38))

The peptide was prepared on an ABI Model 431A Peptide Synthesizer using Version 1.12 of the standard BOC software. 4-methyl benzhydrylamine resin (455 mg, 0.5 mmol) was used in the synthesis. The final weight of the resin was 1.37 g.

The peptide was cleaved from the resin (1.37 g) using 14 mL of HF and 1.4 mL of anisole for 60 min at 0° C. The resin was washed with ether and the peptide extracted with 40% acetic acid to give 510 mg of crude peptide. Peptide was cyclized by dissolving dilute NH$_4$OH (pH approx. 8) at a concentration of 4 mg/mL with Cu wire as a catalyst. After 20 hr of stirring the mixture was acidified with acetic acid and lyophilized.

The crude peptide was purified on a Vydac C-18 column (15μ, 5×25 cm) eluting with a 27–42% gradient of 80% acetonitrile in 0.1% TFA over 120 min at a flow rate of 15 mL per min. Fractions were collected, analyzed by HPLC and pure fractions pooled and lyophilized to give 77 mg of pure peptide which gave a negative Ellman test.

Amino acid analysis: Ala 0.99 (1), Arg 0.95 (1), Cys 1.68 (2), Gly 1.01 (1), Lys 0.93 (1), Thr 0.68 (1), Trp 1.28 (2), Val 0.94 (1).

EXAMPLE XXXIX

D-Arg-D-Lys-cyclo(D-Cys-Arg-Phe-D-Cys)-D-Trp-D-Thr-D-Trp-D-Val-NH$_2$ (Preferred Peptide (39))

The peptide was prepared on an ABI Model 431A Peptide Synthesizer using Version 1.12 of the standard BOC software. 4-methyl benzhydrylamine resin (455 mg, 0.5 mmol) was used in the synthesis. The final weight of the resin was 1.44 g.

The peptide was cleaved from the resin (1.44 g) using 14 mL of HF and 1.4 mL of anisole for 60 min at 0° C. The resin was washed with ether and the peptide extracted with 10% acetic acid to give 628 mg of crude peptide. 370 mg of crude peptide was cyclized in 50 mL of DMSO and 800 mL of distilled water by stirring for 4 days at a pH of 6 and room temperature. The resultant solution was lyophilized.

The crude peptide was purified on a Vydac C-18 column (15μ, 5×25 cm) eluting with a 34-60% gradient of 80% ethanol in 0.1% TFA over 120 min at a flow rate of 15 mL per min. Fractions were collected, analyzed by HPLC and pure fractions pooled and lyophilized to give 45 mg of pure peptide.

Amino acid analysis: Arg 1.99 (2), Cys 0.48 (2), Lys 1.00 (1), Phe 1.01 (1), Thr 0.80 (1), Trp 2.22 (2), Val 1.01 (1). FAB/MS: MH$^+$ 1383.2

EXAMPLE XL

D-Arg-D-Lys-cyclo(D-Cys-Gly-Arg-D-Cys)-D-Trp-D-Thr-D-Trp-D-Val-NH$_2$ (Preferred Peptide (40))

The peptide was prepared on an ABI Model 431A Peptide Synthesizer using Version 1.12 of the standard BOC software. 4-methyl benzhydrylamine resin (0.47 g, 0.5 mmol) were used in the synthesis. The final weight of the resin was 1.53 g.

The peptide was cleaved from the resin (1.5 g) using 15 mL of HF and 1.5 mL of anisole for 60 min at 0° C. The resin was washed with ether and the peptide extracted with TFA/DCM (1:1, v/v) (3×15 mL) to give 880 mg of crude peptide. The crude peptide (500 mg, 0.35 mmol) was dissolved in 25 mL of 30% AcOH and stirred with Mercury (II) Acetate (446 mg, 1.4 mmol) over 60 min at room temperature. Dithitohreitol (DTT) (1.076 g, 6.98 mmol) was added followed by stirring over 2 hrs and filtration of the reaction mixture through a pad of celite then through a 0.2μ filter. The peptide solution was divided, loaded onto a Vydac C-18 column, 15μ5×25 cm and purified in two runs using 20-40% gradient of 80% acetonitrile/0.1% TFA over 120 min with a flow rate of 15 mL/min. The semipure fractions were pooled and lyophilized yielding 240 mg of the crude linear peptide.

The crude linear peptide (240 mg) was dissolved in 50 mL of 25% AcOH and then added dropwise to the mixture of water (1000 mL), NH$_4$CH (to keep pH approx. 7.5) and 0.01M K$_3$Fe(CN)$_6$ (approx. 3 mL). After each addition of the linear precursor to the reaction mixture (approx. 1.5 mL) its pH was adjusted to 7.5 by addition of NH$_4$OH followed by addition of K$_3$Fe(CN)$_6$ solution. The total volume of the 0.01M K$_3$Fe(CN)$_6$ solution used for oxidation was 20 mL. The 2 mL of K$_3$Fe(CN)$_6$ solution was added extra and the mixture was stirred over 20 min (pH=7.5), then the pH was adjusted to 4-5 by addition of AcOH followed by stirring with 5 g of anion exchange AG 3-X4, 200-400 mesh, free base form (Bio-Rad) over 30 min. The resin was filtered off, washed with 5% acetic acid (3×100 mL) and combined fractions (approx. 1300 mL) were loaded onto a Vydac C-18 column 15μ, 10×30 cm) eluting with a 30-55% gradient of 80% ethanol in 0.1% TFA over 120 min at a flow rate of 60 mL per min. Fractions were collected, analyzed by HPLC and pure fractions pooled and lyophilized to give 37 mg of white solid.

Amino acid analysis: Arg 2.01 (2), Cys 0.47 (2), Gly 0.97 (1), Lys 1.01 (1), Thr 0.81 (1), Trp 2.44 (2), Val 1.01 (1). MH$^+$ 1292.7

EXAMPLE XLI

D-Arg-D-Lys-cyclo(D-Cys-Gly-Asn-D-Cys)-D-Trp-D-Thr-D-Trp-D-Val-NH$_2$ (Preferred Peptide (41))

The peptide was prepared on an ABI Model 431A Peptide Synthesizer using Version 1.12 of the standard BOC software. 4-methyl benzhydrylamine resin (455 mg, 0.5 mmol) was used in the synthesis. The final weight of the resin was 1.44 g.

The peptide was cleaved from the resin (1.44 g) using 14 mL of HF and 1.4 mL of anisole for 60 min at 0° C. The resin was washed with ether and the peptide extracted with 30% acetic acid to give 532 mg of crude peptide. Peptide was cyclized by dissolving dilute NH$_2$OH (pH approx. 8) at a concentration of 4 mg/mL with Cu wire as a catalyst. After 20 hr of stirring the mixture was acidified with acetic acid and lyophilized.

The crude peptide was purified on a Vydac C-18 column (15μ, 5×25 cm) eluting with a 27-45% gradient of 80% acetonitrile in 0.1% TFA over 120 min at a flow rate of 15 mL per min. Fractions were collected, analyzed by HPLC and pure fractions pooled and lyophilized to give 32 mg of pure peptide.

Amino acid analysis: Arg 0.96 (1), Asp 1.98 (2), Cys 1.64 (2), Gly 1.01 (1), Lys 0.97 (1), Thr 0.76 (1), Trp 0.89 (2) Val 0.99 (1).

EXAMPLE XLII

D-Arg-D-Lys-cyclo(D-Cys-Gly-Asp-D-Cys)-D-Trp-D-Thr-D-Trp-D-Val-NH$_2$ (Preferred Peptide (42))

The peptide was prepared on an ABI Model 431A Peptide Synthesizer using Version 1.12 of the standard BOC software. 4-methyl benzhydrylamine resin (455 mg, 0.5 mmol) was used in the synthesis. The final weight of the resin was 904 mg.

The peptide was cleaved from the resin (904 mg) using 10 mL of HF and 1 mL of anisole for 60 min at 0° C. The resin was washed with ether and the peptide extracted with 20% acetic acid to give 535 mg of crude peptide. Peptide was cyclized by dissolving dilute NH$_4$OH (pH approx. 8) at a concentration of 4 mg/mL with Cu wire as a catalyst. After 20 hr of stirring the mixture was acidified with acetic acid and lyophilized.

The crude peptide was purified on a Vydac C-18 column (15μ, 5×25 cm) eluting with a 27-45% gradient of 80% acetonitrile in 0.1% TFA over 120 min at a flow rate of 15 mL per min. Fractions were collected, analyzed by HPLC and pure fractions pooled and lyophilized to give 52 mg of pure peptide that gave a negative Ellman test.

Amino acid analysis: Arg 0.96 (1), Asx 1.06 (1), Cys 0.64 (2), Gly 1.01 (1), Lys 0.96 (1), Thr 0.83 (1), Trp 1.65 (2) Val 0.99 (1).

EXAMPLE XLIII

D-Arg-D-Lys-cyclo(D-Cys-Beta-Ala-Phe-D-Cys)-D-Trp-D-Thr-D-Trp-D-Val-NH$_2$ (Preferred Peptide (43))

The peptide was prepared on an ABI Model 431A Peptide Synthesizer using Version 1.12 of the standard BOC software. 4-methyl benzhydrylamine resin (0.625 g, 0.5 mmol) was used in the synthesis. All D-Boc amino acids and Boc-beta-Ala were purchased from Bachem Bioscience, Inc. The final weight of the resin was 1.62 g.

The peptide was cleaved from the resin (1.62 g) using 16 mL of HF and 1.6 mL of anisole for 60 min at 0° C. The resin was washed with ether and the peptide extracted with 50%

TFA in DCM to give 547 mg of crude peptide. The peptide was cyclized with air in the presence of Cu wire (5 cm) with 500 mL of ammonium acetate, pH 8.5 for 22 hours. The solution was lyophilized to give 519 mg.

The crude peptide (519 mg) was purified on a Vydac C-18 column (15μ, 5×25 cm) eluting with a 25–65% gradient of 80% acetonitrile in 0.1% TFA over 120 min at a flow rate of 15 mL per min. Fractions were collected, analyzed by HPLC and pure fractions pooled and lyophilized to give 44 mg.

Amino acid analysis: Arg 0.97 (1), Cys N.D. (2), Lys 1.01 (1), Phe 0.99 (1), Thr 0.79 (1), Trp 0.33 (2), Val 1.02 (1).

EXAMPLE XLIV

D-Arg-D-Lys-Cyclo(D-Cys-D-Ala-Phe-D-Cys)-D-Trp-D-Thr-D-Trp-D-Val-NH$_2$ (Preferred Peptide (44))

The peptide was prepared on an ABI Model 431A Peptide Synthesizer using Version 1.12 of the standard BOC software. 4-methyl benzhydrylamine resin (625 mg, 0.5 mmol) was used in the synthesis. All Boc-D-amino acids were obtained from Bachem Bioscience, Inc and 2 mmol of each was used in this synthesis. The final weight of the resin was 1.57 g.

The peptide was cleaved from the resin (1.57 g) using 16 mL of HF and 1.6 mL of anisole for 60 min at 0° C. The resin was washed with ether and the peptide extracted with 50% TFA in DCM to give 601 mg of crude peptide. The crude peptide was cyclized using air and 2 cm of copper wire in dilute acetic acid (4 mg/mL) which was adjusted to pH 8.5 with concentrated ammonium hydroxide.

The crude peptide (436 mg) was purified on a Vydac C-18 column (15μ, 5×25 cm) eluting with a 25–65% gradient of 80% acetonitrile in 0.1% TFA over 120 min at a flow rate of 15 mL per min. Fractions were collected, analyzed by HPLC and pure fractions pooled and lyophilized to give 14.2 mg.

Amino acid analysis: Ala 0.99 (1), Arg 1.01 (1), Lys 1.01 (1), Phe 0.97 (1), Thr 0.90 (1), Trp 1.54 (2), Val 1.03 (1).

EXAMPLE XLV

D-Arg-D-Lys-cyclo(D-Cys-D-Arg-Phe-D-Cys)-D-Trp-D-Thr-D-Trp-D-Val-NH$_2$ (Preferred Peptide (45))

The peptide was prepared on an ABI Model 431A Peptide Synthesizer using Version 1.12 of the standard BOC software. 4-methyl benzhydrylamine resin (455 mg, 0.5 mmol) was used in the synthesis. The final weight of the resin was 1.4 g.

The peptide was cleaved from the resin (1.4 g) using 14 mL of HF and 1.4 mL of anisole for 60 min at 0° C. The resin was washed with ether and the peptide extracted with 10% acetic acid to give 643 mg of crude peptide. 420 mg of crude peptide was cyclized in 50 mL of DMSO and 800 mL of distilled water stirring for 2 days at pH 6, at room temperature; then lyophilized.

The crude peptide was purified on a Vydac C-18 column (15μ, 5×25 cm) eluting with a 33–65% gradient of 80% ethanol in 0.1% TFA over 120 min at a flow rate of 15 mL per min. Fractions were collected, analyzed by HPLC and pure fractions pooled and lyophilized to give 65 mg of pure peptide.

Amino acid analysis: Arg 2.01 (2), Cys 0.50 (2), Lys 1.01 (1), Phe 0.99 (1), Thr 0.91 (1), Trp 2.27 (2), Val 0.99 (1). FAB/MS: MH$^+$ 1383.1

EXAMPLE XLVI

D-Arg-D-Lys-cyclo(D-Cys-Gly-Phe-D-Cys)-D-Gln-D-Thr-D-Trp-D-Val-NH$_2$ (Preferred Peptide (46))

The peptide was prepared on an ABI Model 431A Peptide Synthesizer using Version 1.12 of the standard BOC software. 4-methyl benzhydrylamine resin (0.625 g, 0.5 mmol) was used in the synthesis. The final weight of the resin was 1.55 g.

The peptide was cleaved from the resin (1.5 g) using 15 mL of HF and 1.5 mL of anisole for 60 min at 0° C. The resin was washed with ether and the peptide extracted with TFA/DCM (1:1, v/v) (3×15 mL) to give 690 mg of crude linear peptide.

The crude linear peptide (600 mg) was dissolved in 80 mL of 80% AcOH and then added dropwise to the mixture of water (1200 mL), NH$_4$OH (to keep pH approx. 7.5) and 0.01M K$_3$Fe(CN)$_6$ (approx. 3 mL). After each addition of the linear precursor to the reaction mixture (approx. 1.5 mL) its pH was adjusted to 7.5 by addition of NH$_4$OH followed by addition of K$_3$Fe(CN)$_6$ solution. The total volume of the 0.01M K$_3$Fe(CN)$_6$ solution used for oxidation was 36 mL. The 2 mL of K$_3$Fe(CN)$_6$ solution was added extra and the mixture was stirred over 20 min (pH=7.5), then the pH was adjusted to 4–5 by addition of AcOH followed by stirring with 5 g of anion exchange AG 3-X4, 200–400 mesh, free base form (Bio-Rad) over 30 min. The resin was filtered off, washed with 5% acetic acid (3×100 mL) and combined fractions (approx. 1700 mL) were loaded onto a Vydac C-18 column (15μ, 10×30 cm) eluting with a 0–10% over 5 min and 10–55% gradient of 80% acetonitrile in 0.1% TFA over 55 min at a flow rate of 120 mL per min. Fractions were collected, analyzed by HPLC and pure fractions pooled and lyophilized to give 115 mg of white solid.

Amino acid analysis: Arg 0.98 (1), Cys 0.77 (2), Glx 1.53 (1), Gly 0.99 (1), Lys 1.00 (1), Phe 0.96 (1), Thr 0.67 (1), Trp 1.05 (1), Val 1.02 (1).

EXAMPLE XLVII

D-Arg-D-Lys-cyclo(D-Cys-D-His-Phe-D-Cys)-D-Trp-D-Thr-D-Trp-D-Val-NH$_2$ (Preferred Peptide (47))

The peptide was prepared on an ABI Model 431A Peptide Synthesizer using Version 1.12 of the standard BOC software. 4-methyl benzhydrylamine resin (920 mg, 1 mmol) was used in the synthesis. All D-Boc-amino acids were purchased from Bachem Bioscience, Inc. The final weight of the resin was 2.42 g. Noted resin was trapped at top of reaction vessel during last cycle.

The peptide was cleaved from the resin (2.4 g) using 24 mL of HF and 2.4 mL of anisole for 60 min at 0° C. The resin was washed with ether and the peptide extracted with 50% TFA in DCM to give 714 mg of crude peptide. The linear peptide (714 mg) was cyclized in 750 mL of 10% DMSO at pH 6.5 for 24 hrs.

The crude peptide (714 mg) was purified on a Vydac C-18 column (15μ, 5×25 cm) eluting with a 20–60% gradient of 80% ethanol in 0.1% TFA over 120 min at a flow rate of 15 mL per min. Fractions were collected, analyzed by HPLC and pure fractions pooled and lyophilized to give 25 mg.

Amino acid analysis: Arg 0.96 (1), Cys 2.24 (2), His 0.91 (1), Lys 1.03 (1), Phe 1.03 (1), Thr 0.82 (1), Trp 2.46 (2), Val 1.08 (1).

EXAMPLE XLVIII

D-Arg-D-Lys-cyclo(D-Cys-Gly-Phe-D-Cys)-D-His-D-Thr-D-Trp-D-Val-NH$_2$ (Preferred Peptide (48))

The peptide was prepared on an ABI Model 431A Peptide Synthesizer using Version 1.12 of the standard BOC software. 4-methyl benzhydrylamine resin (0.625 g, 0.5 mmol) was used in the synthesis. The final weight of the resin was 1.6 g.

The peptide was cleaved from the-resin (1.6 g) using 16 mL of HF and 1.6 mL of anisole for 60 min at 0° C. The resin was washed with ether and the peptide extracted with TFA/DCM (1:1, v/v) (3×15 mL) to give 570 mg of crude peptide.

The crude linear peptide (320 mg) was dissolved in 70 mL of 50% AcOH and then added dropwise to the mixture of water (1200 mL), NH$_4$OH (to keep pH approx. 7.5) and 0.01M K$_3$Fe(CN)$_6$ (approx. 3 mL). After each addition of the linear precursor to the reaction mixture (approx. 1.5 mL) its pH was adjusted to 7.5 by addition of NH$_4$OH followed by addition of K$_3$Fe(CN)$_6$ solution. The total volume of the 0.01M K$_3$Fe(CN)$_6$ solution used for oxidation was 25 mL. The 2 mL of K$_3$Fe(CN)$_6$ solution was added extra and the mixture was stirred over 20 min (pH=7.5), then the pH was adjusted to 4-5 by addition of AcOH followed by stirring with 5 g of anion exchange AG 3-X4, 200–400 mesh, free base form (Bio-Rad) over 30 min. The resin was filtered off, washed with 5% acetic acid (3×100 mL) and combined fractions (approx. 1600 mL) were loaded onto a Vydac C-18 column (15µ, 10×30 cm) eluting with a 0–10% over 10 min and 10–50% gradient of 80% acetonitrile in 0.1% TFA over 50 min at a flow rate of 120 mL per min. Fractions were collected, analyzed by HPLC and pure fractions pooled and lyophilized to give 45 mg of white solid.

Amino acid analysis: Arg 0.98 (1), Cys 0.46 (2), Gly 1.07 (1), His 0.89 (1), Lys 1.02 (1), Phe 1.02 (1), Thr 0.71 (1), Trp 0.15 (1), Val 1.02 (1).

EXAMPLE XLIX

D-Arg-D-Lys-cyclo(D-Cys-Ile-Ile-D-Cys)-D-Trp-D-Thr-D-Trp-D-Val-NH$_2$ (Preferred Peptide (49))

The peptide was prepared on an ABI Model 431A Peptide Synthesizer using Version 1.12 of the standard BOC software. 4-methyl benzhydrylamine resin (0.46 g, 0.5 mmol) was used in the synthesis. The final weight of the resin was 1.27 g.

The peptide was cleaved from the resin (1.22 g) using 15 mL of HF and 1.5 mL anisole for 60 min at 0° C. The resin was washed with ether and ether/methylene chloride 1:1 and the peptide extracted with 50% TFA in methylene chloride to give 0.64 g of crude peptide after ether precipitation. The crude linear peptide (0.62 g) was dissolved in 270 mL water, adjusted to pH 7 and pumped into 1000 mL of 10% DMSO over 48 hrs. The solution was stirred for an additional 48 hrs.

The crude peptide solution was loaded onto a Vydac C-18 column (15µ, 10×30 cm) eluting with a 20–80% gradient of 80% ethanol in 0.1% TFA over 120 min at a flow rate of 60 mL per min. Fractions were collected, analyzed by HPLC and pure fractions pooled and lyophilized to give 0.127 g. The material was Elman negative.

Amino acid analysis: Arg 1.03 (1), Cys 2.29 (2), Ile 1.36 (2), Lys 1.03 (1), Thr 0.74 (1), Trp 2.29 (2), Val 1.01 (1).

EXAMPLE L

D-Arg-D-Lys-cyclo-desthio(D-Cys-Gly-Phe-D-Cys)(D-Acetyl Lys)-D-Thr-D-Trp-D-Val-NH$_2$ (Preferred Peptide (50))

The peptide was prepared on an ABI Model 431A Peptide Synthesizer using Version 1.12 of the standard BOC software. 4-methyl benzhydrylamine resin (0.69 g, 0.75 mmol) was used in the synthesis. All D-Boc-amino acids including D-Boc (ε-Fmoc) Lys were purchased from Bachem Bioscience, Inc. The final weight of the resin was 2 g.

The peptide was cleaved from the resin (2 g) using 20 mL of HF and 2 mL of anisole for 60 min at 0° C. The resin was washed with ether and the peptide extracted with 50% TFA in DCM-to give 723 mg of crude linear peptide. The linear peptide (723 mg) was cyclized in 800 mL of 10% DMSO at pH 7 for 2 days.

The crude peptide (723 mg) was partially purified on a Vydac C-18 column (15µ, 5×25 cm) eluting with a 20–60% gradient of 80% ethanol in 0.1% TFA over 120 min at a flow rate of 15 mL per min, then it was finally purified on a Vydac C-18 column (10µ, 2.5×25 cm) in 0.1% TFA using a 10–50% gradient of 80% acetonitrile in 0.1% TFA over 60 min at 10 mL/min. Fractions were collected, analyzed by HPLC and pure fractions pooled and lyophilized to give 17 mg.

Amino acid analysis: Arg 1.04 (1), Cys N.D. (2), Gly 0.96 (1), Lys 1.95 (2), Phe 1.03 (1), Thr 0.72 (1), Trp 1.36 (1), Val 1.02 (1).

FAB/MS: MH$^+$ 1267.57 (Relative Intensity=1) and MH$^+$-Sulfur 1235.36 (Relative Intensity=7)

EXAMPLE LI

D-Arg-D-Lys-cyclo(D-Cys-Gly-Phe-D-Cys)-D-Nal-D-Thr-D-Trp-D-Val-NH$_2$ (Preferred Peptide (51))

The peptide was prepared on an ABI Model 431A Peptide Synthesizer using Version 1.12 of the standard BOC software. 4-methyl benzhydrylamine resin (0.46 g, 0.5 mmol) was used in the synthesis. Boc-D-Nal-OH (MW 316.4, 0.632 g, 2 mmol), Boc-D-Cys(MOB)-OH (MW 341.43, 0.682 g, 2 mmol), BOC-D-Arg (Tos)-OH (MW 428.5, 0.856 g, 2 mmol), Boc-D-Thr-(Bzl)-OH (MW 309.37, 0.618 g, 2 mmol), Boc-D-Lys (2-Cl-Z)-OH (MW 414.89, 0.828 g 2 mmol), Boc-D-Trp-OH (MW 304.37, 0.608 g, 2 mmol) and Boc-D-Val-OH (MW 217.27, 0.434 g, 2 mmol) were supplied by Bachem Bioscience. The final weight of the resin was 1.335 g.

The peptide was cleaved from the resin (1.335 g) using 13 mL of HF and 1.3 mL of anisole for 60 min at 0° C. The resin was washed with ether and the peptide extracted with a 1:1 solution of TFA:DCM to give 633 mg of crude peptide.

The crude peptide (633 mg) was purified on a Vydac C-18 column (15µ, 5×25 cm) eluting with a 35–85% gradient of 80% ethanol in 0.1% TFA over 120 min at a flow rate of 15 mL per min. Fractions were collected, analyzed by HPLC and pure fractions pooled and lyophilized to give 223 mg linear peptide.

223 mg of linear peptide was dissolved in 1 liter of 8% DMSO (aqueous) pH 5.5 and left to cyclize for 48 hrs. The reaction was monitored by HPLC and the solution lyophilized.

The cyclized peptide was purified on a Vydac C-18 column (15µ, 5×25 cm) eluting with a 35–85% gradient of 80% ethanol in 0.1% TFA over 120 min at a flow rate of 15 mL per min. Fractions were collected, analyzed by HPLC and pure fractions pooled and lyophilized to give 57 mg of a peptide mixture.

The 57 mg of peptide mixture was purified using a Vydac C-18 column (10μ, 2.2×22 cm) eluting with a 30–55% gradient of 80% acetonitrile in 0.1% TFA over 60 min at a flow rate of 10 mL per min. Fractions were collected, analyzed by HPLC and pure fractions pooled to give 27 mg.

Amino acid analysis: Arg 1.01 (1), Cys 0.49 (2), Gly 0.99 (1), Lys 0.99 (1), Phe 1.0 (1), Thr 0.77 (1), Trp 1.34 (1), Val 1.01 (1).

FAB/MS: $MH^+$ 1295.0 disulfide 1263.1 thioether

EXAMPLE LII

D-Arg-D-Lys-cyclo(D-Cys-Gly-D-Ile-D-Cys)-D-Trp-D-Thr-D-Trp-D-Val-$NH_2$ (Preferred Peptide (52))

The peptide was prepared on an ABI Model 431A Peptide Synthesizer using Version 1.12 of the standard BOC software. 4-methyl benzhydrylamine resin (455 mg, 0.5 mmol) was used in the synthesis. The final weight of the resin was 1.31 g.

The peptide was cleaved from the resin (1.31 g) using 13 mL of HF and 1.3 mL of anisole for 60 min at 0° C. The resin was washed with ether and the peptide extracted with 30% acetic acid to give 564 mg of crude peptide. 320 mg of crude was cyclized in 50 mL of DMSO and/700 mL of distilled water by stirring for 3 days at pH 6 at room temperature; then lyophilized.

The crude peptide was purified on a Vydac C-18 column (15μ, 5×25 cm) eluting with a 35–68% gradient of 80% ethanol in 0.1% TFA over 120 min at a flow rate of 15 mL per min. Fractions were collected, analyzed by HPLC and pure fractions pooled and lyophilized to give 53 mg of pure peptide.

Amino acid analysis: Arg 1.05 (1), Cys 0.17 (2), Gly 1.13 (1), Ile 0.76 (1), Lys 1.04 (1), Thr 0.96 (1), Trp 2.46 (2), Val 1.02 (1).

FAB/MS: $MH^+$ 1250.3

EXAMPLE LIII

D-Arg-D-Lys-cyclo(D-Cys-Gly-D-Leu-D-Cys)-D-Trp-D-Thr-D-Trp-D-Val-$NH_2$ (Preferred Peptide (53))

The peptide was prepared on an ABI Model 431A Peptide Synthesizer using Version 1.12 of the standard BOC software. 4-methyl benzhydrylamine resin (455 mg, 0.5 mmol) was used in the synthesis. The final weight of the resin was 1.32 g.

The peptide was cleaved from the resin (1.32 g) using 13 mL of HF and 1.3 mL of anisole for 60 min at 0° C. The resin was washed with ether and the peptide extracted with 30% acetic acid to give 514 mg of crude peptide. 265 mg of crude peptide cyclized by dissolving it in 40 mL DMSO and 800 mL of water and stirring 2 days at pH 6 at room temperature followed by lyophilization.

The crude cyclized peptide was purified on a Vydac C-18 column (15μ, 5×25 cm) eluting with a 35–68% gradient of 80% ethanol in 0.1% TFA over 120 min at a flow rate of 15 mL per min. Fractions were collected, analyzed by HPLC and pure fractions pooled and lyophilized to give 46 mg of pure peptide.

Amino acid analysis: Arg 0.97 (1), Cys 0.39 (2), Gly 1.03 (1), Leu 1.07 (1), Lys 0.97 (1), Thr 0.92 (1), Trp 2.14 (2), Val 0.96 (1).

FAB/MS: $MH^+$ 1250.1

EXAMPLE LIV

D-Arg-D-Lys-cyclo(D-Cys-D-Lys-Phe-D-Cys)-D-Trp-D-Thr-D-Trp-D-Val-$NH_2$ (Preferred Peptide (54))

The peptide was prepared on an ABI Model 431A Peptide Synthesizer using Version 1.12 of the standard BOC software. 4-methyl benzhydrylamine resin (0.75 mmol, 0.69 g) was used in the synthesis. All D-Boc-amino acids were purchased from Bachem Bioscience, Inc. The final weight of the resin was 2.31 g.

The peptide was cleaved from the resin (2.3 g) using 23 mL of HF and 2.3 mL of anisole for 60 min at 0° C. The resin was washed with ether and the peptide extracted with 50% TFA in DCM to give 908 mg of crude linear peptide. The linear peptide was cyclized in 1000 mL of 10% DMSO at pH 7 over 72 hours.

The crude peptide (908 mg) was purified on a Vydac C-18 column (15μ, 5×25 cm) eluting with a 20–60% gradient of 80% ethanol in 0.1% TFA over 120 min at a flow rate of 15 mL per min. Fractions were collected, analyzed by HPLC and pure fractions pooled and lyophilized to give 98 mg.

Amino acid analysis: Arg 1.00 (1), Cys 2.33 (2), Lys 2.00 (2), Phe 0.99 (1), Thr 0.63 (1), Trp 2.40 (2), Val 1.00 (1).

EXAMPLE LV

D-Arg-D-Lys-cyclo(D-Cys-Gly-D-Lys-D-Cys)-D-Trp-D-Thr-D-Trp-D-Val-$NH_2$ (Preferred Peptide (55))

The peptide was prepared on an ABI Model 431A Peptide Synthesizer using Version 1.12 of the standard BOC software. 4-methyl benzhydrylamine resin (455 mg, 0.5 mmol) was used in the synthesis. The final weight of the resin was 1.3 g.

The peptide was cleaved from the resin (1.3 g) using 13 mL of HF and 1.3 mL of anisole for 60 min at 0° C. The resin was washed with ether and the peptide extracted with 20% acetic acid to give 564 mg of crude peptide. 255 mg of the crude peptide was cyclized in 50 mL of DMSO and 1100 mL of water for 5 days at pH6 followed by lyophilization.

The crude cyclized peptide was purified on a Vydac C-18 column (15μ, 5×25 cm) eluting with a 30–65% gradient of 80% ethanol in 0.1% TFA over 120 min at a flow rate of 15 mL per min. Fractions were collected, analyzed by HPLC and pure fractions pooled and lyophilized to give 27 mg of pure peptide.

Amino acid analysis: Arg 0.98 (1), Cys 1.91 (2), Gly 1.01 (1), Lys 2.02 (2), Thr 0.75 (1), Trp 2.48 (2), Val 0.99 (1).

FAB/MS: $MH^+$ 1264.7

EXAMPLE LVI

D-Arg-D-Lys-cyclo(D-Cys-Gly-Phe-D-Cys)-D-Lys-D-Thr-D-Trp-D-Val-$NH_2$ (Preferred Peptide (56))

The peptide was prepared on an ABI Model 431A Peptide Synthesizer using Version 1.12 of the standard BOC software. 4-methyl benzhydrylamine resin (0.625 g, 0.5 mmol) was used in the synthesis. The final weight of the resin was 1.6 g.

The peptide was cleaved from the resin (1.6 g) using 16 mL of HF and 1.6 mL of anisole for 60 min at 0° C. The resin was washed with ether and the peptide extracted with TFA/DCM (1:1, v/v) (3×15 mL) to give 520 mg of crude peptide.

The crude linear peptide (300 mg) was dissolved in 60 mL of 60% AcOH and then added dropwise to the mixture of water (1200 mL), NH$_4$OH (to keep pH approx. 7.5) and 0.01M K$_3$Fe(CN)$_6$ (approx. 3 mL). After each addition of the linear precursor to the reaction mixture (approx. 1.5 mL) its pH was adjusted to 7.5 by addition of NH$_4$OH followed by addition of K$_3$Fe(CN)$_6$ solution. The total volume of the 0.01M K$_3$Fe(CN)$_6$ solution used for oxidation was 32 mL. The 2 mL of K$_3$Fe(CN)$_6$ solution was added extra and the mixture was stirred over 20 min (pH=7.5), then the pH was adjusted to 4–5 by addition of AcOH followed by stirring with 5 g of anion exchange AG 3-X4, 200–400 mesh, free base form (Bio-Rad) over 30 min. The resin was filtered off, washed with 5% acetic acid (3×100 mL) and combined fractions (approx. 1600 mL) were loaded onto a Vydac C-18 column (15μ, 10×30 cm) eluting with a 0–10% over 10 min and 10–55% gradient of 80% acetonitrile in 0.1% TFA over 50 min at a flow rate of 120 mL per min. Fractions were collected, analyzed by HPLC and pure fractions pooled and lyophilized to give 102 mg of white solid.

Amino acid analysis: Arg 0.95 (1), Cys 0.20 (2), Gly 1.11 (1), Lys 1.97 (2), Phe 0.97 (1), Thr 0.88 (1), Trp 0.14 (1).

EXAMPLE LVII

D-Arg-D-Lys-cyclo(D-Cys-D-Pro-Phe-D-Cys)-D-Trp-D-Thr-D-Trp-D-Val-NH$_2$ (Preferred Peptide (57))

The peptide was prepared on an ABI Model 431A Peptide Synthesizer using Version 1.12 of the standard BOC software. 4-methyl benzhydrylamine resin (0.625 mg, 0.5 mmol) was used in the synthesis. The final weight of the resin was 1.97 g.

The peptide was cleaved from the resin (1.97 g) using 20 mL of HF and 2 mL of anisole for 60 min at 0° C. The resin was washed with ether and the peptide extracted with 50% TFA in DCM to give 224 mg of crude peptide. The peptide (224 mg) was cyclized at room temperature for 6 hrs by air in the presence of 3 cm of copper wire in 400 mL of dilute acetic acid which was adjusted to pH 8.5 with concentrated ammonium hydroxide.

The crude peptide (143 mg) was purified on a Vydac C-18 column (15μ, 5×25 cm) eluting with a 25–65% gradient of 80% acetonitrile in 0.1% TFA over 120 min at a flow rate of 15 mL per min. Fractions were collected, analyzed by HPLC and pure fractions pooled and lyophilized to give 19.5 mg.

Amino acid analysis: Arg 0.75 (1), Cys 1.82 (2), Lys 0.96 (1), Phe 0.98 (1), Pro 1.16 (1), Thr 0.71 (1), Trp 1.45 (2), Val 1.00 (1)

EXAMPLE LVIII

D-Arg-D-Lys-cyclo(D-Cys-Gly-D-Tpro-D-Cys)-D-Trp-D-Thr-D-Trp-D-Val-NH$_2$ (Preferred Peptide (58))

The peptide was prepared on an ABI Model 431A Peptide Synthesizer using Version 1.12 of the standard BOC software. 4-methyl benzhydrylamine resin (0.46 g, 0.5 mmol) was used in the synthesis. Boc-D-Thioproline (Boc-D-Tpro), Bachem, CA Lot #2J565 was added for the synthesis. The final weight of the resin was 1.07 g.

The peptide was cleaved from the resin (1.0 g) using 10 mL of HF and 1.0 mL of anisole for 60 min at 0° C. The resin was washed with ether and the peptide extracted with TFA/DCM (1:1, v/v) (3×15 mL) to give 340 mg of crude peptide. The crude linear peptide (340 mg) was dissolved in 80 mL of 70% AcOH and then added dropwise to the mixture of water (1200 mL), NH$_4$OH (to keep pH approx. 7.5) and 0.01M K$_3$Fe(CN)$_6$ (approx. 3 mL). After each addition of the linear precursor to the reaction mixture (approx. 1.5 mL) its pH was adjusted to 7.5 by addition of NH$_4$OH followed by addition of K$_3$Fe(CN)$_6$ solution. The total volume of the 0.01M K$_3$Fe(CN)$_6$ solution used for oxidation was 24 mL. The 2 mL of K$_3$Fe(CN)$_6$ solution was added extra and the mixture was stirred over 20 min (pH= 7.5), then the pH was adjusted to 4–5 by addition of AcOH followed by stirring with 5 g of anion exchange AG 3-X4, 200–400 mesh, free base form (Bio-Rad) over 30 min. The resin was filtered off, washed with 5% acetic acid (3×100 mL) and combined fractions (approx. 1700 mL), were loaded onto a Vydac C-18 column, 15μ, 10×30 cm eluting with 25–60% of 80% ethanol in 0.1% TFA over 60 min at a flow rate of 120 mL per min. Fractions were collected, analyzed by HPLC and pure fractions pooled and lyophilized to give 15 mg of yellow solid.

Amino acid analysis: Thr 0.74, (1), Gly 1.08 (1), Cys 2.34 (2), Val 1.05 (1), Lys 0.93 (1), Trp 2.47 (2), Arg 0.95 (1). FAB/MH$^+$ 1251.9

EXAMPLE LXIX

D-Arg-D-Lys-cyclo(D-Cys-Gly-D-Tic-D-Cys)-D-Trp-D-Thr-D-Trp-D-Val-NH$_2$ (Preferred Peptide (59))

The peptide was prepared on an ABI Model 431A Peptide Synthesizer using Version 1.12 of the standard BOC software. 4-methyl benzhydrylamine resin (0.46 g, 0.5 mmol) was used in the synthesis. N-Boc-D-1,2,3,4-tetrahydroisoquinoline-3-carboxylic acid (Boc-D-Tic) was purchased from Bachem Bioscience (Lot #502067) The final weight of the resin was 1.15 g.

The peptide was cleaved from the resin (1.1 g) using 11 mL of HF and 1.1 mL of anisole for 60 min at 0° C. The resin was washed with ether and the peptide extracted with TFA/DCM (1:1, v/v) (3×15 mL) to give 670 mg of crude peptide. The crude linear peptide (660 mg) was dissolved in 60 mL of 70% AcOH and then added dropwise to the mixture of water (1000 mL), NH$_4$OH (to keep pH approx. 7.5) and 0.01M K$_3$Fe(CN)$_6$ (approx. 3 mL). After each addition of the linear precursor to the reaction mixture (approx. 1.5 mL) its pH was adjusted to 7.5 by addition of NH$_4$OH followed by addition of K$_3$Fe(CN)$_6$ solution. The total volume of the 0.01M K$_3$Fe(CN)$_6$ solution was added extra and the mixture was stirred over 20 min (pH=7.5), then the pH was adjusted to 4–5 by addition of AcOH followed by stirring with 5 g of anion exchange AG 3-X4, 200–400 mesh, free base form (Bio-Rad) over 30 min. The resin was filtered off, washed with 5% acetic acid (3×100 mL) and combined fractions (approx. 1400 mL) were loaded onto a Vydac C-18 column (15μ, 10×30 cm) eluting with a 0–35% gradient over 5 min and a 35–65% gradient of 80% ethanol in 0.1% TFA over 55 min at a flow rate of 120 mL per min.

Fractions were collected, analyzed by HPLC and pure fractions pooled and evaporated to approximately 100 mL and lyophilized to give 27.5 mg of white solid.

Amino acid analysis: Arg 0.97 (1), Cys 2.90 (2), Gly 1.13 (1), Lys 0.96 (1), Thr 0.59 (1), Trp 2.03 (2), Val 0.95 (1).
FAB/MS: MH$^+$ 1296.1

EXAMPLE LX

D-Arg-D-Lys-cyclo(D-Cys-Gly-Trp-D-Cys)-D-Trp-D-Thr-D-Trp-D-Val-NH$_2$ (Preferred Peptide (60))

The peptide was prepared on an ABI Model 431A Peptide Synthesizer using Version 1.12 of the standard Boc software. 4-methyl benzyhydrylamine resin (0.57 g, 0.5 mmol) was used in the synthesis. The final weight of the resin was 1.41 g.

The peptide was cleaved from the resin (1.4 g) using 14 mL of HF and 1.4 mL of anisole for 60 min at 0° C. The resin was washed with either and the peptide extracted with TFA/DCM (1:1, v/v) (3×15 mL) to give 800 mg of crude peptide.

The crude linear peptide (800 mg) was dissolved in 140 mL of 85% AcOH and then added dropwise to the mixture of water (1100 mL), NH$_4$OH (to keep pH approx. 7.5) and 0.01M K$_3$Fe(CN)$_6$ (approx. 3 mL). After each addition of the linear precursor to the reaction mixture (approx. 1.5 mL) its pH was adjusted to 7.5 by addition of NH$_4$OH followed by addition of K$_3$Fe(CN)$_6$ solution. The total volume of the 0.01M K$_3$Fe(CN)$_6$ solution used for oxidation was 68 mL. The 2 mL of K$_3$Fe(CN)$_6$ solution was added extra and the mixture was stirred over 20 min (pH=7.5), then the pH was adjusted to 4–5 by addition of AcOH followed by stirring with 5 g of anion exchange AG 3-X4, 200–400 mesh, free base form (Bio-Rad) over 30 min. The resin as filtered off, washed with 5% acetic acid (3×100 mL) and combined fractions (approx. 2000 mL) were loaded onto a Vydac C-18 column 15µ, 10×30 cm) eluting with a 0–40% over 5 min and 40–65% gradient of 80% ethanol in 0.1% TFA over 55 min at a flow rate of 120 mL per min. Fractions were collected, analyzed by HPLC and semipure fractions pooled and lyophilized to give 75 mg of white solid.

The semipure peptide (75 mg) was repurified on a Vydac C-18 column (15µ, 5×25 cm) eluting with a 20–65% gradient of 80% acetonitrile in 0.1% TFA over 120 min at a flow rate of 15 mL/min. Fractions were collected, analyzed by HPLC, pooled and lyophilized to give 43 mg of semipure product.

The semipure peptide was finely repurified in two runs on a Vydac C-18 column (10µ, 2.2×25 cm) eluting with a 25–55% gradient of 80% acetonitrile in 0.1% TFA over 60 min at a flow rate of 10 mL/min. Fractions were collected, analyzed by HPLC and FAB-MS and pure fractions pooled and lyophilized to give 13 mg of white solid.

Amino acid analysis: Arg 0.97 (1), Cys 5.57 (2), Gly 1.10 (1), Lys 0.96 (1), Thr 0.72 (1), Trp 3.21 (3), Val 0.97 (1).
FAB/MS: MH$^+$=1322.6

EXAMPLE LXI

D-Arg-D-Lys-cyclo(D-Cys-Gly-Phe-D-Cys)-D-Trp-D-Thr-D-His-D-Val-NH$_2$ (Preferred Peptide (61))

The peptide was prepared on an ABI Model 431A Peptide Synthesizer using Version 1.12 of the standard BOC software. 4-methyl benzhydrylamine resin (0.625 g, 0.5 mmol) was used in the synthesis. The final weight of the resin was 1.6 g.

The peptide was cleaved from the resin (1.6 g) using 16 mL of HF and 1.6 mL of anisole for 60 min at 0° C. The resin was washed with ether and the peptide extracted with TFA/DCM (1:1, v/v) (3×15) to give 700 mg of crude peptide.

The crude linear peptide (680 mg) was dissolved in 80 mL of 70% AcOH and then added dropwise to the mixture of water (1200 mL), NHCOH (to keep pH approx. 7.5) and 0.01M K$_3$Fe(CN)$_6$ (approx. 3 mL). After each addition of the linear precursor to the reaction mixture (approx. 1.5 mL) its pH was adjusted to 7.5 by addition of NH$_4$OH followed by addition of K$_3$Fe(CN)$_6$ solution. The total volume of the 0.01M K$_3$Fe(CN)$_6$ solution used for oxidation was 43 mL. The 2 mL of K$_3$Fe(CN)$_6$ solution was added extra and the mixture was stirred over 20 min (pH=7.5), then the pH was adjusted to 4–5 by addition of AcOH followed by stirring with 5 g of anion exchange AG 3-X4, 200–400 mesh, free base form (Bio-Rad) over 30 min. The resin was filtered off, washed with 5% acetic acid (3×100 mL) and combined fractions (approx. 1600 mL) were loaded onto a Vydac C-18 column (15µ, 10×30 cm) eluting with a 0–10% over 5 min and 10–55% gradient of 80% acetonitrile in 0.1% TFA over 55 min at a flow rate of 120 mL per min. Fractions were collected, analyzed by HPLC and pure fractions pooled and lyophilized to give 73 mg of white solid.

Amino acid analysis: Arg 0.99 (1), Cys 0.33 (2), Gly 1.03 (1), His 0.92 (1), Lys 1.03 (1), Phe 1.00 (1), Thr 0.74 (1), Trp 0.15 (1), Val 1.03 (1).

EXAMPLE LXII

D-Arg-D-Lys-cyclo(D-Cys-Gly-Phe-D-Cys)-D-Trp-D-Thr-D-Lys-D-Val-NH$_2$ (Preferred Peptide (62))

The peptide was prepared on an ABI Model 431A Peptide Synthesizer using Version 1.12 of the standard BOC software. 4-methyl benzhydrylamine resin (0.625 g, 0.5 mmol) was used in the synthesis. The final weight of the resin was 1.6 g.

The peptide was cleaved from the resin (1.6 g) using 16 mL of HF and 1.6 mL of anisole for 60 min at 0° C. The resin was washed with ether and the peptide extracted with TFA/DCM (1:1, v/v) (3×15 mL) to give 800 mg of crude peptide.

The crude linear peptide (300 mg) was dissolved in 80 mL of 90% AcOH and then added dropwise to the mixture of water (1200 mL), NH$_4$OH (to keep pH approx. 7.5) and 0.01M K$_3$Fe(CN)$_6$ (approx. 3 mL). After each addition of the linear precursor to the reaction mixture (approx. 1.5 mL) its pH was adjusted to 7.5 by addition of NH$_4$OH followed by addition of K$_3$Fe(CN)$_6$ solution. The total volume of the 0.01M K$_3$Fe(CN)$_6$ solution used for oxidation was 33 mL. The 2 mL of K$_3$Fe (CN)$_6$ solution was added extra and the mixture was stirred over 20 min (pH=7.5), then the pH was adjusted to 4–5 by addition of ACOH followed by stirring with 5 g of anion exchange AG 3-X4, 200–400 mesh, free base form (Bio-Rad) over 30 min. The resin was filtered off, washed with 5% acetic acid (3×100 mL) and combined fractions (approx. 1700 mL) were loaded onto a Vydac C-18 column (15µ, 10×30 cm) eluting with a 0–10% over 10 min and 10–50% gradient of 80% acetonitrile in 0.1 TFA over 50 min at a flow rate of 120 mL per min. Fractions were collected, analyzed by HPLC and pure fractions pooled and lyophilized to give 77 mg of white solid.

Amino acid analysis: Arg 0.96 (1), Cys 0.35 (2), Gly 1.11 (1), Lys 1.99 (2), Phe 0.97 (1), Thr 0.75 (1), Trp 0.15 (1), Val 0.98 (1).

EXAMPLE LXIII

D-Arg-D-Lys-cyclo(D-Cys-Gly-Phe-D-Cys)-D-Trp-D-Thr-D-Tyr-D-Val-NH$_2$ (Preferred Peptide (63))

The peptide was prepared on an ABI Model 431A Peptide Synthesizer using Version 1.12 of the standard BOC software. 4-methyl benzhydrylamine resin (0.625 g, 0.5 mmol) was used in the synthesis. The final weight of the resin was 1.6 g.

The peptide was cleaved from the resin (1.6 g) using 16 mL of HF and 1.6 mL of anisole for 60 min at 0° C. The resin was washed with ether and the peptide extracted with TFA/DCM (1:1, v/v) (3×15 mL) to give 810 mg of crude peptide. The crude linear peptide (320 mg) was dissolved in 100 mL of 80% AcOH and then added dropwise to the mixture of water (1200 mL), NH$_4$OH (to keep pH approx. 7.5) and 0.01M K$_3$Fe(CN)$_6$ (approx. 3 mL). After each addition of the linear precursor to the reaction mixture (approx. 1.5 mL) its pH was adjusted to 7.5 by addition of NH$_4$OH followed by addition of K$_3$Fe(CN)$_6$ solution. The total volume of the 0.01M K$_3$Fe(CN)$_6$ solution used for oxidation was 22 mL. The 2 mL of K$_3$Fe(CN)$_6$ solution was added extra and the mixture was stirred over 20 min (pH= 7.5), then the pH was adjusted to 4-5 by addition of AcOH followed by stirring with 5 g of anion exchange AG 3-X4, 200-400 was filtered off, washed with 5% acetic acid (3×100 mL) and combined fractions (approx. 1700 mL) were loaded onto a Vydac C-18 column (15μ, 10×30 cm) eluting with a 0-20% over 10 min and 20-55% gradient of 80% acetonitrile in 0.1% TFA over 50 min at a flow rate of 120 mL per min. Fractions were collected, analyzed by HPLC and pure fractions pooled and lyophilized to give 40 mg of white solid.

Amino acid analysis: Arg 1.00 (1), Cys 0.28 (2), Gly 0.96 (1), Lys 1.01 (1), Phe 0.98 (1), Thr 0.67 (1), Trp 0.73 (1), Tyr 1.02 (1), Val 1.03 (1).

EXAMPLE LXIV

D-Arg-D-Lys-cyclo(D-Cys-Gly-Phe-D-Cys)-D-Tyr-D-Thr-D-Trp-D-Val-NH$_2$ (Preferred Peptide (64))

The peptide was prepared on an ABI Model 431A Peptide Synthesizer using Version 1.12 of the standard BOC software. 4-methyl benzhydrylamine resin (0.625 g, 0.5 mmol) was used in the synthesis. The final weight of the resin was 1.6 g.

The peptide was cleaved from the resin (1.6 g) using 16 mL of HF and 1.6 mL of anisole for 60 min at 0° C. The resin was washed with ether and the peptide extracted with TFA/DCM (1:1, v/v) (3×15 mL) to give 730 mg of crude peptide. The crude linear peptide (300 mg) was dissolved in 100 mL of 70% AcOH and then added dropwise to the mixture of water (1200 mL), NH$_4$OH (to keep pH approx. 7.5) and 0.01M K$_3$Fe(CN)$_6$ (approx. 3 mL). After each addition of the linear precursor to the reaction mixture (approx. 1.5 mL) its pH was adjusted to 7.5 by addition of NH$_4$OH followed by addition of K$_3$Fe(CN)$_6$ solution. The total volume of the 0.01M K$_3$Fe(CN)$_6$ solution used for oxidation was 30 mL. The 2 mL of K$_3$Fe(CN)$_6$ solution was added extra and the mixture was stirred over 20 min (pH 7.5), then the pH was adjusted to 4-5 by addition of AcOH followed by stirring with 5 g of anion exchange AG 3-X4, 200-400 mesh, free base form (Bio-Rad) over 30 min. The resin was filtered off, washed with 5% acetic acid (3×100 mL) and combined fractions (approx. 1600 mL) were loaded onto a Vydac C-18 column (15μ, 10×30 cm) eluting with a 0-20% over 10 min and 20-55% gradient of 80% acetonitrile in 0.1% TFA over 50 min at a flow rate of 120 mL per min. Fractions were collected, analyzed by HPLC and pure fractions pooled and lyophilized to give 66 mg of white solid.

Amino acid analysis: Arg 0.99 (1), Cys 0.23 (2), Gly 0.97 (1), Lys 1.01 (1), Phe 0.99 (1), Thr 0.69 (1), Trp 0.65 (1), Tyr 1.01 (1), Val 1.03 (1).

EXAMPLE LXV

D-Arg-D-Lys-cyclo(D-Cys-Gly-Gln-D-Cys)-D-Trp-D-Thr-D-Trp-D-Val-NH$_2$ (Preferred Peptide (65))

The peptide was prepared on an ABI Model 431A Peptide Synthesizer using Version 1.12 of the standard BOC software. 4-methyl benzhydrylamine resin (455 mg, 0.5 mmol) was used in the synthesis. The final weight of the resin was 1.5 g.

The peptide was cleaved from the resin (1.5 g) using 15 mL of HF and 1.5 mL of anisole for 60 min at 0° C. The resin was washed with ether and the peptide extracted with 30% acetic acid to give 606 mg of crude peptide. Peptide was cyclized by dissolving dilute NH$_2$OH (pH approx. 8) in concentration 4 mg/mL with Cu wire as a catalyst. After 20 hr of stirring the mixture was acidified with acetic acid and lyophilized.

The crude peptide was purified on a Vydac C-18 column (15μ, 5×25 cm) eluting with a 27-45% gradient of 80% acetonitrile in 0.1% TFA over 120 min at a flow rate of 15 mL per min. Fractions were collected, analyzed by HPLC and pure fractions pooled and lyophilized to give 37 mg of pure peptide.

Amino acid analysis: Asp 0.93 (1), Cys 2.15 (2), Gln 1.55 (1), Gly 1.08 (1), Lys 0.92 (1), Thr 0.69 (1), Trp 1.35 (2), Val 0.92 (1).

EXAMPLE LXVI

D-Arg-D-Lys-D-cyclo(D-Cys-Gly-Glu-D-Cys)-D-Trp-D-Thr-D-Trp-D-Val-NH$_2$ (Preferred Peptide (66))

The peptide was prepared on an ABI Model 431A Peptide Synthesizer using Version 1.12 of the standard BOC software. 4-methyl benzhydrylamine resin (45 mg, 0.5 mmol) was used in the synthesis. The final weight of the resin was 1.47 g.

The peptide was cleaved from the resin (1.47 g) using 14 mL of HF and 1.4 mL of anisole for 60 min at 0° C. The resin was washed with ether and the peptide extracted with 20% acetic acid to give 592 mg of crude peptide. Peptide was cyclized by dissolving dilute NH$_4$OH (pH approx. 8) in a concentration of 4 mg/mL with Cu wire as a catalyst. After 20 hr of stirring the mixture was acidified with acetic acid and lyophilized.

The crude peptide was purified on a Vydac C-18 column (15μ, 5×25 cm) eluting with a 27–45% gradient of 80% acetonitrile in 0.1% TFA over 120 min at a flow rate of 15 mL per min. Fractions were collected, analyzed by HPLC and pure fractions pooled and lyophilized to give 44 mg of pure peptide which gave a negative Ellman test.

Amino acid analysis: Arg 1.02 (1), Cys 1.40 (2), Glx 1.39 (1), Gly 0.96 (1), Lys 1.02 (1), Thr 0.77 (1), Trp 1.40 (2), Val 1.04 (1).

EXAMPLE LXVII

D-Arg-D-Lys-cyclo(D-Cys-Ile-D-Ile-D-Cys)-D-Trp-D-Thr-D-Trp-D-Val-NH$_2$ (Preferred Peptide (67))

The peptide was prepared on an ABI Model 431A Peptide Synthesizer using Version 1.12 of the standard BOC software. 4-methyl benzhydrylamine resin (0.46 g, 0.5 mmol) was used in the synthesis. Boc-D-Cys(MOB)-OH (MW 341.43, 0.682 g, 2 mmol) was supplied by Bachem of California. BOC-D-Arg (Tos)-OH (MW 428.5, 0.856 g, 2 mmol), Boc-D-Thr-(Bzl)-OH (MW 309.37, 0.618 g, 2 mmol), Boc-D-Lys (2-Cl-Z)-OH (MW 414.89, 0.828 g 2 mmol), Boc-D-Trp-OH (MW 304.37, 0.608 g, 2 mmol) and Boc-D-Val-OH (MW 217.27, 0.434 g, 2 mmol) were supplied by Bachem Bioscience. The final weight of the resin was 1.785 g.

The peptide was cleaved from the resin (1.486 g) using 15 mL of HF and 1.5 mL of anisole for 60 min at 0° C. The resin was washed with ether and the peptide extracted with a 1:1 solution of TFA:DCM to give 804 mg of crude peptide. 250 mg of crude peptide was dissolved in 1800 mL of 8% DMSO (aqueous) pH 5.5 and left to stirred for 2 days. The reaction was monitored by HPLC and the solution was lyophilized when complete.

The crude peptide (250 mg) was purified on a Vydac C-18 column (15μ, 5×25 cm) eluting with a 35–85% gradient of 80% ethanol in 0.1% TFA over 120 min at a flow rate of 15 mL per min. Fractions were collected, analyzed by HPLC and pure fractions pooled and lyophilized to give 22 mg. Compound tested Ellman negative.

Amino acid analysis: Arg 0.99 (1), Cys 1.17 (2), Ile 1.41 (2), Lys 0.99 (1), Thr 0.80 (1), Trp 2.52 (2), Val 1.02 (1).

EXAMPLE LXVIII

D-Arg-D-Lys-cyclo(D-Cys-Gly-Ile-D-Cys)-D-Trp-D-Thr-D-Trp-D-Val-NH$_2$ (Preferred Peptide (68))

The peptide was prepared on an ABI Model 431A Peptide Synthesizer using Version 1.12 of the standard BOC software. 4-methyl benzhydrylamine resin (455 mg, 0.5 mmol) was used in the synthesis. The final weight of the resin was 1.44 g.

The peptide was cleaved from the resin (1.44 g) using 14 mL of HF and 1.4 mL of anisole for 60 min at 0° C. The resin was washed with ether and the peptide extracted with 40% acetic acid to give 566 mg of crude peptide. Peptide was cyclized by dissolving dilute NH$_4$OH (pH approx. 8) at a concentration of 4 mg/mL with Cu wire as a catalyst. After 20 hr of stirring the mixture was acidified with acetic acid and lyophilized.

The crude peptide was purified on a Vydac C-18 column (15μ, 5×25 cm) eluting with a 27–47% gradient of 80% acetonitrile in 0.1% TFA over 120 min at a flow rate of 15 mL per min. Fractions were collected, analyzed by HPLC and pure fractions pooled and lyophilized to give 16 mg of pure peptide which gave a negative Ellman test.

Amino acid analysis: Arg 0.98 (1), Cys 0.88 (2), Gly 1.01 (1), Ile 0.84 (1), Lys 0.98 (1), Thr 0.75 (1), Trp 1.55 (2), Val 0.99 (1).

EXAMPLE LXIX

D-Arg-D-Lys-cyclo(D-Cys-Gly-Leu-D-Cys)-D-Trp-D-Thr-D-Trp-D-Val-NH$_2$ (Preferred Peptide (69))

The peptide was prepared on an ABI Model 431A Peptide Synthesizer using Version 1.12 of the standard BOC software. 4-methyl benzhydrylamine resin (455 mg, 0.5 mmol) was used in the synthesis. The final weight of the resin was 1.26 g.

The peptide was cleaved from the resin (1.26 g) using 13 mL of HF and 1.3 mL of anisole for 60 min at 0° C. The resin was washed with ether and the peptide extracted with 30% acetic acid to give 542 mg of crude peptide. 265 mg of crude peptide cyclized by dissolving in 40 mL of DMSO adding it o 800 mL of distilled water and adjusting to pH 6. After 4 days of stirring at room temperature the mixture was lyophilized.

The crude cyclized peptide was purified on a Vydac C-18 column (15μ, 5×25 cm) eluting with a 35–68% gradient of 80% ethanol in 0.1% TFA over 120 min at a flow rate of 15 mL per min. Fractions were collected, analyzed by HPLC and pure fractions pooled and lyophilized to give 22 mg of pure peptide.

Amino acid analysis: Arg 0.99 (1), Cys 2.67 (2), Gly 1.01 (1), Leu 1.03 (1), Lys 0.99 (1), Thr 0.78 (1), Trp 2.56 (2), Val 0.99 (1). FAB/MS: MH$^+$ 1249.3

EXAMPLE LXX

D-Arg-D-Lys-cyclo(D-Cys-Lys-Phe-D-Cys)-D-Trp-D-Thr-D-Trp-D-Val-NH$_2$ (Preferred Peptide (70))

The peptide was prepared on an ABI Model 431A Peptide Synthesizer using Version 1.12 of the standard BOC software. 4-methyl benzhydrylamine resin (0.69 g, 0.75 mmol) was used in the synthesis. All D-Boc-amino acids were purchased from Bachem Bioscience, Inc. The final weight of the resin was 2.27 g.

The peptide was cleaved from the resin (2.27 g) using 23 mL of HF and 2.3 mL of anisole for 60 min at 0° C. The resin was washed with ether and the peptide extracted with 50% TFA in DCM to give 864 mg of crude linear peptide. The linear peptide (864 mg) was cyclized in 900 mL of 10% DMSO at pH 7.0 for 48 hrs.

The crude cyclized peptide (864 mg) was purified on a Vydac C-18 column (15μ, 5×25 cm) eluting with a 20–60% gradient of 80% ethanol in 0.1% TFA over 120 min at a flow rate of 15 mL per min. Fractions were collected, analyzed by HPLC and pure fractions pooled and lyophilized to give 76 mg.

Amino acid analysis: Arg 1.01 (1), Cys 2.21 (2), Lys 1.99 (2), Phe 1.00 (1), Thr 0.74 (1), Trp 2.62 (2), Val 1.00 (1).

EXAMPLE LXXI

D-Arg-D-Lys-cyclo(D-Cys-Gly-Lys-D-Cys)-D-Trp-D-Thr-D-Trp-D-Val-NH$_2$ (Preferred Peptide (71))

The peptide was prepared on an ABI Model 431A Peptide Synthesizer using Version 1.12 of the standard BOC software. 4-methyl benzhydrylamine resin (455 mg, 0.5 mmol) was used in the synthesis. The final weight of the resin was 1.29 g.

The peptide was cleaved from the resin (1.29 g) using 13 mL of HF and 1.3 mL of anisole for 60 min at 0° C. The resin was washed with ether and the peptide extracted with 20% acetic acid to give 492 mg of crude peptide. The crude peptide was cyclized by stirring two batches of 240 mg in 50 mL of DMSO and 1 L of water for 3 days at pH 6 followed by lyophilization.

The crude cyclized peptide was purified on a Vydac C-18 column (15µ, 5×25 cm) eluting with a 28–65% gradient of 80% ethanol in 0.1% TFA over 120 min at a flow rate of 15 mL per min. Fractions were collected, analyzed by HPLC and pure fractions pooled and lyophilized to give 50 mg of pure peptide.

Amino acid analysis: Arg 0.99 (1), Cys 2.42 (2), Gly 1.11 (1), Lys 1.92 (2), Thr 0.71 (1), Trp 2.52 (2), Val 0.98 (1) FAB/MS: MH$^+$ 1264.4

EXAMPLE LXXII

D-Arg-D-Lys-cyclo(D-Cys-Gly-[N-Methyl-Phe]-D-Cys)-D-Trp-D-Thr-D-Trp-D-Val-NH$_2$ (Preferred Peptide (72))

The peptide was prepared on an ABI Model 431A Peptide Synthesizer using Version 1.12 of the standard BOC software. 4-methyl benzhydrylamine resin (0.625 g, 0.5 mmol) was used in the synthesis. Boc-D-Cys(MOB)-OH (MW 341.43, 0.682 g, 2 mmol), BOC-D-Arg (mos)-OH (MW 428.5, 0.856 g, 2 mmol), Boc-D-Thr-(Bzl)-OH (MW 309.37, 0.618 g, 2 mmol), Boc-D-Lys (2-Cl-Z)-OH (MW 414.89, 0.828 g 2 mmol), Boc-D-Trp-OH (MW 304.37, 0.608 g, 2 mmol) and Boc-D-Val-OH (MW 217.27, 0.434 g, 2 mmol) were supplied by Bachem Bioscience. The final weight of the resin was 1.652 g.

The peptide was cleaved from the resin (1.652 g) using 17 mL of HF and 1.7 mL of anisole for 60 min at 0° C. The resin was washed with ether and the peptide extracted with a 1.1 solution of TFA:DCM to give 750 mg of crude peptide.

The crude linear peptide (502 mg) was dissolved in 100 mL of 40% AcOH and then added dropwise to the mixture of water (1800 mL), NH$_4$OH (to keep pH approx. 7.5) and 0.01M K$_3$Fe(CN)$_6$ (approx. 3 mL). After each addition of the linear precursor to the reaction mixture (approx. 1.5 mL) its pH was adjusted to 7.5 by the addition of NH$_4$OH, followed by the addition of K$_3$Fe(CN)$_6$ solution. The total volume of the 0.01M K$_3$Fe(CN)$_6$ solution used for oxidation was 50 mL. The mixture was stirred over 20 min (pH=7.5), then the pH was adjusted to 4–5 with the addition of AcOH, followed by stirring with 15 g of anion exchange AG 3-X4, 200–400 mesh, free base form (Bio-Rad) over 30 min. The resin was filtered off, the solution was lyophilized and the crude product directly lyophilized.

The crude peptide was purified on a Vydac C-18 column (15µ, 5×25 cm) eluting with a 35–55% gradient of 80%. acetonitrile in 0.1% TFA over 120 min at a flow rate of 15 mL per min. Fractions were collected, analyzed by HPLC and pure fractions pooled and lyophilized to give 31 mg.

Amino acid analysis: Arg 0.99 (1), Cys 0.33 (2), Gly 0.87 (1), Lys 0.98 (1), Thr 0.71 (1), Trp 1.66 (2), Val 1.02 (1).

EXAMPLE LXXIII

D-Arg-D-Lys-cyclo(D-Glys-Gly-Nal-D-Cys)-D-Trp-D-Thr-D-Trp-D-Val-NH$_2$ (Preferred Peptide (73))

The peptide was prepared on an ABI Model 431A Peptide Synthesizer using Version 1.12 of the standard Boc software. 4-methyl benzhydrylamine resin (0.46 g, 0.5 mmol) was used in the synthesis. Boc-3-(2-Naphthyl)-L-alanine (Boc-Nal) was purchased from Bachem Bioscience (Lot 124164) The final weight of the resin was 1.35 g.

The peptide was cleaved from the resin (1.3 g) using 13 mL of HF and 1.3 mL of anisole for 60 min at 0° C. The resin was washed with ether and the peptide extracted with TFA/DCM (1:1, v/v) (3×15 mL) to give 770 mg of crude peptide.

The crude linear peptide (150 mg) was dissolved in 100 mL of DMSO then diluted with water (900 mL) and stirred over 18 hrs at room temperature (pH was brought to 6.5 by addition of 28% NH$_4$OH). the solution (approx. 1000 mL) was loaded onto a Vydac C-18 column (15µ, 10×30 cm) eluting with a 30–75% gradient of 80% ethanol in 0.1% TFA over 120 min at a flow rate of 60 mL per min. Fractions were collected, analyzed by HPLC and pure fractions pooled and lyophilized to give 21 mg of white solid.

Amino acid analysis: Arg 0.98 (1), Cys 0.29 (2), Gly 1.04 (1), Lys 0.98 (1), Thr 1.06 (1), Trp 2.33 (2), Val 0.99 (1) FAB/MS: MH$^+$ 1333.7

EXAMPLE LXXIV

D-Arg-D-Lys-cyclo-(D-Cys-Phe-Gly-D-Cys)-D-Trp-D-Thr-D-Trp-D-Val-NH$_2$ (Preferred Peptide (74))

The peptide was prepared on an ABI Model 431A Peptide Synthesizer using Version 1.12 of the standard BOC software. 4-methyl benzhydrylamine resin (0.625 g, 0.5 mmol) was used in the synthesis. BOC-D-Cys(MOB)-OH (MW 341.43, 0.682 g, 2 mmol), BOC-D-Arg (TOS)-OH (MW 428.5, 0.856 g, 2 mmol), BOC-D-Thr-(Bzl)-OH (MW 309.37, 0.618 g, 2 mmol), BOC-D-Lys (2-Cl-Z)-OH (MW 414.89 , 0.828 g, 2 mmol), BOC-D-Trp-OH (MW 304.37, 0.608 g, 2 mmol) and BOC-D-Val-OH (MW 217.27, 0.434 g, 2 mmol) were supplied by Bachem Bioscience. The final weight of the resin was 1.675 g.

The peptide was cleaved from the resin (1.652 g) using 16 mL of HF and 1.6 mL of anisole for 60 min at 0° C. The resin was washed with ether and the peptide extracted with a 1:1 solution of TFA:DCM to give 876 mg of crude peptide. The peptide was cyclized by dissolving 547 mg of peptide into 80 mL of 50% acetic acid. A solution (1600 mL) of 10% DMSO (aqueous) was prepared to which the peptide solution was added. The pH was 5.5 and the solution stirred overnight. The reaction was monitored by HPLC and lyophilized.

The crude peptide was purified on a Vydac C-18 column (15µ, 5×25 cm) eluting with a 30–50% gradient of 80% acetonitrile in 0.1% TFA over 120 min min at a flow rate of 15 mL per min. Fractions were collected, analyzed by HPLC and pure fractions pooled and lyophilized to give 75 mg.

Amino acid analysis: Arg 0.99 (1), Cys 1.52 (2), Gly 1.01 (1), Lys 1.0 (1), Phe 0.99 (1), Thr 0.90 (1), Trp 0.26 (2), Val 1.0 (1) FAB/MS: MH$^+$ 1282.4

EXAMPLE LXXV

D-Arg-D-Lys-cyclo(D-Cys-Gly-Phe-D-Cys)-Val-D-Trp-D-Thr-D-Trp-NH$_2$ (Preferred Peptide (75))

The peptide was prepared on an ABI Model 431A Peptide Synthesizer using Version 1.12 of the standard BOC software. 4-methyl benzhydrylamine resin (0.45 g, 0.5 mmol) was used in the synthesis. The final weight of the resin was 1.399.

The peptide was cleaved from the resin (1.365) using 210 of HF and 1 mL anisole and 1 mL thioanisole and ether/methylene chloride 1:1 for 60 min at 0° C. The resin was washed with ether and ether/methylene chloride 1:1 and the peptide extracted with 50% TFA in methylene chloride to give 0.698 of crude peptide. The crude peptide (0.65 g) was dissolved in 50 mL of acetic acid and added incrementally to 1750 mL water along with increments of 0.1M $K_3Fe(CN)_6$, adjusted the pH to 7–7.5 with concentrated $NH_4OH$. Total volume of $K_3Fe(CN)_6$ solution was 45 mL. An addition 3 mL was added and the solution stirred 1.5 hr. Solids were removed by centrifugation and the solution adjusted to pH 5 with acetic acid and treated using 5 g of BioRad 3-X4 resin.

The crude peptide solution was loaded onto a Vydac C-18 column (15μ, 10×25 cm) eluting with a 20–80% gradient of 80% aqueous ethanol in 0.1% TFA over 120 min at a flow rate of 60 per min. Fractions were collected, analyzed by HPLC and pure fractions pooled and lyophilized to give 34 mg.

Amino acid analysis: Arg 1.04 (1), Gly 0.90 (1), Lys 1.03 (1), Phe 1.03 (1), Thr 0.78 (1), Trp 2.07 (2), Val 1.01 (1).

EXAMPLE LXXVI

D-Arg-D-Lys-cyclo(D-Cys-Gly-Phe-D-Cys)-D-Pro-D-Thr-D-Trp-D-Val-$NH_2$ (Preferred Peptide (76))

The peptide was prepared on an ABI Model 431A Peptide Synthesizer using Version 1.12 of the standard BOC software. 4-methyl benzhydrylamine resin (0.454 g, 0.5 mmol) was used in the synthesis. Boc-D-Cys(MOB)-OH (MW 341.43, 0.682 g, 2 mmol), was supplied by Bachem of California. Boc-D-Pro-OH (MW 215.25, 0.430 g, 2 mmol), BOC-D-Arg (Tos)-OH (MW 428.5, 0.856 g, 2 mmol), Boc-D-Thr-(Bzl)-OH (MW 309.37, 0.618 g, 2 mmol), Boc-D-Lys (2-Cl-Z)-OH (MW 414.89, 0.828 g 2 mmol), Boc-D-Trp-OH (MW 304.37, 0.608 g, 2 mmol) and Boc-D-Val-OH (MW 217.27, 0.434 g, 2 mmol) were supplied by Bachem Bioscience. The final weight of the resin was 1.498 g.

The peptide was cleaved from the resin (1.363 g) using 14 mL of HF and 1.4 mL of anisole for 60 min at 0° C. The resin was washed with ether and the peptide extracted with a 1:1 solution of TFA:DCM to give 529 mg of crude peptide. 301 mg of crude peptide were dissolved in 1800 mL of 8% DMSO (aqueous) pH 6.0 and left to cyclize for 8 days. The reaction was monitored by HPLC and lyophilized when complete.

The crude peptide (301 mg) was purified on a Vydac C-18 column (15μ, 5×25 cm) eluting with a 30–70% gradient of 80% ethanol in 0.1% TFA over 120 min at a flow rate of 15 mL per min. Fractions were collected, analyzed by HPLC and pure fractions pooled and lyophilized to give 62 mg. Compound tested Ellman negative.

Amino acid analysis: Arg 0.85 (1), Cys 6.73 (2), Gly 1.56 (1), Lys 0.83 (1), Phe 0.86 (1), Pro 1.25 (1), Thr 0.55 (1), Trp 1.23 (1), Val 0.91 (1).

EXAMPLE LXXVII

D-Arg-D-Lys-cyclo(D-Cys-Gly-Phe-D-Cys)-D-Trp-D-Thr-D-Pro-D-Val-$NH_2$ (Preferred Peptide (77))

The peptide was prepared on an ABI Model 431A Peptide Synthesizer using Version 1.12 of the standard BOC software. 4-methyl benzhydrylamine resin (0.46 g, 0.5 mmol) was used in the synthesis. Boc-D-Cys(MOB)-OH (MW 341.43, 0.682 g, 2 mmol), was supplied by Bachem of California. Boc-D-Pro-OH (MW 215.25, 0.430 g, 2 mmol, BOC-D-Arg (Tos)-OH (MW 428.5, 0.856 g, 2 mmol), Boc-D-Thr-(Bzl)-OH (MW 309.37, 0.618 g, 2 mmol), Boc-D-Lys (2-Cl-Z)-OH (MW 414.89, 0.828 g 2 mmol), Boc-D-Trp-OH (MW 304.37, 0.608 g, 2 mmol) and Boc-D-Val-OH (MW 217.27, 0.434 g, 2 mmol) were supplied by Bachem Bioscience. The final weight of the resin was 1.496 g.

The peptide was cleaved from the resin (1.369 g) using 14 mL of HF and 1.4 mL of anisole for 60 min at 0° C. The resin was washed with ether and the peptide extracted with a 1:1 solution of TFA:DCM to give 410 mg of crude peptide.

The crude peptide (410 mg) was purified on a Vydac C-18 column (15μ, 5×25 cm) eluting with a 30–70% gradient of 80% ethanol in 0.1% TFA over 120 min at a flow rate of 15 mL per min. Fractions were collected, analyzed by HPLC and pure fractions pooled and lyophilized to give 90 mg of linear product.

90 mg of linear peptide was dissolved in 500 mL of 8% DMSO (aqueous) pH 5.5 and left to stir for 5 days. The reaction was monitored by HPLC and lyophilized when complete.

The peptide was purified on a Vydac C-18 column (15), 5×25 cm) eluting with a 35–85% gradient of 80% ethanol in 0.1% TFA over 120 min at a flow rate of 15 mL per min. Fractions were collected, analyzed by HPLC and pure fractions pooled and lyophilized to give 23 mg.

Amino acid analysis: Arg 0.98 (1), Cys 0.41 (2), Gly 1.11 (1), Lys 0.96 (1), Phe 0.98 (1), Pro 1.01 (1), Thr 0.75 (1), Trp 1.34 (1), Val 0.98 (1).

EXAMPLE LXXVIII

D-Arg-D-Lys-cyclo-desthio(D-Cys-Gly-Phe-D-Cys)-D-Trp-D-Thr-D-Nal-D-Val-$NH_2$ (Preferred Peptide (78))

The peptide was prepared on an ABI Model 431A Peptide Synthesizer using Version 1.12 of the standard BOC software. 4-methyl benzhydrylamine resin (0.46 g, 0.5 mmol) was used in the synthesis. Boc-D-Nal-OH (MW 316.4, 0.632 g, 2 mmol), Boc-D-Cys(MOB)-OH (MW 341.43, 0.682 g, 2 mmol), BOC-D-Arg (Tos)-OH (MW 428.5, 0.856 g, 2 mmol), Boc-D-Thr-(Bzl)-OH (MW 309.37, 0.618 g, 2 mmol), Boc-D-Lys (2-Cl-Z)-OH (MW 414.89, 0.828 g 2 mmol), Boc-D-Trp-OH (MW 304.37, 0.608 g, 2 mmol) and Boc-D-Val-OH (MW 217.27, 0.434 g, 2 mmol) were supplied by Bachem Bioscience. The final weight of the resin was 1.562 g.

The peptide was cleaved from the resin (1.562 g) using 16 mL of HF and 1.6 mL of anisole for 60 min at 0° C. The resin was washed with ether and the peptide extracted with a 1:1 solution of TFA:DCM to give 780 mg of crude peptide.

The crude peptide (780 mg) was purified on a Vydac C-18 column (15μ, 5×25 cm) eluting with a 35–85% gradient of 80% ethanol in 0.1% TFA over 120 min at a flow rate of 15 mL per min. Fractions were collected, analyzed by HPLC and pure fractions pooled and lyophilized to give 165 mg of linear peptide.

165 mg of linear peptide was dissolved in 500 mL of 8% DMSO (aqueous) pH 6.5 and left for 48 hrs to cyclize. The reaction was monitored by HPLC and then lyophilized.

The cyclic peptide was purified on a Vydac C-18 column (15μ, 5×25 cm) eluting with a 35–65% gradient of 80% ethanol in 0.1% TFA over 120 min at a flow rate of 15 mL per min. Fractions were collected, analyzed by HPLC and pure fractions pooled and lyophilized to give 8 mg.

Amino acid analysis: Arg 1.01 (1), Cys 0.66 (2), Gly 0.79 (1), Lys 1.18 (1), Phe 0.99 (1), Thr 0.78 (1), Trp 1.55 (1), Val 1.02 (1). FAB/MS: MH$^+$ 1294.7 disulfide 1263.7 thioether

EXAMPLE LXXIX

D-Arg-D-Lys-cyclo(D-Cys-Gly-Phe-D-Cys)-D-Trp-D-Thr-D-Phe-D-Val-NH$_2$ (Preferred Peptide (79))

The peptide was prepared on an ABI Model 431A Peptide Synthesizer using Version 1.12 of the standard BOC software. 4-methyl benzhydrylamine resin (0.46 g, 0.5 mmol) was used in the synthesis. Boc-D-Cys(MOB)-OH (MW 341.43, 0.682 g, 2 mmol), was supplied by Bachem California. BOC-D-Arg (Tos)-OH (MW 428.5, 0.856 g, 2 mmol), Boc-D-Thr-(Bzl)-OH (MW 309.37, 0.618 g, 2 mmol), Boc-D-Lys (2-Cl-Z)-OH (MW 414.89, 0.828 g 2 mmol), Boc-D-Trp-OH (MW 304.37, 0.608 g, 2 mmol) and Boc-D-Val-OH (MW 217.27, 0.434 g, 2 mmol) were supplied by Bachem Bioscience. The final weight of the resin was 1.396 g.

The peptide was cleaved from the resin (1.396 g) using 14 mL of HF and 1.4 mL of anisole for 60 min at 0° C. The resin was washed with ether and the peptide extracted with a 1:1 solution of TFA:DCM to give 710 mg of crude peptide. 502 mg of crude peptide was dissolved in 4 L of 8% DMSO (aqueous) pH 5.5 and left to cyclize overnight. The reaction was monitored by HPLC and the solution was lyophilized when the reaction completed.

The crude peptide (502 mg) was purified on a Vydac C-18 column (15μ, 5×25 cm) eluting with a 30–55% gradient of 80% acetonitrile in 0.1% TFA over 120 min at a flow rate of 15 mL per min. Fractions were collected, analyzed by HPLC and pure fractions pooled and lyophilized to give 76 mg. Compound tested Ellman negative.

Amino acid analysis: Arg 1.01 (1), Cys 1.23 (2), Gly 0.95 (1), Lys 1.01 (1), Phe 2.0 (2), Thr 0.82 (1), Trp 1.40 (1), Val 1.03 (1).

EXAMPLE LXXX

D-Arg-D-Lys-cyclo(D-Cys-Gly-Phe-D-Cys)-D-Trp-D-Thr-Pro-D-Val-NH$_2$ (Preferred Peptide (80))

The peptide was prepared on an ABI Model 431A Peptide Synthesizer using Version 1.12 of the standard BOC software. 4-methyl benzhydrylamine resin (0.46 g, 0.5 mmol) was used in the synthesis. Boc-D-Cys(MOB)-OH (MW 341.43, 0.682 g, 2 mmol), was supplied by Bachem California. BOC-D-Arg (Tos)-OH (MW 428.5, 0.856 g, 2 mmol), Boc-D-Thr-(Bzl)-OH (MW 309.37, 0.618 g, 2 mmol), Boc-D-Lys (2-Cl-Z)-OH (MW 414.89, 0.828 g 2 mmol), Boc-D-Trp-OH (MW 304.37, 0.608 g, 2 mmol) and Boc-D-Val-OH (MW 217.27, 0.434 g, 2 mmol) were supplied by Bachem Bioscience. The final weight of the resin was 1.648 g.

The peptide was cleaved from the resin (1.529 g) using 15 mL of HF and 1.5 mL of anisole for 60 min at 0° C. The resin was washed with ether and the peptide extracted with a 1:1 solution of TFA:DCM to give 565 mg of crude peptide.

The crude peptide (565 mg) was purified on a Vydac C-18 column (15μ, 5×25 cm) eluting with a 30–70% gradient of 80% ethanol in 0.1% TFA over 120 min at a flow rate of 15 mL per min. Fractions were collected, analyzed by HPLC and pure fractions pooled and lyophilized to give 170 mg of linear product. 170 mg of linear peptide was dissolved in 500 mL of 8% DMSO (aqueous) pH 5.5 and left to cyclize overnight. The reaction was monitored by HPLC and lyophilized when complete.

The peptide was then purified on a Vydac C-18 column (15μ, 5×25 cm) eluting with a 30–70% gradient of 80% ethanol in 0.1% TFA over 120 min at a flow rate of 15 mL per min. Fractions were collected, analyzed by HPLC, pooled and lyophilized to give 47 mg. Compound tested Ellman negative.

Amino acid analysis: Arg 1.0 (1), Cys 0.18 (2), Gly 1.02 (1), Lys 1.0 (1), Phe 0.99 (1), Pro 1.62 (1), Thr 0.75 (1), Trp 1.0 (1), Val 0.99 (1).

EXAMPLE LXXXI

D-Arg-D-Lys-cyclo-desthio(D-Cys-Gly-Phe-D-Cys)-D-Trp-D-Thr-D-Trp-D-Val-NH$_2$ (Preferred Peptide (81))

200 mg (0.1575 mmol) of peptide (2101-40-C) was dissolved in 30 mL of 30% acetic acid. To this was added 200 mg Hg(OAc)$_2$ (0.630 mmol), followed by 484 mg dithiothreitol (3.15 mmol). The solution was centrifuged at 3000 RPM for 1 hr and purified by HPLC. Fractions were collected, analyzed by HPLC, pooled and lyophilized to yield 150 mg.

200 mg of linear peptide (100 mg from 2293-41B and 100 mg from 2293-41C) was dissolved in 1 liter of an 8% (aqueous) solution of DMSO. The pH was kept at 5.5 for 24 hrs. The reaction was monitored by HPLC and the resultant solution was lyophilized.

The cyclized product was purified on a Vydac C-18 column (15μ, 5×25 cm) eluting with a 30–55% gradient of 80% acetonitrile in 0.1% TFA over 120 min at a flow rate of 15 mL per min. Fractions were collected, analyzed by HPLC and fractions pooled and lyophilized to give 53 mg. Compound tested negative to Ellman Reagent.

Amino acid analysis: Arg 1.0 (1), Cys 2.12 (2), Gly 1.24 (1), Lys 1.00 (1), Phe 1.00 (1), Thr 0.77 (1), Trp 2.77 (2), Val 1.00 (1). FAB/MS: 1251.2

EXAMPLE LXXXII

D-Arg-D-Lys-cyclo(D-Cys-Gly-Phe-D-Cys)-Pro-D-Thr-D-Trp-D-Val-NH$_2$ (Preferred Peptide (82))

The peptide was prepared on an ABI Model 431A Peptide Synthesizer using Version 1.12 of the standard BOC software. 4-methyl benzhydrylamine resin (0.46 g, 0.5 mmol) was used in the synthesis. Boc-D-Cys(MOB)-OH (MW 341.43, 0.682 g, 2 mmol), was supplied by Bachem California. BOC-D-Arg (Tos)-OH (MW 428.5, 0.856 g, 2 mmol), Boc-D-Thr-(Bzl)-OH (MW 309.37, 0.618 g, 2 mmol), Boc-D-Lys (2-Cl-Z)-OH (MW 414.89, 0.828 g 2 mmol), Boc-D-Trp-OH (MW 304.37, 0.608 g, 2 mmol) and Boc-D-Val-OH (MW 217.27, 0.434 g, 2 mmol) were supplied by Bachem Bioscience. The final weight of the resin was 1.496 g.

The peptide was cleaved from the resin (1.480 g) using 15 mL of HF and 1.5 mL of anisole for 60 min at 0° C. The resin solution of TFA:DCM to give 705 mg of crude peptide. 305 mg of crude peptide was dissolved in 1800 mL of 86 DMSO (aqueous) pH 6.0 and left to stir for 42 hrs. The reaction was monitored by HPLC and lyophilized when complete.

The crude peptide (305 mg) was purified on a Vydac C-18 column (15μ, 5×25 cm) eluting with a 30–70% gradient of 80% ethanol in 0.1% TFA over 120 min at a flow rate of 15 mL per min. Fractions were collected, analyzed by HPLC and pure fractions pooled and lyophilized to give 51 mg. Compound tested Ellman negative.

Amino acid analysis: Arg 1.01 (1), Cys 1.67 (2), Gly 0.96 (1), Lys 1.0 (1), Phe 1.01 (1), Pro 1.37 (1), Thr 0.80 (1), Trp 1.40 (1), Val 1.02 (1).

EXAMPLE LXXXIII

D-Arg-D-Lys-cyclo(D-Cys-Pro-Gly-D-Cys)-D-Trp-D-Thr-D-Trp-D-Val-NH$_2$ (Preferred Peptide (83))

The peptide was prepared on an ABI Model 431A Peptide Synthesizer using Version 1.12 of the standard BOC software. 4-methyl benzhydrylamine resin (0.625 g, 0.5 mmol) was used in the synthesis. Boc-D-Cys(Mob)-OH (MW 341.43, 0.682 g, 2 mmol), Boc-D-Arg(Tos)-OH (MW 428.5, 0.856 g, 2 mmol), Boc-D-Thr-(Bzl)-OH (MW 309.37, 0.618 g, 2 mmol), Boc-D-Lys(2-Cl-Z)-OH (MW 414.89, 0.828 g, 2 mmol) Boc-D-Trp-OH (MW 304.37, 0.608 g 2 mmol) and Boc-D-Val-OH (MW 217.27, 0.434 g, 2 mmol) were supplied by Bachem Bioscience. The final weight of the resin was 1.696 g.

The peptide was cleaved from the resin (1.696 g) using 17 mL of HF and 1.7 mL of anisole for 60 min at 0° C. The resin was washed with ether and the peptide extracted with a 1:1 solution of TFA:DCM to give 800 mg of crude peptide. The crude linear peptide (611 mg) was dissolved in 100 mL of 30% AcOH and then added dropwise to the mixture of water (2000 mL), NH$_4$OH (to keep pH approx. 7.5) and 0.01M K$_3$Fe(CN)$_6$ (approx. 3 mL). After each addition of the linear precursor to the reaction mixture (approx. 1.5 mL) its pH was adjusted to 7.5 by addition of NH$_4$OH followed by addition of K$_3$Fe(CN)$_6$ solution. The total volume of the 0.01M K$_3$Fe(CN)$_6$ solution used for oxidation was 46 mL. The mixture was stirred over 30 min (pH=7.5). The pH was lowered by the addition of ACOH followed by stirring with 15 g of anion exchange resin AG 3-X4, 200–400 mesh, free base form (Bio-Rad) over 30 min. The resin was filtered off and the solution lyophilized.

The crude peptide was purified on a Vydac C-18 column (15μ, 5×25 cm) eluting with a 30–50% gradient of 80% acetonitrile in 0.1% TFA over 120 min at a flow rate of 15 mL per min. Fractions were collected, analyzed by HPLC and pure fractions pooled and lyophilized to give 130 mg.

Amino acid analysis: Arg 0.97 (1), Cys 1.29 (2), Gly 1.04 (1), Lys 0.97 (1), Pro 1.43 (1), Thr 0.75 (1), Trp 1.28 (2), Val 0.96 (1).

EXAMPLE LXXXIV

D-Arg-D-Lys-cyclo(D-Cys-Pro-Phe-D-Cys)-D-Trp-D-Thr-D-Trp-D-Val-NH$_2$ (Preferred Peptide (84))

The peptide was prepared on an ABI Model 431A Peptide Synthesizer using Version 1.12 of the standard BOC software. 4-methyl benzhydrylamine resin (0.625 g, 0.5 mmol) was used in the synthesis. The final weight of the resin was 1.65 g.

The peptide was cleaved from the resin (1.65 g) using 17 mL of HF and 1.7 mL of anisole for 60 min at 0° C. The resin was washed with ether and the peptide extracted with 50% TFA in DCM to give 501 mg of crude peptide. The crude peptide (501 mg) was cyclized at room temperature by air in the presence of copper wire at pH 8.5 in 500 mL ammonium acetate.

The crude peptide (228 mg) was purified on a Vydac C-18 column (15μ, 5×25 cm) eluting with a 25–65% gradient of 80% acetonitrile in 0.1% TFA over 120 min at a flow rate of 15 mL per min. Fractions were collected, analyzed by HPLC and pure fractions pooled and lyophilized to give 60 mg.

Amino acid analysis: Arg 0.91 (1), Cys 1.50 (2), Lys 0.91 (1), Phe 0.98 (1), Pro 1.27 (1), Thr 0.72 (1), Trp 1.08 (2), Val 1.00 (1).

EXAMPLE LXXXV

D-Arg-D-Lys-cyclo(D-Cys-Gly-Pro-D-Cys)-D-Trp-D-Thr-D-Trp-D-Val-NH$_2$ (Preferred Peptide (85))

The peptide was prepared on an ABI Model 431A Peptide Synthesizer using Version 1.12 of the standard BOC software. 4-methyl benzhydrylamine resin (0.625 g, 0.5 mmol) was used in the synthesis. BOC-D-Cys(MOB)-OH (MW 341.43, 0.682 g, 2 mmol), BOC-D-Arg (TOS)-OH (MW 428.5, 0.856 g, 2 mmol) BOC-D-Thr-(Bzl)-OH (MW 309.37, 0.618 g, 2 mmol), BOC-D-Lys(2-Cl-Z)-OH (MW 414.89, 0.828 g, 2 mmol), BOC-D-Trp-OH (MW 304.37, 0.608 g, 2 mmol), and BOC-D-Val-OH (MW 217.27, 0.434 g, 2 mmol) were supplied by Bachem Bioscience. The final weight of the resin was 1.605 g.

The peptide was cleaved from the resin (1.605 g) using 16 mL of HF and 1.6 mL of anisole for 60 min at 0° C. The resin was washed with ether and the peptide extracted with a 1:1 solution of TFA:DCM to give 671 mg of crude peptide. The crude linear peptide (488 mg) was dissolved in 50 mL of 40% AcOH and then added dropwise to the mixture of water (1400 mL), NH$_4$OH (to keep pH approx. 7.5) and 0.01M K$_3$Fe(CN)$_6$ (approx. 3 mL). After each addition of the linear precursor to the reaction mixture, the pH was adjusted to 7.5 by addition of NH$_4$OH followed by addition of K$_3$Fe(CN)$_6$ solution. The total volume of the 0.01M K$_3$Fe(CN)$_6$ solution used for oxidation was 50 mL. The mixture was stirred over 30 min (pH=7.5). The pH was lowered with the addition of AcOH followed by stirring with 12 g of anion exchange resin AG 3-X4, 200–400 mesh, free base form (Bio-Rad) over 30 min. The resin was filtered off, the liquid lyophilized, and the residue was directly purified.

The crude peptide was purified on a Vydac C-18 column (15μ, 5×25 cm) eluting with a 25–45% gradient of 80% acetonitrile in 0.1% TFA over 120 min at a flow rate of 15 mL per min. Fractions were collected, analyzed by HPLC and pure fractions pooled and lyophilized to give 70 mg.

Amino acid analysis: Arg 0.99 (1), Cys 1.69 (2), Gly 1.02 (1), Lys 0.99 (1), Pro 1.20 (1), Thr 0.91 (1), Trp 1.71 (2), Val 1.01 (1).

EXAMPLE LXXXVI

D-Arg-D-Lys-cyclo(D-Cys-Gly-Tic-D-Cys)-D-Trp-D-Thr-D-Trp-D-Val-NH$_2$ (Preferred Peptide (86))

The peptide was prepared on an ABI Model 431A Peptide Synthesizer using Version 1.12 of the standard BOC software. 4-methyl benzhydrylamine resin (0.46 g, 0.5 mmol) was used in the synthesis. N-Boc-L-1,2,3,4-tetrahydroisoquinoline-3-carboxylic acid (Boc-Tic) was purchased from Bachem Bioscience, Inc. (Lot #124162). The final weight of the resin was 1.25 g.

The peptide was cleaved from the resin (1.2 g) using 12 mL of HF and 1.2 mL of anisole for 60 min at 0° C. The resin was washed with ether and the peptide extracted with TFA/DCM (1:1, v/v) (3×15 mL) to give 620 mg of crude peptide. The crude linear peptide (610 mg) was dissolved in 80 mL of 70% AcOH and then added dropwise to the mixture of water (1200 mL), NH$_4$OH (to keep pH approx. 7.5) and 0.01M K$_3$Fe(CN)$_6$ (approx. 3 mL). After each addition of the linear precursor to the reaction mixture (approx. 1.5 mL) its pH was adjusted to 7.5 by addition of NH$_4$OH followed by addition of K$_3$Fe(CN)$_6$ solution. The total volume of the 0.01M K$_3$Fe(CN)$_6$ solution used for oxidation was 61 mL. The 2 mL of K$_3$Fe(CN)$_6$ solution was added extra and the mixture was stirred over 20 min (pH= 7.5), then the pH was adjusted to 4–5 by addition of AcOH followed by stirring with 5 g of anion exchange AG 3-X4, 200–400 mesh, free base form (Bio-Rad) over 30 min. The resin was filtered off, washed with 5% acetic acid (3×100 mL) and combined fractions (approx. 1800 mL) were loaded onto a Vydac C-18 column (15µ, 10×30 cm) eluting with a 0–30% gradient over 5 min and 1 30–65% gradient of 80% ethanol in 0.1% TFA over 55 min at a flow rate of 120 mL per min. Fractions were collected, analyzed by HPLC and pure fractions pooled and evaporated to approximately 100 mL and lyophilized to give 47.1 mg of white solid.

Amino acid analysis: Arg 0.93 (1), Cys 3.51 (2), Gly 1.22 (1), Lys 0.93 (1), Thr 0.59 (1), Trp 2.22 (2), Val 0.93 (1).

FAB/MS: MH$^+$ 1295.8

EXAMPLE LXXXVII

D-Arg-D-Lys-cyclo(D-Cys-Gly-Tyr-D-Cys)-D-Trp-D-Thr-D-Trp-D-Val-NH$_2$ (Preferred Peptide (87))

The peptide was prepared on an ABI Model 431A Peptide Synthesizer using Version 1.12 of the standard Boc software. 4-methyl benzhydrylamine resin (0.47 g, 0.5 mmol) was used in the synthesis. The final weight of the resin was 1.47 g.

The peptide was cleaved from the resin (1.4 g) using 14 mL of HF and 1.4 mL of anisole for 60 min at 0° C. The resin was washed with ether and the peptide extracted with TFA/DCM (1:1, v/v) (3×15 mL) to give 700 mg of crude peptide.

The crude linear peptide (300 mg) was dissolved in 80 mL of 60% AcOH and then added dropwise to the mixture of water (800 mL), NH$_4$OH (to keep pH approx. 7.5) and 0.01M K$_3$Fe(CN), (approx. 3 mL). After each addition of the linear precursor to the reaction mixture (approx. 1.5 mL) its pH was adjusted to 7.5 by addition of NH$_4$OH followed by addition of K$_3$Fe(CN)$_6$ solution. The total volume of the 0.01M K$_3$Fe(CN)$_6$ solution used for oxidation was 38 mL. The 2 mL of K$_3$Fe(CN)$_6$ solution was added extra and the mixture was stirred over 20 min (pH=7.5), then the pH was adjusted to 4–5 by addition of AcOH followed by stirring with 5 g of anion exchange AG 3-X4, 200–400 mesh, free base form (Bio-Rad) over 30 min. The resin was filtered off, washed with 5% acetic acid (3×100 mL) and combined fractions (approx. 1100 mL) were loaded onto a Vydac C-18 column (15µ, 10×30 cm) eluting with a 30–60% gradient of 80% ethanol in 0.1% TFA over 120 min at a flow rate of 60 mL per min. Fractions were collected, analyzed by HPLC and pure fractions pooled and lyophilized to give 42 mg of white solid.

Amino acid analysis: Arg 1.00 (1), Cys 2.51 (2), Gly 1.04 (1), Lys 1.00 (1), Thr 0.74 (1), Trp 2.60 (2), Tyr 0.99 (1) Val 0.98 (1).

FAB/MS: MH$^+$ 1299.4

EXAMPLE LXXXVIII

D-Arg-D-Lys-cyclo-desthio(D-Cys-Gly-Tyr-D-Cys)-D-Trp-D-Thr-D-Trp-D-Val-NH$_2$ (Preferred Peptide (88))

The peptide was prepared on an ABI Model 431A Peptide Synthesizer using Version 1.12 of the standard Boc software. 4 methyl benzhydrylamine resin (0.47 g, 0.5 mmol) was used in the synthesis. The final weight of the resin was 1.47 g.

The peptide was cleaved from the resin (1.4 g) using 14 mL of HF and 1.4 mL of anisole for 60 min at 0° C. The resin was washed with ether and the peptide extracted with TFA/DCM (1:1, v/v) (3×15 mL) to give 700 mg of crude peptide. The crude, linear peptide (350 mg) was dissolved in 100 mL of DMSO, diluted with 900 mL of water and stirred over 20 hrs (pH was brought to 6.5 by addition of NH$_4$OH). The solution (approx. 1000 mL) was loaded onto a Vydac C-18 column (15µ, 10×30 cm) eluting with a 30–65% gradient of 80% ethanol in 0.1% TFA over 120 min at a flow rate of 60 mL per min. Fractions were collected, analyzed by HPLC and pure fractions pooled and lyophilized to give 25 mg of white solid.

Amino acid analysis: Arg 1.01 (1), Gly 1.02 (1), Lys 1.0 (1), Thr 0.70 (1), Trp 2.70 (2), Tyr 1.00 (1), Val 0.98 (1), Lan (Lanthionine) 0.99 (1).

FAB/MS: MH$^+$ 1267.7

EXAMPLE LXXXIX

D-Arg-D-Lys-cyclo(D-Cys-Gly-Val-D-Cys)-D-Trp-D-Thr-D-Trp-D-Val-NH$_2$ (Preferred Peptide (89))

The peptide was prepared on an ABI Model 431A Peptide Synthesizer using Version 1.12 of the standard BOC software. 4-methyl benzhydrylamine resin (455, mg, 0.5 mmol) was used in the synthesis. The final weight of the resin was 1.36 g.

The peptide was cleaved from the resin (1.36 g) using 14 mL of HF and 1.4 mL of anisole for 60 min at OOC. The resin was washed with ether and the peptide extracted with 30% acetic acid to give 604 mg of crude peptide. 550 mg of crude peptide was cyclized in 50 mL of DMSO and 1.1 liters of water stirring for 3 days at pH 6 and at room temperature; then lyophilized.

The crude peptide was purified on a Vydac C-18 column (15µ, 5×25 cm) eluting with a 31–45% gradient of 80% acetonitrile in 0.1% TFA over 120 min at a flow rate of 15 mL per min. Fractions were collected, analyzed by HPLC and pure fractions pooled and lyophilized to give 22 mg of pure peptide.

Amino acid analysis: Arg 0.98 (1), Cys 1.11 (2), Gly 1.12 (1), Lys 0.97 (1), Thr 0.73 (1), Trp 2.33 (2), Val 1.92 (2).

FAB/MS: MH$^+$ 1235.5

EXAMPLE XC

D-Arg-D-Lys-cyclo(D-Cys-Gly-Phe-D-Cys)-D-Trp-
D-Thr-D-Arg-D-Val-NH$_2$ (Preferred Peptide (90))

The peptide was prepared on an ABI Model 431A Peptide Synthesizer using Version 1.12 of the standard BOC software. 4-methyl benzhydrylamine resin (460 mg, 0.5 mmol) was used in the synthesis. All Boc-D-amino acids were purchased from Bachem Bioscience, Inc. The final weight of the resin was 1.48 g.

The peptide was cleaved from the resin (1.48 g) using 15 mL of HF and 1.5 mL of anisole for 60 min at 0° C. The resin was washed with ether and the peptide extracted with 50% TFA in DCM to give 562 mg of crude peptide. The linear crude peptide (562 mg) was cyclized in 600 mL of 10% DMSO at pH 6.5 overnight.

The crude cyclized peptide (562 mg) was purified on a Vydac C-18 column (15µ, 5×25 cm) eluting with a 10–50% gradient of 80% acetonitrile in 0.1% TFA over 120 min at a flow rate of 15 mL per min. Fractions were collected, analyzed by HPLC and pure fractions pooled and lyophilized to give 104 mg.

Amino acid analysis: Arg 1.93 (2), Cys 3.24 (2), Gly 1.16 (1), Lys 0.97 (1), Phe 0.96 (1), Thr 0.74 (1), Trp 0.85 (1) Val 0.98 (1)

EXAMPLE LCI

D-Arg-D-Lys-cyclo(D-Cys-Gly-Phe-Cys)-D-Trp-D-
Thr-D-Trp-D-Val-NH$_2$ (Preferred Peptide (91))

The peptide was prepared on an ABI Model 431A Peptide Synthesizer using Version 1.12 of the standard BOC software. 4-methyl benzhydrylamine resin (0.625 g, 0.5 mmol) was used in the synthesis. Boc-D-Cys(MOB)-OH (MW 341.43, 0.682 g, 2 mmol), BOC-D-Arg (Tos)-OH (MW 428.5, 0.856 g, 2 mmol), Boc-D-Thr-(Bzl)-OH (MW 309.37, 0.618 g, 2 mmol), Boc-D-Lys (2-Cl-Z)-OH (MW 414.89, 0.828 g 2 mmol), Boc-D-Trp-OH (MW 304.37, 0.608 g, 2 mmol) and Boc-D-Val-OH (MW 217.27, 0.434 g, 2 mmol) were supplied by Bachem Bioscience. The final weight of the resin was 1.699 g.

The peptide was cleaved from the resin (1.595 g) using 16 mL of HF and 1.6 mL of anisole for 60 min at 0° C. The resin was washed with ether and the peptide extracted with a 1:1 solution of TFA:DCM to give 1.217 g of crude linear phe crude linear peptide (511 mg) was dissolved in 100 mL of 30% ACOH and then added dropwise to the mixture of water (1800 mL), NH$_4$OH (to keep pH approx. 7.5) and 0.01M K$_3$Fe(CN)$_6$ (approx. 3 mL). After each addition of the linear precursor to the reaction mixture (approx. 1.5 mL) its pH was adjusted to 7.5 by addition of NH$_4$OH followed by addition of K$_3$Fe(CN)$_6$ solution. The total volume of the 0.01M K$_3$Fe(CN)$_6$ solution used for oxidation was 20 mL. The mixture was stirred over 20 min (pH=7.5), then the pH was lowered with the addition of AcOH followed by stirring with 5 g of anion exchange AG 3-X4, 100–200 mesh, free base form (Bio-Rad) over 30 min. The resin was filtered off, the solution was lyophilized and the product directly purified.

The crude peptide was purified on a Vydac C-18 column (15µ, 5×25 cm) eluting with a 35–60% gradient of 80% acetonitrile in 0.1% TFA over 120 min at a flow rate of 15 mL per min. Fractions were collected, analyzed by HPLC and pure fractions pooled and lyophilized to give 29 mg.

Amino acid analysis: Arg 0.97 (1), Cys 1.03 (2), Gly 1.82 (1), Lys 1.0 (1), Phe 1.0 (1), Thr 0.61 (1), Trp 2.14 (2), Val 1.03 (1).

EXAMPLE XCII

D-Arg-D-Lys-cyclo(D-Cys-D-Ile-Ile-D-Cys)-D-Trp-
D-Thr-D-Trp-D-Val-NH$_2$ (Preferred Peptide (92))

The peptide was prepared on an ABI Model 431A Peptide Synthesizer using Version 1.12 of the standard BOC software. 4-methyl benzhydrylamine resin (0.46 g, 0.5 mmol) was used in the synthesis. Boc-D-Ile-OH (MW 231.29, 0.462 g, 2 mmol, Boc-D-Cys(MOB)-OH (MW 341.43, 0.682 g, 2 mmol), BOC-D-Arg (Tos)-OH (MW 428.5, 0.856 g, 2 mmol), Boc-D-Thr-(Bzl)-OH (MW 309.37, 0.618 g, 2 mmol), Boc-D-Lys (2-Cl-Z)-OH (MW 414.89, 0.828 g 2 mmol), Boc-D-Trp-OH (MW 304.37, 0.608 g, 2 mmol) and Boc-D-Val-OH (MW 217.27, 0.434 g, 2 mmol) were supplied by Bachem Bioscience. The final weight of the resin was 1.611 g.

The peptide was cleaved from the resin (1.526 g) using 15 mL of HF and 1.5 mL of anisole for 60 min at 0° C. The resin was washed with ether and the peptide extracted with a 1:1 solution of TFA:DCM to give 789 mg of crude peptide. 200 mg of crude peptide was cyclized in 2 liters of 8% DMSO (aqueous) at a pH of 5.5 for 24 hrs. The reaction was monitored by HPLC and when completed, the reaction mixture was lyophilized to a yellow oil.

The crude peptide was purified on a Vydac C-18 column (15µ, 5×25 cm) eluting with a 35–60% gradient of 80% acetonitrile in 0.1 TFA over 120 min at a flow rate of 15 mL per min. Fractions were collected, analyzed by HPLC and pure fractions pooled and lyophilized to give 35 mg. Compound tested Ellman negative.

Amino acid analysis: Arg 1.0 (1), Cys 2.26 (2), Ile 1.16 (2), Lys 1.0 (1), Thr 0.75 (1), Trp 2.54 (2), Val 1.0 (1).

EXAMPLE XCIII

D-Arg-D-Lys-cyclo(D-Cys-D-Ile-Phe-D-Cys)-D-
Trp-D-Thr-D-Trp-D-Val-NH$_2$ (Preferred Peptide (93))

The peptide was prepared on an ABI Model 431A Peptide Synthesizer using Version 1.12 of the standard BOC software. 4-methyl benzhydrylamine resin (460 mg, 0.5 mmol) was used in the synthesis. All D-Boc amino acids were purchased from Bachem Bioscience, Inc. The final weight of the resin was 1.29 g.

The Cys-acm-protected peptide was cleaved from the resin (1.29 g) using 13 mL of HF and 1.3 mL of anisole for 60 min at 0° C. The resin was washed with ether and the peptide extracted with 50% TFA in DCM to give 225 mg of crude peptide. The peptide (225 mg) was deprotected with 2 equivalents of Hg(OAc)$_2$ and 20 equivalents of DTT then desalted on a Vydac C-18 column (15µ, 5×25 cm) with a 25–65% gradient of 80% acetonitrile in 0.1% TFA over 120 min at 15 mL/min. The peptide (45 mg) was cyclized with 50 mL of 10% aqueous DMSO at pH 7.5 overnight.

The crude peptide (45 mg) was purified on a Vydac C-18 column (15µ, 5×25 mL) eluting with a 25–65% gradient of 80% acetonitrile in 0.1% TFA over 120 min at a flow rate of 15 mL per min. Fractions were collected, analyzed by HPLC and pure fractions pooled and lyophilized to give 10 mg.

Amino acid analysis: Arg 1.05 (1), Cys 2.20 (2), Ile 0.90 (1), Lys 1.03 (1), Phe 0.96 (1), Thr 0.82 (1?, Trp 2.47 (2), Val 1.06 (1).

EXAMPLE XCIV

D-Arg-D-Lys-cyclo(D-Cys-His-Phe-D-CyB)-D-Trp-D-Thr-D-Trp-D-Val-NH$_2$ (Preferred Peptide (94))

The peptide was prepared on an ABI Model 431A Peptide Synthesizer using Version 1.12 of the standard BOC software. 4-methyl benzhydrylamine resin (460 mg, 0.5 mmol) was used in the synthesis. All D-Boc-amino acids were purchased from Bachem Bioscience, Inc. The final weight of the resin was 1.56 g.

The peptide was cleaved from the resin (1.4 g) using 14 mL of HF and 1.4 nL of anisole for 60 min at 0° C. The resin was washed with ether and the peptide extracted with 50% TFA in DCM to give 487 mg of crude linear peptide. The peptide (487 mg) was cyclized in 500 mL of 10% DMSO at pH 6.5 overnight.

The crude peptide (487 mg) was purified on a Vydac C-18 column (15µ, 5×25 cm) eluting with a 20–60% gradient of 80% ethanol in 0.1% TFA over 120 min at a flow rate of 15 mL per min. Fractions were collected, analyzed by HPLC and pure fractions pooled and lyophilized to give 52 mg.

Amino acid analysis: Arg 1.02 (1), Cys 2.46 (2), His 0.92 (1), Lys 1.02 (1), Phe 1.02 (1), Thr 0.79 (1), Trp 2.78 (2), Val 1.02 (1).

EXAMPLE XCV

D-Arg-D-Lys-cyclo(D-Cys-Ile-Pro-D-Cys)-D-Trp-D-Thr-D-Trp-D-Val-NH$_2$ (Preferred Peptide (95))

The peptide was prepared on an ABI Model 431A-Peptide Synthesizer using Version 1.12 of the standard BOC software. 4-methyl benzhydrylamine resin (0.46 g, 0.5 mmol) was used in the synthesis. The final weight of the resin was 1.37 g.

The peptide was cleaved from the resin (1.30 g) using 15 mL of HF and 1.5 mL anisole for 60 min at 0° C. The resin was washed with ether and ether/methylene chloride 1:1 and the peptide extracted with 50% TFA in methylene chloride to give 0.64 g of crude peptide after ether precipitation. The crude linear peptide (0.63 g) was dissolved in 100 mL of water, adjusted to pH 7 and pumped into 1000 mL of 10% DMSO over 24 hr. After an additional 24 hr there was no further change by HPLC.

The crude peptide solution was loaded onto a Vydac C-18 column (15µ, 10×30 cm) eluting with a 20–80% gradient of 80% ethanol in 0.1% TFA over 120 min at a flow rate of 60 mL per min. Fractions were collected, analyzed by HPLC and pure fractions pooled and lyophilized to give 0.115 g. The material was Elman negative.

Amino acid analysis: Arg 0.95 (1), Cys 2.34 (2), Ile 0.79 (2), Lys 0.94 (1), Pro 1.36 (1), Thr 0.71 (1), Trp 2.58 (2), Val 0.95 (1). Ile-Ile is a difficult sequence to hydrolyze.

EXAMPLE XCVI

D-Arg-D-Lys-cyclo(D-Cys-Gly-Phe-D-Cys)-D-Trp-D-Thr-Trp-D-Val-NH$_2$ (Preferred Peptide (96))

The peptide was prepared on an ABI Model 431A Peptide 4-methyl benzhydrylamine resin (0.625 g, 0.5 mmol) was used in the synthesis. Boc-D-Cys(MOB)-OH (MW 341.43, 0.682 g, 2 mmol), BOC-D-Arg (Tos)-OH (MW 428.5, 0.856 g, 2 mmol), Boc-D-Thr-(Bzl)-OH (MW 309.37, 0.618 g, 2 mmol), Boc-D-Lys (2-Cl-Z)-OH (MW 414.89, 0.828 g 2 mmol), Boc-D-Trp-OH (MW 304.37, 0.608 g, 2 mmol) and Boc-D-Val-OH (MW 217.27, 0.434 g, 2 mmol) were supplied by Bachem Bioscience. The final weight of the resin was 1.629 g.

The peptide was cleaved from the resin (1.629 g) using 16 mL of HF and 1.6 mL of anisole for 60 min at 0° C. The resin was washed with ether and the peptide extracted with a 1:1 solution of TFA:DCM to give 500 mg of crude peptide. The crude linear peptide (392 mg) was dissolved in 50 mL of 50% AcOH and then added dropwise to the mixture of water (1400 mL), NH$_4$OH (to keep pH approx. 7.5) and 0.01M K$_3$Fe(CN)$_6$ (approx. 3 mL). After each addition of the linear precursor to the reaction mixture (approx. 1.5 mL) its pH was adjusted to 7.5 by addition of NH$_4$OH followed by addition of K$_3$Fe(CN)$_6$ solution. The total volume of the 0.01M K$_3$Fe(CN)$_6$ solution used for oxidation was 38 mL. The mixture was stirred over 20 min (pH=7.5), then the pH was adjusted to 4–5 by addition of AcOH followed by stirring with 5 g of anion exchange AG 3-X4, 100–200 mesh, free base form (Bio-Rad) over 30 min. The resin was filtered off, the solution lyophilized and directly purified.

The crude peptide was purified on a Vydac C-18 column (15µ, 5×25 cm) eluting with a 35–60% gradient of 80% acetonitrile in 0.1% TFA over 120 min at a flow rate of 15 mL per min. Fractions were collected, analyzed by HPLC and pure fractions pooled and lyophilized to give 36 mg.

Amino acid analysis: Arg 1.0 (1), Cys 0.54 (2), Gly 1.12 (1), Lys 0.99 (1), Phe 0.99 (1), Thr 0.60 (1), Trp 1.93 (2), Val 1.02 (1).

EXAMPLE XCVII

D-Arg-D-Lys-cyclo(D-Cys-Gly-Phe-D-Cys)-D-Trp-D-Thr-D-Trp-Val-NH$_2$ (Preferred Peptide (97))

The peptide was prepared on an ABI Model 431A Peptide Synthesizer using Version 1.12 of the standard BOC software. 4-methyl benzhydrylamine resin (0.625 g, 0.5 mmol) was used in the synthesis. Boc-D-Cys(MOB)-OH (MW 341.43, 0.682 g, 2 mmol), BOC-D-Arg (Tos)-OH (MW 428.5, 0.856 g, 2 mmol), Boc-D-Thr-(Bzl)-OH (MW 309.37, 0.618 g, 2 mmol), Boc-D-Lys (2-Cl-Z)-OH (MW 414.89, 0.828 g 2 mmol), and Boc-D-Trp-OH (MW 304.37, 0.608 g, 2 mmol) and Boc-D-Val-OH (MW 217.27, 0.434 g, 2 mmol) were supplied by Bachem Bioscience. The final weight of the resin was 1.774 g.

The peptide was cleaved from the resin (1.645 g) using 16 mL of HF and 1.6 mL of anisole for 60 min at 0° C. The resin was washed with ether and the peptide extracted with a 1:1 solution of TFA:DCM to give 653 mg of crude peptide. 414 mg of crude peptide was dissolved in 2 L of 8% DMSO (aqueous) at a pH of 5.5 left to cyclize overnight. The reaction was monitored by HPLC and lyophilized when complete.

The crude peptide was purified on a Vydac C-18 column (15µ, 5×25 cm) eluting with a 30–55% gradient of 80% acetonitrile in 0.1% TFA over 120 min at a flow rate of 15 mL per min. Fractions were collected, analyzed by HPLC and pure fractions pooled and lyophilized to give 39 mg. Compound was Ellman negative.

Amino acid analysis: Arg 0.99 (1), Cys 2.43 (2), Gly 1.04 (1), Lys 1.00 (1), Phe 0.99 (1), Thr 0.74 (1), Trp 2.42 (2), Val 0.97 (1).

EXAMPLE XCVIII

D-Arg-D-Lys-cyclo(D-Cys-Gly-Phe-D-Cys)-D-Trp-Thr-D-Trp-D-Val-NH$_2$ (Preferred Peptide (98))

The peptide was prepared on an ABI Model 431A Peptide Synthesizer using Version 1.12 of the standard BOC software. 4-methyl benzhydrylamine resin (0.625 g, 0.5 mmol) was used in the synthesis. Boc-D-Cys(MOB)-OH (MW 341.43, 0.682 g, 2 mmol), BOC-D-Arg (Tos)-OH (MW 428.5, 0.856 g, 2 mmol), Boc-D-Lys (2-Cl-Z)-OH (MW 414.89, 0.828 g 2 mmol), Roc-D-Trp-OH (MW 304.37, 0.608 g, 2 mmol) and Boc-D-Val-OH (MW 217.27, 0.434 g, 2 mmol) were supplied by Bachem Bioscience. The final weight of the resin was 1.796 g.

The peptide was cleaved from the resin (1.796 g) using 18 mL of HF and 1.8 mL of anisole for 60 min at 0° C. The resin was washed with ether and the peptide extracted with a 1:1 solution of TFA:DCM to give 784 mg of crude peptide. The crude linear peptide (396 mg) was dissolved in 50 mL of 50% AcOH and then added dropwise to the mixture of water (1400 mL), NH$_4$OH (to keep pH approx. 7.5) and 0.01M K$_3$Fe(CN)$_6$ (approx. 3 mL). After each addition of the linear precursor to the reaction mixture (approx. 1.5 mL) its pH was adjusted to 7.5 by addition of NH$_4$OH followed by addition of K$_3$Fe(CN)$_6$ solution. The total volume of the 0.01M K$_3$Fe(CN)$_6$ solution used for oxidation was 41 mL. The mixture was stirred over 20 min (pH=7.5), then the pH was lowered with the addition of AcOH followed by stirring with 5 g of anion exchange AG 3-X4, 100–200 mesh, free base form (Bio-Rad) over 30 min. The resin was filtered off, the solution lyophilized, and directly purified.

The crude peptide was purified on a Vydac-C-18 column (15μ, 5×25 cm) eluting with a 35–60% gradient of 80% acetonitrile in 0.1% TFA over 120 min at a flow rate of 15 mL per min. Fractions were collected, analyzed by HPLC and pure fractions pooled and lyophilized to give 38 mg. Ellman test was negative.

Amino acid analysis: Arg 1.01 (1), Cys 0.24 (2), Gly 0.90 (1), Lys 1.01 (1), Phe 0.93 (1), Thr 0.69 (1), Trp 2.50 (2), Val 1.04 (1).

EXAMPLE XCIX

D-Arg-D-Lys-cyclo(D-Cys-Gly-Phe-D-Cys)-Trp-D-Thr-D-Trp-D-Val-NH$_2$ (Preferred Peptide (99))

The peptide was prepared on an ABI Model 431A Peptide Synthesizer using Version 1.12 of the standard BOC software. 4-methyl benzhydrylamine resin (0.625 g, 0.5 mmol) was used in the synthesis. Boc-D-Cys(MOB)-OH (MW 341.43, 0.682 g, 2 mmol), BOC-D-Arg (Tos)-OH (MW 428.5, 0.856 g, 2 mmol), Boc-D-Thr-(Bzl)-OH (MW 309.37, 0.618 g, 2 mmol), Boc-D-Lys (2-Cl-Z)-OH (MW 414.89, 0.828 g 2 mmol), Boc-D-Trp-OH (MW 304.37, 0.608 g, 2 mmol) and Boc-D-Val-OH (MW 217.27, 0.434 g, 2 mmol) were supplied by Bachem Bioscience. The final weight of the resin was 1.688 g.

The peptide was cleaved from the resin (1.688 g) using 17 mL of HF and 1.7 mL of anisole for 60 min at 0° C. The resin was washed with ether and the peptide extracted with a 1:1 solution of TFA:DCM to give 711 mg of crude peptide. The crude linear peptide (446 mg) was dissolved in 50 mL of 50% AcOH and then added dropwise to the mixture of water (1800 mL), NH$_4$OH (to keep pH approx. 7.5) and 0.01M K$_3$Fe(CN)$_6$ (approx. 3 mL). After each addition of the linear precursor to the reaction mixture (approx. 1.5 mL) its pH was adjusted to 7.5 by addition of NH$_4$OH followed by addition of K$_3$Fe(CN)$_6$ solution. The total volume of the 0.01M K$_3$Fe(CN)$_6$ solution used for oxidation was 37 mL. The mixture was stirred for 30 min (pH=7.5), then the pH was lowered with the the addition of AcOH, followed by stirring with 5 g of anion exchange AG 3-X4, 100–200 mesh, free base form (Bio-Rad) over 30 min. The resin was filtered and the solution lyophilized, then directly purified.

The crude peptide was purified on a Vydac C-18 column (15μ, 5×25 cm) eluting with a 35–60% gradient of 80% acetonitrile in 0.1% TFA over 120 min at a flow rate of 15 mL per min. Fractions were collected, analyzed by HPLC and pure fractions pooled and lyophilized to give 15 mg.

Amino acid analysis: Arg 0.99 (1), Cys 1.12 (2), Gly 1.03 (1), Lys 0.99 (1), Phe 1.0 (1), Thr 0.79 (1), Trp 2.87 (2), Val 1.0 (1).

EXAMPLE C

D-Arg-D-Lys-cyclo(D-Cys-Gly-Phe-D-Cys)-D-Tyr-D-Thr-D-Gln-D-Val-NH$_2$ (Preferred Peptide (100))

The peptide was prepared on an ABI Model 431A Peptide Synthesizer using Version 1.12 of the standard BOC software. 4-methyl benzhydrylamine resin (460 mg, 0.5 mmol) was used in the synthesis. All D-Boc-amino acids were purchased from Bachem Bioscience, Inc. The final weight of the resin was 1.2 g.

The peptide was cleaved from the resin (1.2 g) using 12 mL of HF and 1.2 mL of anisole for 60 min at 0° C. The resin was washed with ether and the peptide extracted with 50% TFA in DCM to give 389 mg of crude peptide. The crude peptide (389 mg) was oxidized with 400 mL of 10% aqueous DMSO at pH 6.5 overnight.

The crude peptide (389 mg) was purified on a Vydac C-18 column (15μ, 5×25 cm) eluting with a 10–50% gradient of 80% acetonitrile in 0.1% TFA over 120 min at a flow rate of 15 mL per min. Fractions were collected, analyzed by HPLC and pure fractions pooled and lyophilized to give 174 mg.

Amino acid analysis: Arg 0.96 (1), Cys 0.81 (2), Glx 1.15 (1), Gly 1.01 (1), Lys 0.95 (1), Phe 0.96 (1), Thr 0.81 (1), Tyr 0.98 (1), Val 0.98 (1).

EXAMPLE CI

Arg-D-Lys-cyclo(D-Cys-Gly-Phe-D-Cys)-D-Trp-D-Thr-D-Trp-D-Val-NH$_2$ (Preferred Peptide (101))

The peptide was prepared on an ABI Model 431A Peptide Synthesizer using Version 1.12 of the standard BOC software. 4-methyl benzhydrylamine resin (0.625 g, 0.5 mmol) was used in the synthesis. Boc-D-Cys(MOB)-OH (MW 341.43, 0.682 g, 2 mmol), Boc-D-Thr-(Bzl)-OH (MW 309.37, 0.618 g, 2 mmol), Boc-D-Lys (2-Cl-Z)-OH (MW 414.89, 0.828 g 2 mmol), Boc-D-Trp-OH (MW 304.37, 0.608 g, 2 mmol) and Boc-D-Val-OH (MW 217.27, 0.434 g, 2 mmol) were supplied by Bachem Bioscience. The final weight of the resin was 1.841 g.

The peptide was cleaved from the resin (1.754 g) using 18 mL of HF and 1.8 mL of anisole for 60 min at 0° C. The resin was washed with ether and the peptide extracted with a 1:1 solution of TFA:DCM to give 1.117 g of crude peptide. The crude linear peptide (902 mg) was dissolved in 200 mL of 50% AcOH and then added dropwise to the mixture of water (2800 mL), NH$_4$OH (to keep pH approx. 7.5) and 0.01M K$_3$Fe(CN)$_6$ (approx. 3 mL). After each addition of the linear precursor to the reaction mixture (approx. 1.5 mL), its pH was adjusted to 7.5 by addition of NH$_4$OH, followed by addition of K$_3$Fe(CN)$_6$ solution. The total volume of the 0.01M K$_3$Fe(CN)$_6$ solution used for oxidation was 44 mL. The mixture was stirred for 30 min (pH=7.5), then the pH was lowered with the addition of AcOH, followed by stirring with 5 g of anion exchange AG 3-X4, 100–200 mesh, free base form (Bio-Rad) over 30 min. The resin was filtered off and the solution lyophilized then directly purified.

The crude peptide was purified on a Vydac C-18 column (15μ, 5×25 cm) eluting with a 35–60% gradient of 80% acetonitrile in 0.1% TFA over 120 min at a flow rate of 15 mL per min. Fractions were collected, analyzed by HPLC and pure fractions pooled and lyophilized to give 15 mg.

Amino acid analysis: Arg 0.80 (1), Cys 0.04 (2), Gly 1.71 (1), Lys 0.82 (1), Phe 0.85 (1), Thr 0.77 (1), Trp 1.61 (2), Val 0.83 (1).

EXAMPLE CII

D-Arg-D-Lys-cyclo(D-Cys-Gly-Phe-D-Cys)-D-Trp-D-Thr-D-Trp-Gln-NH-Bu (Preferred Peptide (102))

The peptide was prepared on an ABI Model 431A Peptide Synthesizer using Version 1.12 of the standard BOC software. 4-methyl benzhydrylamine resin (460 mg, 0.5 mmol) was used in the synthesis. The Boc-Gln-NH-Bu (Lot 1575-127, 605 mg, 2 mmol) was used in this synthesis. All D-Boc-amino acids were purchased from Bachem Bioscience, Inc. The final weight of the resin was 1.18 g.

The peptide was cleaved from the resin (1.18 g) using 12 mL of HF and 1.2 mL of anisole for 60 min at 0° C. The resin was washed with ether and the peptide extracted with 50% TFA in DCM to give 280 mg of crude peptide. The peptide (280 mg) was cyclized in 300 mL of 10% DMSO at pH 7.0 overnight.

The crude cyclized peptide (280 mg) was purified on a Vydac C-18 column (15μ, 5×25 cm) eluting with a 25–65% gradient of 80% acetonitrile in 0.1% TFA over 120 min at a flow rate of 15 mL per min. Fractions were collected, analyzed by HPLC and pure fractions pooled and lyophilized to give 60 mg.

Amino acid analysis: Arg 1.01 (1), Cys 3.57 (2), Glx 1.13 (1), Gly 1.01 (1), Lys 0.99 (1), Phe 0.99 (1), Thr 0.71 (1), Trp 2.54 (2).

EXAMPLE CIII

D-Arg-D-Lys-cyclo(D-Cys-Gly-Phe-D-Cys)-D-Trp-D-Val-D-Trp-D-Val (Preferred Peptide (103))

The peptide was prepared on an ABI Model 431A Peptide Synthesizer using Version 1.12 of the standard BOC software. D-Boc-Val-PAM resin (833 mg, 0.5 mmol) was used in the synthesis. The resin and all Boc-D amino acids were purchased from Bachem Bioscience, Inc. The final weight of the resin was 1.57 g.

The peptide was cleaved from the resin (1.50 g) using 15 mL of HF and 1.5 mL of anisole for 60 min at 0° C. The resin was washed with ether and the peptide extracted with 50% TFA in DCM to give 388 mg of crude peptide. The peptide (388 mg) was cyclized with air in the presence of Cu wire (4 cm) in 500 mL of ammonium acetate, pH 8.5 for 22 hours then lyophilized to give 300 mg.

The crude peptide (300 mg) was purified on a Vydac C-18 column (15μ, 5×25 cm) eluting with a 30–70% gradient of 80% acetonitrile in 0.1% TFA over 120 min at a flow rate of 15 mL per min. Fractions were collected, analyzed by HPLC and pure fractions pooled and lyophilized to give 10.6 mg.

Amino acid analysis: Arg 0.99 (1), Cys N.D. (2), Gly 1.03 (1), Lys 1.01 (1), Phe 1.01 (1), Trp N.D. (2), Val 1.90 (2).

EXAMPLE CIV

Ac-D-Lys-cyclo(D-Cys-Gly-Tyr-D-Cys)-D-Trp-D-Thr-D-Trp-D-Val-NH$_2$ (Preferred Peptide (104))

100 mg of 2101-34 was dissolved in 100 mL of 50% acetic acid. A solution of 1 mg/mL I2 (7 mL) was added and the reaction mixture stirred for 4 hr. A solution of 10 mg/mL Na$_2$S$_2$O$_3$ in water was added dropwise to decolorize the reaction mixture. After lyophilization the crude peptide was purified on a Vydac C-18 column (15μ, 5×25 cm) eluting with a 20–60% gradient of 80% acetonitrile in 0.1% TFA over 120 min at a flow rate of 60 mL/min. Fractions were collected, analyzed by HPLC and pure fractions pooled and lyophilized to give 10 mg. The material was Elman negative.

Amino acid analysis: Cys (2) N.D., Gly (1) 1.11, Lys (1) 0.97, Thr (1) 0.70, Trp (2) 1.35, Tyr (1) 0.96, Val (1) 0.96.

EXAMPLE CV

D-Arg-cyclo[D-Lys-cyclo(D-Cys-Gly-Phe-D-Cys)-D-Trp-D-Thr-D-Trp-D-Glu]-NH$_2$ (Preferred Peptide (105))

The N-protected (Boc) peptide was prepared on an ABI Model 431A Peptide Synthesizer using Version 1.12 of the standard Boc software. 4-methyl benzhydrylamine resin (0.47 g, 0.5 mmol) was used in the synthesis. Boc-D-Lys (Fmoc) (Lot ZG 864), Boc-D-Glu(OFm) (Lot ZJ 302) and Boc-D-Cys(Acm) (Lot ZJ 348) were purchased from Bachem, California. The final weight of the resin was 1.35 g.

The Boc-D-Arg(Tos)-D-Lys(Fmoc)-D-Cys(Acm)-Gly-Phe-D-Cys(Acm)-D-Trp-D-Thr(Bzl)-D-Trp-D-Glu(OFm)-resin (1.35 g) was transferred into a manual shaker then treated with 20% piperidine/DMF solution (1×2 min and 1×20 min), followed by overnight coupling (20 hrs) with 2 mmol of BOP reagent, 4 mmol of HOBt in NMP with 6 mmol of DIEA. The protected peptidyl resin was treated with TFA/DCM (1:1, v/v) for 5 min and 25 min, washed with several solvents and dried. Yield: 1.28 g.

The peptide was cleaved from the resin (1.2 g) using 12 mL of HF and 1.2 mL of anisole for 60 min at 0° C. The resin was washed with ether and the peptide extracted with TFA/DCM (1:1, v/v) (3×15 mL) to give 747 mg of crude peptide.

The crude peptide (740 mg) was dissolved in 100 mL of 80% AcOH and purified on a Vydac C-18 column (15μ, 10×30 cm) eluting with a 25–65% gradient of 80% ethanol in 0.1% TFA over 60 min at a flow rate of 120 mL/min. Semipure functions were pooled, evaporated to approx. 100 mL and lyophilized to give 158 mg of white solid.

The Acm containing peptide (158 mg, 0.1098 mmol) (Formula: $C_{66}H_{91}N_{19}O_{14}S_2$, MW=1438.7) was dissolved in 8 mL of 30% AcOH and stirred with mercuric acetate (139.7 mg, 0.44 mmol) over 120 min at room temperature. Dithiothreitol (DTT) (338.7 mg, 2.22 mmol) was added and stirring was continued for 80 min, followed by filtration through a celite layer and 0.2μ filter. The solution of peptide was loaded on a Vydac C-18 column (15μ, 5×25 cm) eluting with a 20–80% gradient of 80% acetonitrile in 0.1% TFA over 120 min at a flow rate of 15 mL/min. Semipure fractions were pooled and lyophilized to give 95 mg of white solid. The product (95 mg) was dissolved in 60 mL of 40% AcOH and then added dropwise to the mixture of water (800 mL) $NH_4OH$ (to keep pH approx. 7.5) and 0.01M $K_3Fe(CN)_6$ (approx. 3 mL). After each addition of the linear precursor to the reaction mixture (approx. 1.5 mL) its pH was adjusted to 7.5 by addition of $NH_4OH$ followed by addition of $MK_3Fe(CN)_6$ solution. The total volume of the 0.01M $K_3Fe(CN)_6$ solution used for oxidation was 11.2 mL. The 2 mL of $K_3Fe(CN)_6$ solution was added extra and the mixture was stirred over 30 min (pH=7.5), then the pH was adjusted to a 4–5 addition of ACOH followed by stirring with 5 g of anion exchange resin AG 3-X4, 200–400 mesh, free base form (Bio-Rad) over 30 min. The resin was filtered off, washed with 5% acetic acid (3×100 mL) and combined fractions were lyophilized to give 140 g of white solid.

The crude peptide (140 mg) was purified on a Vydac C-18 column (15μ, 5×25 cm) eluting with a 25–65% gradient of 80% acetonitrile in 0.1% TFA over 120 min at a flow rate of 15 mL per min. Fractions were collected, analyzed by HPLC and pure fractions pooled and lyophilized to give 22 mg of white solid. The semipure batch (50 mg) was isolated then repurified on a Vydac C-18 column (10μ, 2.2×25 cm), eluting with a 30–65% gradient of 80% acetonitrile in 0.1 TFA over 60 min at a flow rate of 10 mL/min. Fractions were collected, analyzed by HPLC and pure fractions pooled and lyophilized to give 18 mg of white solid. The 22 mg and 18 mg batches were pooled, dissolved in 0.1% FA and lyophilized to give 40 mg of white solid.

Amino acid analysis: Arg 0.99 (1), Cys 3.92 (2), Glx 1.29 (1), Gly 1.10 (1), Lys 0.96 (1), Phe 0.95 (1), Thr 0.71 (1), Trp 2.57 (2).

FAB/MS: $MH^+$=1295.0

EXAMPLE CVI

D-Arg-cyclo(D-Lys-cyclo(D-Cys-Gly-Phe-D-Cys)-D-Trp-D-Glu]-D-Trp-D-Val-$NH_2$ (Preferred Peptide (106))

The N-protected (Boc) peptide was prepared on an ABI Model 431A Peptide Synthesizer using Version 1.12 of the standard BOC software. 4-methyl benzhydrylamine resin (0.47, 0.5 mmol) was used in the synthesis. Boc-D-Lys (Fmoc) (Lot ZG864), Boc-D-Glu(OFm) (Lot ZJ 302) and Boc-D-Cys(Acm) (Lot ZJ 348) were purchased from Bachem, California. The find weight of the resin was 1.3 g.

The Boc-D-Arg(Tos)-D-Lys(Fmoc)-D-Cys(Acm)-Gly-Phe-D-Cys(Acm)-D-Trp-D-Glu(OFm)-D-Trp-D-Val-resin (1.3 g) was transferred into a manual shaker then treated with 20% piperidine/DMF solution (1×2 min and 1×20 min), followed by overnight coupling (20 hrs) with BOP reagent (2 mmol), HOBt (4 mmol) in NMP with DIEA (6 mmol). The protected peptidyl resin was treated with TFA/DCM (1:1, v/v) for 5 min and 25 min, washed with several solvents and dried. (Yield: 1.23 g).

The peptide was cleaved from the resin (1.2 g) using 12 mL of HF and 1.2 mL of anisole for 60 min at 0° C. The resin was washed with ether and the peptide extracted with TFA/DCM (1:1, v/v) (3×15 mL) to give 710 mg of crude peptide. The crude peptide (700 mg) was dissolved in 60 mL of 50% AcOH and purified on a Vydac C-18 column (15μ, 10×30 cm) eluting with a 20–60% gradient of 80% ethanol in 0.1% TFA over 60 min at a flow rate of 120 mL/min. Semipure functions were pooled, evaporated to approx. 100 mL and lyophilized to give 141 mg of white solid.

The Acm groups containing peptide (100 mg, 0.07 mmol) (Formula $C_{67}H_{93}N_{19}O_{13}S_2$, M.W. 1436.7) was dissolved in 5 mL of 30% AcOH and stirred with mercuric acetate (89 mg, 0.28 mmol) over 80 min at room temperature. Dithiothreitol (DTT) (216 mg, 1.4 mmol) was added and stirring was continued for 120 min, followed by filtration through a Celite layer and 0.2μ filter. The solution of peptide was loaded onto a Vydac C-18 column, 15μ, 5×25 cm, eluting with 20–80% gradient of 80% acetonitrile in 0.1% TFA over 120 min at a flow rate of 15 mL/min. Semipure fractions were pooled and lyophilized to give 68 mg of white solid. The product (68 mg) was dissolved in 50 mL of 40% AcOH and then added dropwise to the mixture of water (800 mL), $NH_4OH$ (to keep pH approx. 7.5) and 0.01M $K_3Fe(CN)_6$ (approx. 3 mL). After each addition of the linear precursor to the reaction mixture (approx. 1.5 mL) its pH was adjusted to 7.5 by addition of $NH_4OH$ followed by addition of $K_3Fe(CN)_6$ solution. The total volume of the 0.01M $K_3Fe(CN)_6$ solution used for oxidation was 8 mL. The 2 mL of $K_3Fe(CN)_6$ solution was added extra and the mixture was stirred over 20 min (pH=7.5), then the pH was adjusted to 4–5 by addition of AcOH followed by stirring with 5 g of anion exchange AG 3-X4, 200–400 mesh, free base form (Bio-Rad) over 30 min. The resin was filtered off, washed with 5% acetic acid (3×100 mL) and combined fractions were lyophilized to give 600 mg of semi-dry solid.

The crude peptide (600 mg) was purified on a Vydac C-18 column (15μ, 5×25 cm) eluting with a 25–65% gradient of 80% acetonitrile in 0.1% TFA over 120 min at a flow rate of 15 mL per min. Fractions were collected, analyzed by HPLC and pure fractions pooled and lyophilized to give 10 mg of white solid.

Amino acid analysis: Arg 1.00 (1), Cys 0.49 (2), Glx 1.14 (1), Gly 1.03 (1), Lys 0.97 (1), Phe 0.99 (1), Trp 1.69 (2), VaL 1.00 (1).

FAB/MS: $MH^+$ 1293.4

EXAMPLE CVII

D-Arg-D-Lys-D-Ile-Gly-cyclo(D-Cys-D-Ile-D-Trp-D-Cys)-D-Trp-D-Val-$NH_2$ (Preferred Peptide (107))

The peptide was prepared on an ABI Model 431A Peptide Synthesizer using Version 1.12 of the standard BOC software. 4-methyl benzhydrylamine resin (0.625 g, 0.5 mmol) was used in the synthesis. The final weight of the resin was 1.3 g.

The peptide was cleaved from the resin (1.3 g) using 13 mL of HF and 1.3 mL of anisole for 60 min at 0° C. The resin was washed with ether and the peptide extracted with TFA/DCM (1:1, v/v) (3×15 mL) to give 650 mg of crude peptide. The crude linear peptide (650 mg) was dissolved in 140 mL of 85% AcCH and then added dropwise to the mixture of water (1200 mL), $NH_4OH$ (to keep pH approx. 7.5) and 0.01M $K_3Fe(CN)_6$ (approx. 3 mL). After each addition of the linear precursor to the reaction mixture (approx. 1.5 mL) its pH was adjusted to 7.5 by addition of NH$_4$OH followed by addition of K$_3$Fe(CN)$_6$ solution. The total volume of the 0.01M K$_3$Fe(CN)$_6$ solution used for oxidation was 47 mL. The 2 mL of K$_3$Fe(CN)$_6$ solution was added extra and the mixture was stirred over 20 min (pH=7.5), then the pH was adjusted to 4–5 by addition of AcOH followed by stirring with 5 g of anion exchange AG 3-X4, 200–400 mesh, free base form (Bio-Rad) over 30 min. The resin was filtered off, washed with 5% acetic acid (3×100 mL) and combined fractions (2000 mL) were loaded onto a Vydac C-18 column (15µ, 10×30 cm) eluting with a 0–30% over 5 min. and 30–60% gradient of 80% ethanol in 0.1% TFA over 55 min at a flow rate of 120 mL per min. Fractions were collected, analyzed by HPLC and pure fractions pooled and lyophilized to give 15 mg of white solid.

Amino acid analysis: Arg 1.02 (1), Cys 1.39 (2), Gly 1.26 (1), Ile 1.73 (2), Lys 0.99 (1), Trp 1.78 (2), Val 1.01 (1).

EXAMPLE CVIII

D-Arg-D-Lys-D-Ile-Gly-cyclo-(D-Cys-D-Ile-D-Trp-D-Cys)-D-Thr-D-Val-NH$_2$ (Preferred Peptide (108))

The peptide was prepared on an ABI Model 431A Peptide Synthesizer using Version 1.12 of the standard BOC software. 4-methyl benzhydrylamine resin (0.625 g, 0.5 mmol) was used in the synthesis. The final weight of the resin was 1.5 g.

The peptide was cleaved from the resin (1.5 g) using 15 mL of HF and 1.5 mL of anisole for 60 min at 0° C. The resin was washed with ether and the peptide extracted with TFA/DCM (1:1, v/v) (3×15 mL) to give 650 mg of crude peptide. The crude linear peptide (630 mg) was dissolved in 40 mL of 70% AcOH and then added dropwise to the mixture of water (1200 mL), NH$_4$OH (to keep pH approx. 7.5) and 0.01M K$_3$Fe(CN)$_6$ (approx. 3 mL). After each addition of the linear precursor to the reaction mixture (approx. 1.5 mL) its pH was adjusted to 7.5 by addition of NH$_4$OH followed by addition of K$_3$Fe(CN)$_6$ solution. The total volume of the 0.01M K$_3$Fe(CN)$_6$ solution used for oxidation was 68 mL. An additional 2 mL of K$_3$Fe(CN)$_6$ solution was added and the mixture was stirred over 30 min (pH=7.5). Next, the pH was adjusted to 4–5 with the addition of acetic acid, followed by stirring with 5 g of anion exchange resin AG 3-X4, 200–400 mesh, free base form (Bio-Rad) over 30 min. The resin was filtered, washed with 5% acetic acid (3×100 mL), and the combined fractions were lyophilized to give 1.8 g of white solid.

The crude peptide (1.8 g) was purified on a Vydac C-18 column (15µ, 10×30 cm) eluting with a 0–20% over 10 min and a 20–55% gradient of 80% acetonitrile in 0.1% TFA over 50 min at a flow rate of 120 mL per min. Fractions were collected, analyzed by HPLC and pure fractions pooled and lyophilized to give 195 mg of white solid.

Amino acid analysis: Arg 1.01 (1), Cys (O$_3$H), 1.28 (2), Gly 1.06 (1), Ile 2.78 (2), Lys 1.04 (1), Thr 0.80 (1), Trp 0.00 (1), Val 0.99 (1).

FAB/MS: MH$^+$ 1175.5

EXAMPLE CIX cyclo(D-Cys-D-Lys-D-Ile-D-Cys)-Gly-D-Ile-D-Trp-D-Thr-D-Trp-D-Val-NH$_2$ (Preferred Peptide (109))

The peptide was prepared on an ABI Model 431A Peptide Synthesizer using Version 1.12 of the standard BOC software. 4-methyl benzhydrylamine resin (0.4 g, 0.5 mmol) was used in the synthesis. The final weight of the resin was 1.27 g.

The peptide was cleaved from the resin (1.2 g) using 12 mL of HF and 1.2 mL of anisole for 60 min at 0° C. The resin was washed with ether and the peptide extracted with TFA/DCM (1:1, v/v) (3×15 mL) to give 704 mg of crude peptide.

The crude linear peptide (350 mg) was dissolved in 150 mL of 80% AcOH and 60 mL of DMF then added dropwise to the mixture of water (1200 mL), NH$_4$OH (to keep pH approx. 7.5) and 0.01M K$_3$Fe(CN)$_6$ (approx. 3 mL). After each addition of the linear precursor to the reaction mixture (approx. 1.5 mL) its pH was adjusted to 7.5 by addition of NH$_4$OH followed by addition of K$_3$Fe(CN)$_6$ solution. The total volume of the 0.01M K$_3$Fe(CN)$_6$ solution used for oxidation was 42 mL. The 2 mL of K$_3$Fe(CN)$_6$ solution was added extra and the mixture was stirred over 20 min (pH=7.5), then the pH was adjusted to 4–5 by addition of AcOH followed by stirring with 5 g of anion exchange AG 3-X4, 200–400 mesh, free base form (Bio-Rad) over 30 min. The resin was filtered off, washed with 25% acetic acid (1×100 mL) and combined fractions (approx. 1800 mL) were loaded onto a Vydac C-18 column (15µ, 10×30 cm) eluting with a 30–70% gradient of 80% ethanol in 0.1% TFA over 120 min at a flow rate of 60 mL per min. Fractions were collected, analyzed by HPLC and pure fractions pooled and lyophilized to give 15.5 mg of white solid.

Amino acid analysis: Cys 14.95 (2), Gly 1.15 (1), Ile 1.75 (2), Lys 1.04 (1), Thr 0.78 (1), Trp 1.63 (2), Val 1.07 (1).

FAB-MS MH$^+$ 1206.8

EXAMPLE CHANGE NO. XXXIV

Inhibition of Neutrophil influx in a rat model of thioglycolate-induced peritonitis CD-1 rats (175–200 g) were injected i.p. with 10 ml thioglycollate medium (BBL #21195/21196 lot#H1KBGP). At −5 minutes, 1.5 hours, and 3.5 hours post thioglycollate injection 5 rats were injected with D-arginyl-D-lysyl-cyclo(D-cysteinyl-glycyl-phenylalanyl-D-cysteinyl)-D-tryptophyl-D-threonyl-D-tryptophyl-D-valineamide (Preferred peptide (19)) (0.75 mls at −5, 0.25 mls at 1.5 and 0.25 mls at 3.5). 5 rats were injected with vehicle at the same time points (0.75 mls at −5, 0.50 mls at 1.5, and 0.25 mls at 3.5). 5 rats received thioglycollate only and served as controls. At 4 hours post thioglycollate injection all animals were sacrificed by CO$_2$ asphyxiation. Neutrophils were harvested by flushing the peritoneal cavity with 50 mls of Hanks balanced salt solution w/o Ca and Mg (JHR Biosciences 55-02178P Lot# IL3697) containing 0.3% ultrapure EDTA (JT Baker 4040-01 lot# D42704). White cells were then counted using the Danam Vet 8 cell counter. The peptide treated rats showed a 67% decrease in neutrophil influx in response to thioglycolate stimulation (FIG. III).

TABLE I

| STRUCTURE | Preferred Peptide | % INHIBITION - IC$_{50}$ (mM) |
|---|---|---|
| RK-cyclo(CGGC)-WTW-NH$_2$ | (7) (SEQ ID NO: 10) | 0.610 |
| rk-cyclo(cGGc)-wtw-NH$_2$ | (8) | 0.097 |
| RK-cyclo(CGGC)-WTWV-NH$_2$ | (9) (SEQ ID | 0.003 |

TABLE I-continued

| STRUCTURE | Preferred Peptide | % INHIBITION - IC$_{50}$ (mM) |
|---|---|---|
| RKI-cyclo(EGIWK)-WV-NH$_2$ | (30) (SEQ ID NO: 11) | 0.093 |
| cyclo(CKIGGIWTWC)-NH$_2$ | (3) (SEQ ID NO: 17) | 0.131 |
| R-cyclo(CIGGC)-WTWV-NH$_2$ | (5) (SEQ ID NO: 7) | 0.036 |
| RK-cyclo(CGG-Pen)-WTWV-NH$_2$ | (10) (SEQ ID NO: 8) | 0.030 |
| RKIGG-cyclo(CWTWC)-NH$_2$ | (33) (SEQ ID NO: 12) | 0.468 |
| rk-cyclo(caFc)-wtwv-NH$_2$ | (11) | 0.007 |
| rk-cyclo(cfGc)-wtwv-NH$_2$ | (12) | 0.048 |
| rk-cyclo(cGfc)-wtwv-NH$_2$ | (13) | 0.050 |
| rk-cyclo(cGGc)-ftwv-NH$_2$ | (14) | 0.040 |
| rk-cyclo(cpGc)-wtwv-NH$_2$ | (15) | 0.485 |
| rk-cyclo(cGpc)-wtwv-NH$_2$ | (16) | 0.001 |
| rk-cyclo(cGGc)-wtqwv-NH$_2$ | (17) | 0.225 |
| rk-cyclo(cFGc)-wtwv-NH$_2$ | (18) | 0.049 |
| rk-cyclo(cGFc)-wtwv-NH$_2$ | (19) | 0.006 |
| rk-cyclo(cGPc)-wtwv-NH$_2$ | (20) | 0.174 |
| rkiGcyclo(ciwc)-tv-NH$_2$ | (32) | 0.023 |
| r-cyclo(ciGc)-iwtwv-NH$_2$ | (4) | 0.041 |
| rk-cyclo(c-Ava-c)-wtwv-NH$_2$ | (21) | 0.023 |
| cyclo(EKIGGK)-WTWV-NH$_2$ | (1) (SEQ ID NO: 5) | 0.115 |
| RK-cyclo(Dap-GGD)-WTWV-NH$_2$ | (22) (SEQ ID NO: 4) | 0.013 |
| cyclo(KKIGGE)-WTWV-NH$_2$ | (2) (SEQ ID NO: 6) | 0.069 |
| RKI-cyclo(KGIWE)-WV-NH$_2$ | (31) (SEQ ID NO: 18) | 0.018 |
| RK-cyclo(Pen-GGC)-WTWV-NH$_2$ | (23) (SEQ ID NO: 13) | 0.036 |
| RK-cyclo(Pen-GG-Pen)-WTWV-NH$_2$ | (24) (SEQ ID NO: 14) | 0.041 |
| rk-cyclo(cGGc)wtwv-NH$_2$ | (25) | 0.017 |
| cyclo(CRGGC)-WTWV-NH$_2$ | (6) (SEQ ID NO: 9) | 0.054 |
| K-cyclo(CGGC)-WTWV-NH$_2$ | (27) (SEQ ID NO: 15) | 0.022 |
| k-cyclo(cGGc)-wtwv-NH$_2$ | (26) | 0.026 |
| cyclo(CGGC)-WTWV-NH$_2$ | (29) (SEQ ID NO: 16) | 0.325 |
| cyclo(cGGc)-wtwv-NH$_2$ | (28) | 0.311 |
| ra-cyclo(cGFc)-wtwv-NH$_2$ | (110) | 0.0529 |
| rK-cyclo(cCFc)-wtwv-NH$_2$ | (34) | 0.0885 |
| rq-cyclo(cGFc)-wtwv-NH$_2$ | (111) | 0.0184 |
| re-cyclo(cGFc)-wtwv-NH$_2$ | (112) | 0.2365 |
| rk-cyclo(CGFc)-wtwv-NH$_2$ | (35) | 0.0116 |
| rk-cyclo-(CGGC)-wtwv-NH$_2$ | (113) | 0.0007 |
| rk-cyclo(cG-[3,4-dehydro-L-Pro]-c)-wtwv-NH$_2$ | (36) | 0.2666 |
| rk-cyclo(cAFc)-wtwv-NH$_2$ | (37) | 0.2046 |
| rk-cyclo(cGAc)-wtwv-NH$_2$ | (38) | 0.0750 |
| rk-cyclo(cRFc)-wtwv-NH$_2$ | (39) | 0.0306 |
| rk-cyclo(cGRc)-wtwv-NH$_2$ | (40) | 0.3240 |
| rk-cyclo(cGNc)-wtwv-NH$_2$ | (41) | 0.0262 |
| rk-cyclo(cGDc)-wtwv-NH$_2$ | (42) | 0.9441 |
| rk-cyclo(c-beta-Ala-Fc)-wtwv-NH$_2$ | (43) | 0.0175 |
| rk-cyclo(caFc)-wtwv-NH$_2$ | (44) | 0.0070 |
| rk-cyclo(crFc)-wtwv-NH$_2$ | (45) | 0.2631 |
| rk-cyclo(cqQc)-wtwv-NH$_2$ | (114) | 0.0121 |
| rk-cyclo(cGFc)-qtwv-NH$_2$ | (46) | 0.0484 |
| rk-cyclo(chFc)-wtwv-NH$_2$ | (47) | 0.0070 |
| rk-cyclo(cGFc)-htwv-NH$_2$ | (48) | 0.4060 |
| rk-cyclo(cIIc)-wtwv-NH$_2$ | (49) | 0.0071 |
| rk-cyclo(cGFc)-(D-Ac-K)-twv-NH$_2$ | (50) | 0.0195 |
| rk-cyclo(cGFc)-(D-Nal)-twv-NH$_2$ | (51) | 0.0077 |
| rk-cyclo(cGic)-wtwv-NH$_2$ | (52) | 0.0103 |
| rk-cyclo(cGLc)-wtwv-NH$_2$ | (53) | 0.0187 |
| rk-cyclo(ckFc)-wtwv-NH$_2$ | (54) | 0.2175 |
| rk-cyclo(cGkc)-wtwv-NH$_2$ | (55) | 0.0597 |
| rk-cyclo(cGFc)-ktwv-NH$_2$ | (56) | 0.7270 |
| rk-cyclo(cG-(p-Cl-F)-c)-wtwv-NH$_2$ | (115) | 0.0015 |
| rk-cyclo(cpFc)-wtwv-NH$_2$ | (57) | 0.0704 |
| rk-cyclo(cG-[D-thioproline]-c)-wtwv-NH$_2$ | (58) | 0.1858 |
| rk-cyclo(cG-[D-Tic]-c)-wtwv-NH$_2$ | (59) | 0.0183 |
| rk-cyclo(cGWc)-wtwv-NH$_2$ | (60) | 0.0014 |
| rk-cyclo(cGFc)-wthv-NH$_2$ | (61) | 0.0654 |
| rk-cyclo(cGFc)-wtkv-NH$_2$ | (62) | 0.5334 |
| rk-cyclo(cGFc)-wtyv-NH$_2$ | (63) | 0.0193 |
| rk-cyclo(cGFc)-ytwv-NH$_2$ | (64) | 0.0462 |
| rk-cyclo(cGFc)-ytwv-NH$_2$ | (65) | 0.0462 |
| rk-cyclo(cGvc)-wtwv-NH$_2$ | (116) | 0.0046 |
| rk-cyclo(cGQc)-wtwv-NH$_2$ | (65) | 0.0783 |
| rk-cyclo(cGEc)-wtwv-NH$_2$ | (66) | 0.2873 |
| rk-cyclo(cIic)-wtwv-NH$_2$ | (67) | 0.0111 |
| rk-cyclo(cGIc)-wtwv-NH$_2$ | (68) | 0.0037 |
| rk-cyclo(cGLc)-wtwv-NH$_2$ | (69) | 0.1465 |
| rk-cyclo(cKFc)-wtwv-NH$_2$ | (70) | 0.0859 |
| rk-cyclo(cGKc)-wtwv-NH$_2$ | (71) | 1.9967 |
| rk-cyclo(cG-[N-Me-Phe]-c)-wtwv-NH$_2$ | (72) | 0.0377 |
| rk-cyclo(cG-Nal-c)-wtwv-NH$_2$ | (73) | 0.0032 |
| rk-cyclo(cFGc)-wtwv-NH$_2$ | (74) | 0.0491 |
| rk-cyclo(cGFc)-Vwtw-NH$_2$ | (75) | 0.0060 |
| rk-cyclo(cGFc)-ptwv-NH$_2$ | (76) | 0.1052 |
| rk-cyclo(cGFc)-wtpv-NH$_2$ | (77) | 2.2698 |
| rk-cyclo(cGFc)-wt-(D-Nal)-v-NH$_2$ | (78) | 0.0507 |
| rk-cyclo(cGFc)-wtfv-NH$_2$ | (79) | 0.0077 |
| rk-cyclo(cGFc)-wtpv-NH$_2$ | (80) | 0.6825 |
| rk-cyclo-desthio(cGFc)-wtwv-NH$_2$ | (81) | 0.0106 |
| rk-cyclo(cGFc)-Ptwv-NH$_2$ | (82) | 0.5470 |
| rk-cyclo(cPGc)-wtwv-NH$_2$ | (83) | 0.9831 |
| rk-cyclo(cPFc)-wtwv-NH$_2$ | (84) | 0.0264 |
| rk-cyclo(cGPc)-wtwv-NH$_2$ | (85) | 0.2004 |
| rk-cyclo(cG-Tic-c)-wtwv-NH$_2$ | (86) | 0.0834 |
| rk-cyclo(cGYc)-wtwv-NH$_2$ | (87) | 0.0057 |
| rk-cyclo-desthio(cGYc)-wtwv-NH$_2$ | (88) | 0.1119 |
| rk-cyclo(cGVc)-wtwv-NH$_2$ | (89) | 0.0223 |
| rk(cyclo(cGFc)-wtrv-NH$_2$ | (90) | 0.0099 |
| rk-cyclo(cGFC)-wtwv-NH$_2$ | (91) | 0.0427 |
| rk-cyclo(cilc)-wtwv-NH$_2$ | (92) | 0.0024 |
| rk-cyclo(ciFc)-wtwv-NH$_2$ | (93) | 0.0675 |
| rk-cyclo(cHFc)-wtwv-NH$_2$ | (94) | 0.0022 |
| rk-cyclo(cIPc)-wtwv-NH$_2$ | (95) | 0.0268 |
| rk-cyclo(cGFc)-wtWv-NH$_2$ | (96) | 0.0267 |
| rk-cyclo(cGFc)-wtwv-NH$_2$ | (97) | 0.0009 |
| rk-cyclo(cGFc)-wTwv-NH$_2$ | (98) | 0.0287 |
| rk-cyclo(cGFc)-Wtwv-NH$_2$ | (99) | 0.0031 |
| rk-cyclo(cGFc)-ytqv-NH$_2$ | (100) | 0.0883 |
| dk-cyclo(cGFc)-wtwv-NH$_2$ | (117) | 0.2377 |
| Rk-cyclo(cGFc)-wtwv-NH$_2$ | (101) | 0.0339 |
| rk-cyclo(cGFc)-wtwq-NH-Bu | (102) | 0.0080 |
| rk-cyclo(cGFc)-wvwv | (103) | 0.0427 |
| Ac-k-cyclo(cGYc)-wtwv-NH$_2$ | (104) | 0.1911 |
| r-cyclo[k-cyclo(cGFc)-wtwe]-NH$_2$ | (105) | 0.0978 |
| r-cyclo(k-cyclo[cGFc]-we)-wv-NH$_2$ | (106) | 0.0080 |
| rkiG-cyclo(ciwc)-wv-NH$_2$ | (107) | 0.0080 |
| rkiG-cyclo(ciwc)-tv-NH$_2$ | (108) | 0.0238 |
| cyclo(ckic)-Giwtwv-NH$_2$ | (109) | 0.0339 |

What is claimed:

1. A peptide selected from the group comprising:

| | | |
|---|---|---|
| (7) | (SEQ ID NO:10) | Arg—Lys-cyclo(Cys—Gly—Gly—Cys)—Trp—Thr—Trp—NH₂; |
| (8) | | D-Arg-D-Lys-cyclo(D-Cys—Gly—Gly-D-Cys)-D-Trp-D-Thr-D-Trp—NH₂; |
| (9) | (SEQ ID NO:11) | Arg—Lys-cyclo(Cys—Gly—Gly—Cys)—Trp—Thr—Trp—Val—NH₂; |
| (10) | (SEQ ID NO:12) | Arg—Lys-cyclo(Cys—Gly—Gly—Pen)—Trp—Thr—Trp—Val—NH₂; |
| (11) | | D-Arg-D-Lys-cyclo(D-Cys-D-Ala—Phe-D-Cys)-D-Trp-D-Thr-D-Trp-D-Val—NH₂; |
| (12) | | D-Arg-D-Lys-cyclo(D-Cys-D-Phe—Gly-D-Cys)-D-Trp-D-Thr-D-Trp-D-Val—NH₂; |
| (13) | | D-Arg-D-Lys-cyclo(D-Cys—Gly-D-Phe-D-Cys)-D-Trp-D-Thr-D-Trp-D-Val—NH₂; |
| (14) | | D-Arg-D-Lys-cyclo(D-Cys—Gly—Gly-D-Cys)-D-Phe-D-Thr-D-Trp-D-Val—NH₂; |
| (15) | | D-Arg-D-Lys-cyclo(D-Cys—Gly-D-Pro-Gly-D-Lys)-D-Trp-D-Thr-D-Trp-D-Val—NH₂; |
| (16) | | D-Arg-D-Lys-cyclo(D-Cys—Gly-D-Pro-D-Cys)-D-Trp-D-Thr-D-Trp-D-Val—NH₂; |
| (17) | | D-Arg-D-Lys-cyclo(D-Cys—Gly—Gly-D-Cys)-D-Trp-D-Thr-D-Gln-D-Trp-D-Val—NH₂; |
| (18) | | D-Arg-D-Lys-cyclo(D-Cys—Phe—Gly-D-Cys)-D-Trp-D-Thr-D-Trp-D-Val—NH₂; |
| (19) | | D-Arg-D-Lys-cyclo(D-Cys—Gly—Phe-D-Cys)-D-Trp-D-Thr-D-Trp-D-Val—NH₂; |
| (20) | | D-Arg-D-Lys-cyclo(D-Cys—Gly—Pro-D-Cys)-D-Trp-D-Thr-D-Trp-D-Val—NH₂; |
| (21) | | D-Arg-D-Lys-cyclo(D-Cys—Ava-D-Cys)-D-Trp-D-Thr-D-Trp-D-Val—NH₂; |
| (22) | (SEQ ID NO:4) | Arg—Lys-cyclo(Dap—Gly—Gly—Asp)—Trp—Thr—Trp—Val—NH₂; |
| (23) | (SEQ ID NO:13) | Arg—Lys-cyclo(Pen—Gly—Gly—Cys)—Trp—Thr—Trp—Val—NH₂; |
| (24) | (SEQ ID NO:14) | Arg—Lys-cyclo(Pen—Gly—Gly—Pen)—Trp—Thr—Trp—Val—NH₂; |
| (25) | | D-Arg-D-Lys-cyclo(D-Cys—Gly—Gly-D-Cys)-D-Trp-D-Thr-D-Trp-D-Val—NH₂; |
| (26) | | D-Lys-cyclo(D-Cys—Gly—Gly-D-Cys)-D-Trp-D-Thr-D-Trp-D-Val—NH₂; |
| (27) | (SEQ ID NO:15) | Lys-cyclo(Cys—Gly—Gly—Cys)—Trp—Thr—Trp—Val—NH₂; |
| (28) | | Cyclo(D-Cys—Gly—Gly-D-Cys)-D-Trp-D-Thr-D-Trp-D-Val—NH₂; |
| (34) | | D-Arg—Lys-cyclo(D-Cys—Gly—Phe-D-Cys)-D-Trp-D-Thr-D-Trp-D-Val—NH₂ |
| (35) | | D-Arg-D-Lys-cyclo(Cys—Gly—Phe-D-Cys)-D-Trp-D-Thr-D-Trp-D-Val—NH₂ |
| (36) | | D-Arg-D-Lys-cyclo(D-Cys—Gly-(3,4-dehydro-D-Pro)-D-Cys)-D-Trp-D-Thr-D-Trp-D-Val—NH₂ |
| (37) | | D-Arg-D-Lys-cyclo(D-Cys—Ala—Phe-D-Cys)-D-Trp-D-Thr-D-Trp-D-Val—NH₂ |
| (38) | | D-Arg-D-Lys-cyclo(D-Cys—Gly—Ala-D-Cys)-D-Trp-D-Thr-D-Trp-D-Val—NH₂ |
| (39) | | D-Arg-D-Lys-cyclo(D-Cys—Arg—Phe-D-Cys)-D-Trp-D-Thr-D-Trp-D-Val—NH₂ |
| (40) | | D-Arg-D-Lys-cyclo(D-Cys—Gly—Arg-D-Cys)-D-Trp-D-Thr-D-Trp-D-Val—NH₂ |
| (41) | | D-Arg-D-Lys-cyclo(D-Cys—Gly—Asn-D-Cys)-D-Trp-D-Thr-D-Trp-D-Val—NH₂ |
| (42) | | D-Arg-D-Lys-cyclo(D-Cys—Gly—Asp-D-Cys)-D-Trp-D-Thr-D-Trp-D-Val—NH₂ |
| (43) | | D-Arg-D-Lys-cyclo(D-Cys-Beta-Ala—Phe-D-Cys)-D-Trp-D-Thr-D-Trp-D-Val—NH₂ |
| (44) | | D-Arg-D-Lys-Cyclo(D-Cys-D-Ala—Phe-D-Cys)-D-Trp-D-Thr-D-Trp-D-Val—NH₂ |
| (45) | | D-Arg-D-Lys-cyclo(D-Cys-D-Arg—Phe-D-Cys)-D-Trp-D-Thr-D-Trp-D-Val—NH₂ |
| (46) | | D-Arg-D-Lys-cyclo(D-Cys—Gly—Phe-D-Cys)-D-Gln-D-Thr-D-Trp-D-Val—NH₂ |
| (47) | | D-Arg-D-Lys-cyclo(D-Cys-D-His—Phe-D-Cys)-D-Trp-D-Thr-D-Trp-D-Val—NH₂ |
| (48) | | D-Arg-D-Lys-cyclo(D-Cys—Gly—Phe-D-Cys)-D-His-D-Thr-D-Trp-D-Val—NH₂ |
| (49) | | D-Arg-D-Lys-cyclo(D-Cys—Ile—Ile-D-Cys)-D-Trp-D-Thr-D-Trp-D-Val—NH₂ |
| (50) | | D-Arg-D-Lys-cyclo-desthio(D-Cys—Gly—Phe-D-Cys)(D-Acetyl Lys)-D-Thr-D-Trp-D-Val—NH₂ |
| (51) | | D-Arg-D-Lys-cyclo(D-Cys—Gly—Phe-D-Cys)-D-Nal-D-Thr-D-Val—NH₂ |
| (52) | | D-Arg-D-Lys-cyclo(D-Cys—Gly-D-Ile-D-Cys)-D-Trp-D-Thr-D-Trp-D-Val—NH₂ |
| (53) | | D-Arg-D-Lys-cyclo(D-Cys—Gly-D-Leu-D-Cys)-D-Trp-D-Thr-D-Trp-D-Val—NH₂ |
| (54) | | D-Arg-D-Lys-cyclo(D-Cys-D-Lys—Phe-D-Cys)-D-Trp-D-Thr-D-Trp-D-Val—NH₂ |
| (55) | | D-Arg-D-Lys-cyclo(D-Cys—Gly-D-Lys-D-Cys)-D-Trp-D-Thr-D-Trp-D-Val—NH₂ |
| (56) | | D-Arg-D-Lys-cyclo(D-Cys—Gly—Phe-D-Cys)-D-Lys-D-Thr-D-Trp-D-Val—NH₂ |
| (57) | | D-Arg-D-Lys-cyclo(D-Cys-D-Pro—Phe-D-Cys)-D-Trp-D-Thr-D-Trp-D-Val—NH₂ |
| (58) | | D-Arg-D-Lys-cyclo(D-Cys—Gly-D-Tpro-D-Cys)-D-Trp-D-Thr-D-Trp-D-Val—NH₂ |
| (59) | | D-Arg-D-Lys-cyclo(D-Cys—Gly-D-Tic-D-Cys)-D-Trp-D-Thr-D-Trp-D-Val—NH₂ |
| (60) | | D-Arg-D-Lys-cyclo(D-Cys—Gly—Trp-D-Cys)-D-Trp-D-Thr-D-Trp-D-Val—NH₂ |
| (61) | | D-Arg-D-Lys-cyclo(D-Cys—Gly—Phe-D-Cys)-D-Trp-D-Thr-D-His-D-Val—NH₂ |
| (62) | | D-Arg-D-Lys-cyclo(D-Cys-Gly—Phe-D-Cys)-D-Trp-D-Thr-D-Lys-D-Val—NH₂ |
| (63) | | D-Arg-D-Lys-cyclo(D-Cys—Gly—Phe-D-Cys)-D-Trp-D-Thr-D-Tyr-D-Val—NH₂ |
| (64) | | D-Arg-D-Lys-cyclo(D-Cys—Gly—Phe-D-Cys)-D-Tyr-D-Thr-D-Trp-D-Val—NH₂ |
| (65) | | D-Arg-D-Lys-cyclo(D-Cys—Gly—Gln-D-Cys)-D-Trp-D-Thr-D-Trp-D-Val—NH₂ |
| (66) | | D-Arg-D-Lys-cyclo(D-Cys—Gly—Glu-D-Cys)-D-Trp-D-Thr-D-Trp-D-Val—NH₂ |
| (67) | | D-Arg-D-Lys-cyclo(D-Cys—Ile-D-Ile-D-Cys)-D-Trp-D-Thr-D-Trp-D-Val—NH₂ |
| (68) | | D-Arg-D-Lys-cyclo(D-Cys—Gly—Ile-D-Cys)-D-Trp-D-Thr-D-Trp-D-Val—NH₂ |
| (69) | | D-Arg-D-Lys-cyclo(D-Cys—Gly—Leu-D-Cys)-D-Trp-D-Thr-D-Trp-D-Val—NH₂ |
| (70) | | D-Arg-D-Lys-cyclo(D-Cys—Lys—Phe-D-Cys)-D-Trp-D-Thr-D-Trp-D-Val—NH₂ |
| (71) | | D-Arg-D-Lys-cyclo(D-Cys—Gly—Lys-D-Cys)-D-Trp-D-Thr-D-Trp-D-Val—NH₂ |
| (72) | | D-Arg-D-Lys-cyclo(D-Cys—Gly—[N-Methyl—Phe]-D-Cys)-D-Trp-D-Thr-D-Trp-D-Val—NH₂ |
| (73) | | D-Arg-D-Lys-cyclo(D-Cys—Gly—Nal-D-Cys)-D-Trp-D-Thr-D-Trp-D-Val—NH₂ |
| (74) | | D-Arg-D-Lys-cyclo-(D-Cys—Phe—Gly-D-Cys)-D-Trp-D-Thr-D-Trp-D-Val—NH₂ |
| (75) | | D-Arg-D-Lys-cyclo(D-Cys—Gly—Phe-D-Cys)—Val-D-Trp-D-Thr-D-Trp—NH₂ |
| (76) | | D-Arg-D-Lys-cyclo(D-Cys—Gly—Phe-D-Cys)-D-Pro-D-Thr-D-Trp-D-Val—NH₂ |
| (77) | | D-Arg-D-Lys-cyclo(D-Cys—Gly—Phe-D-Cys)-D-Trp-D-Thr-D-Pro-D-Val—NH₂ |
| (78) | | D-Arg-D-Lys-cyclo-desthio(D-Cys—Gly—Phe-D-Cys)-D-Trp-D-Thr-D-Nal-D-Val—NH₂ |
| (79) | | D-Arg-D-Lys-cyclo(D-Cys—Gly—Phe-D-Cys)-D-Trp-D-Thr-D-Phe-D-Val—NH₂ |
| (80) | | D-Arg-D-Lys-cyclo(D-Cys—Gly—Phe-D- |

| | |
|---|---|
| | Cys)—Trp-D-Thr—Pro-D-Val—NH$_2$ |
| (81) | D-Arg-D-Lys-cyclo-desthio(D-Cys—Gly—Phe-D-Cys)-D-Trp-D-Thr-D-Trp-D-Val—NH$_2$ |
| (82) | D-Arg-D-Lys-cyclo(D-Cys—Gly—Phe-D-Cys)—Pro-D-Thr-D-Trp-D-Val—NH$_2$ |
| (83) | D-Arg-D-Lys-cyclo(D-Cys—Pro—Gly-D-Cys)-D-Trp-D-Thr-D-Trp-D-Val—NH$_2$ |
| (84) | D-Arg-D-Lys-cyclo(D-Cys—Pro—Phe-D-Cys)-D-Trp-D-Thr-D-Trp-D-Val—NH$_2$ |
| (85) | D-Arg-D-Lys-cyclo(D-Cys—Gly—Pro-D-Cys)-D-Trp-D-Thr-D-Trp-D-Val—NH$_2$ |
| (86) | D-Arg-D-Lys-cyclo(D-Cys—Gly—Tic-D-Cys)-D-Trp-D-Thr-D-Trp-D-Val—NH$_2$ |
| (87) | D-Arg-D-Lys-cyclo(D-Cys—Gly—Tyr-D-Cys)-D-Trp-D-Thr-D-Trp-D-Val—NH$_2$ |
| (88) | D-Arg-D-Lys-cyclo-desthio(D-Cys—Gly—Tyr-D-Cys)-D-Trp-D-Thr-D-Trp-D-Val—NH$_2$ |
| (89) | D-Arg-D-Lys-cyclo(D-Cys—Gly—Val-D-Cys)-D-Trp-D-Thr-D-Trp-D-Val—NH$_2$ |
| (90) | D-Arg-D-Lys-cyclo(D-Cys—Gly—Phe-D-Cys)-D-Trp-D-Thr-D-Arg-D-Val—NH$_2$ |
| (91) | D-Arg-D-Lys-cyclo(D-Cys—Gly—Phe—Cys)-D-Trp-D-Thr-D-Trp-D-Val—NH$_2$ |
| (92) | D-Arg-D-Lys-cyclo(D-Cys-D-Ile-Ile-D-Cys)-D-Trp-D-Thr-D-Trp-D-Val—NH$_2$ |
| (93) | D-Arg-D-Lys-cyclo(D-Cys-D-Ile—Phe-D-Cys)-D-Trp-D-Thr-D-Trp-D-Val—NH$_2$ |
| (94) | D-Arg-D-Lys-cyclo(D-Cys—His—Phe-D-Cys)-D-Trp-D-Thr-D-Trp-D-Val—NH$_2$ |
| (95) | D-Arg-D-Lys-cyclo(D-Cys—Ile—Pro-D-Cys)-D-Trp-D-Thr-D-Trp-D-Val—NH$_2$ |
| (96) | D-Arg-D-Lys-cyclo(D-Cys—Gly—Phe-D-Cys)-D-Trp-D-Thr—Trp-D-Val—NH$_2$ |
| (97) | D-Arg-D-Lys-cyclo(D-Cys—Gly—Phe-D-Cys)-D-Trp-D-Thr-D-Trp—Val—NH$_2$ |
| (98) | D-Arg-D-Lys-cyclo(D-Cys—Gly—Phe-D-Cys)-D-Trp—Thr-D-Trp-D-Val—NH$_2$ |
| (99) | D-Arg-D-Lys-cyclo(D-Cys—Gly—Phe-D-Cys)—Trp-D-Thr-D-Trp-D-Val—NH$_2$ |
| (100) | D-Arg-D-Lys-cyclo(D-Cys—Gly—Phe-D-Cys)-D-Tyr-D-Thr-D-Gln-D-Val—NH$_2$ |
| (101) | Arg-D-Lys-cyclo(D-Cys—Gly—Phe-D-Cys)-D-Trp-D-Thr-D-Trp-D-Val—NH$_2$ |
| (102) | D-Arg-D-Lys-cyclo(D-Cys—Gly—Phe-D-Cys)-D-Trp-D-Thr-D-Trp—Gln—NH-Bu |
| (103) | D-Arg-D-Lys-cyclo(D-Cys—Gly—Phe-D-Cys)-D-Trp-D-Val-D-Trp-D-Val |
| (104) | Ac-D-Lys-cyclo(D-Cys—Gly—Tyr-D-Cys)-D-Trp-D-Thr-D-Trp-D-Val—NH$_2$ |
| (110) | D-Arg-D-Ala-cyclo(D-Cys—Gly—Phe-D-Cys)-D-Trp-D-Thr-D-Trp-D-Val—NH$_2$ |
| (111) | D-Arg-D-Gln-cyclo(D-Cys—Gly—Phe-D-Cys)-D-Trp-D-Thr-D-Trp-D-Val—NH$_2$ |
| (112) | D-Arg-D-Glu-cyclo(D-Cys—Gly—Phe-D-Cys)-D-Trp-D-Thr-D-Trp-D-Val—NH$_2$ |
| (113) | D-Arg-D-Lys-cyclo(Cys—Gly—Gly—Cys)-D-Trp-D-Thr-D-Trp-D-Val—NH$_2$ |
| (114) | D-Arg-D-Lys-cyclo(D-Cys-D-Gln—Gln-D-Cys)-D-Trp-D-Thr-D-Trp-D-Val—NH$_2$ |
| (115) | D-Arg-D-Lys-cyclo(D-Cys—Gly-(p-Cl—Phe)-D-Cys)-D-Trp-D-Thr-D-Trp-D-Val—NH$_2$ |
| (116) | D-Arg-D-Lys-cyclo(D-Cys—Gly-D-Val-D-Cys)-D-Trp-D-Thr-D-Trp-D-Val—NH$_2$ |
| (117) | D-Asp-D-Lys-cyclo(D-Cys—Gly—Phe-D-Cys)-D-Trp-D-Thr-D-Trp-D-Val—NH$_2$. |

2. A pharmaceutical composition comprising at least one biologically active peptide of claim 1 in an amount effective to inhibit cellular adherence and a pharmaceutically acceptable carrier or diluent.

3. A method for modifying binding of a selectin in a host comprising administering to said host at least one biologically active peptide of claim 1 in an amount effective to inhibit cellular adherence.

* * * * *

UNITED STATES PATENT AND TRADEMARK OFFICE
CERTIFICATE OF CORRECTION

PATENT NO. : 5,753,617
DATED : May 19, 1998
INVENTOR(S) : George A. Heavner

It is certified that error appears in the above-indentified patent and that said Letters Patent is hereby corrected as shown below:

Col. 70, line 51, change "OOC" to --0°C--

Col. 73, line 4, change "(17)" to --(1)--

Signed and Sealed this

Seventeenth Day of August, 1999

Q. TODD DICKINSON

Attest:

Attesting Officer

Acting Commissioner of Patents and Trademarks